United States Patent
Luo et al.

(10) Patent No.: US 11,612,681 B2
(45) Date of Patent: Mar. 28, 2023

(54) COMPOSITIONS AND DEVICES FOR REMOVAL OF ENDOTOXINS AND CYTOKINES FROM FLUIDS

(71) Applicant: The Research Foundation for the State University of New York, Syracuse, NY (US)

(72) Inventors: Juntao Luo, Jamesville, NY (US); Lili Wang, Syracuse, NY (US); Changying Shi, Jamesville, NY (US)

(73) Assignee: THE RESEARCH FOUNDATION FOR THE STATE UNIVERSITY OF NEW YORK, Syracuse, NY (US)

( * ) Notice: Subject to any disclaimer, the term of this patent is extended or adjusted under 35 U.S.C. 154(b) by 458 days.

(21) Appl. No.: 16/644,782

(22) PCT Filed: Sep. 6, 2018

(86) PCT No.: PCT/US2018/049797
§ 371 (c)(1),
(2) Date: Mar. 5, 2020

(87) PCT Pub. No.: WO2019/051121
PCT Pub. Date: Mar. 14, 2019

(65) Prior Publication Data
US 2021/0060232 A1    Mar. 4, 2021

Related U.S. Application Data

(60) Provisional application No. 62/554,845, filed on Sep. 6, 2017.

(51) Int. Cl.
*A61M 1/36* (2006.01)
*B01D 15/20* (2006.01)
(Continued)

(52) U.S. Cl.
CPC ........ *A61M 1/3687* (2013.01); *A61M 1/3679* (2013.01); *B01D 15/20* (2013.01); *B01J 20/262* (2013.01); *B01J 20/28047* (2013.01); *C02F 1/285* (2013.01); *B01J 20/28054* (2013.01); *B01J 20/3214* (2013.01); *B01J 20/3219* (2013.01); *B01J 20/3272* (2013.01); *C02F 1/68* (2013.01); *C02F 1/685* (2013.01)

(58) Field of Classification Search
None
See application file for complete search history.

(56) References Cited

U.S. PATENT DOCUMENTS

| 9,644,038 | B2 | 5/2017 | Luo et al. |
| 2009/0211976 | A1 | 8/2009 | Seidel et al. |
| 2014/0363371 | A1* | 12/2014 | Luo ..................... C08G 83/004 424/9.1 |

FOREIGN PATENT DOCUMENTS

WO    2017/044933 A1    3/2017

\* cited by examiner

*Primary Examiner* — Clare M Perrin
(74) *Attorney, Agent, or Firm* — Peter Fallon; Lance D. Reich

(57) ABSTRACT

Provided are sorption materials and devices using the sorption materials, and methods of using the sorption materials and devices containing the sorption materials. In various examples, the sorption materials bind to various inflammation stimulating and/or mediating molecules, which are often associated with systemic infections and systemic inflammation associated with conditions such as, for example, sepsis.

9 Claims, 43 Drawing Sheets

(51) Int. Cl.
B01J 20/26 (2006.01)
B01J 20/28 (2006.01)
C02F 1/28 (2006.01)
B01J 20/32 (2006.01)
C02F 1/68 (2006.01)

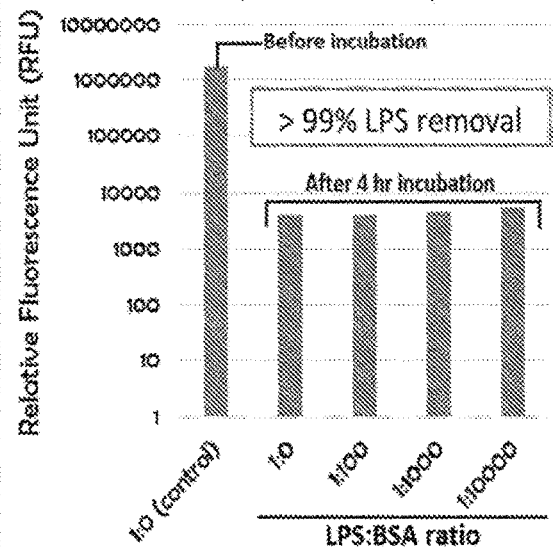
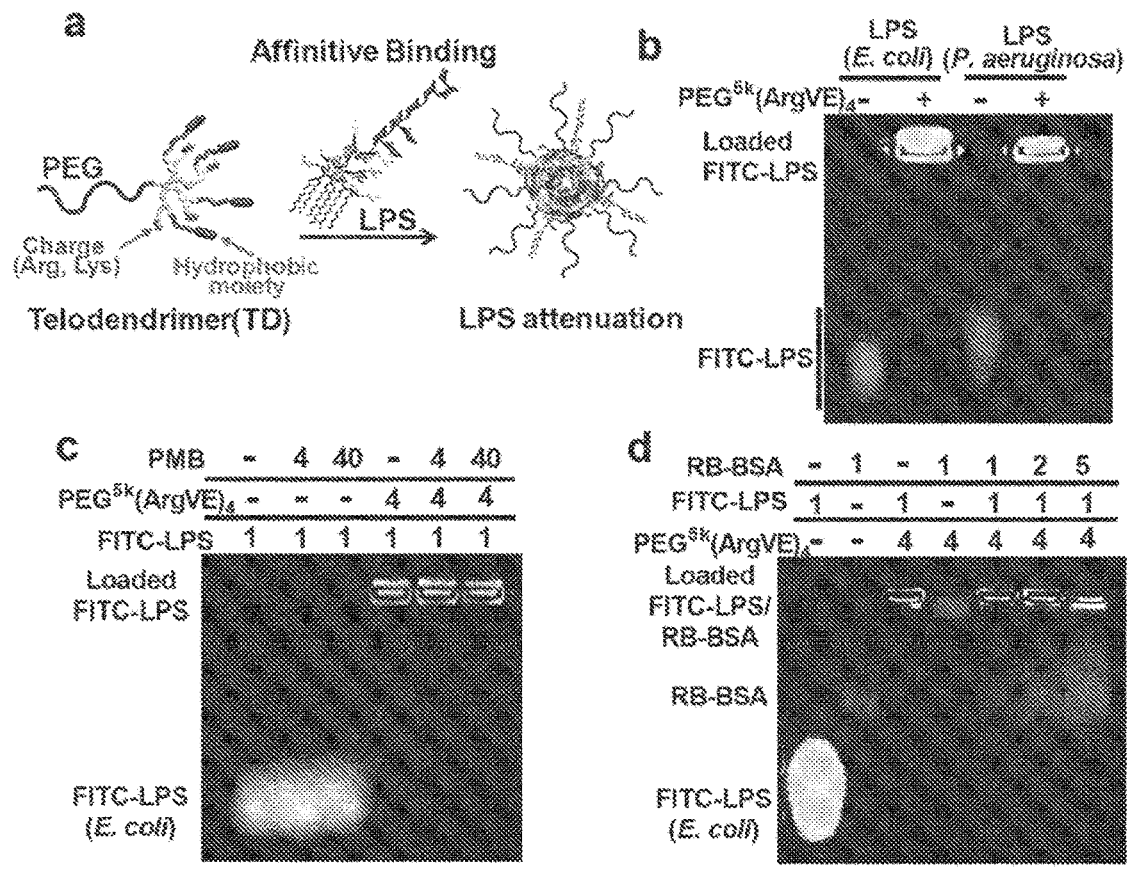
FIG. 14

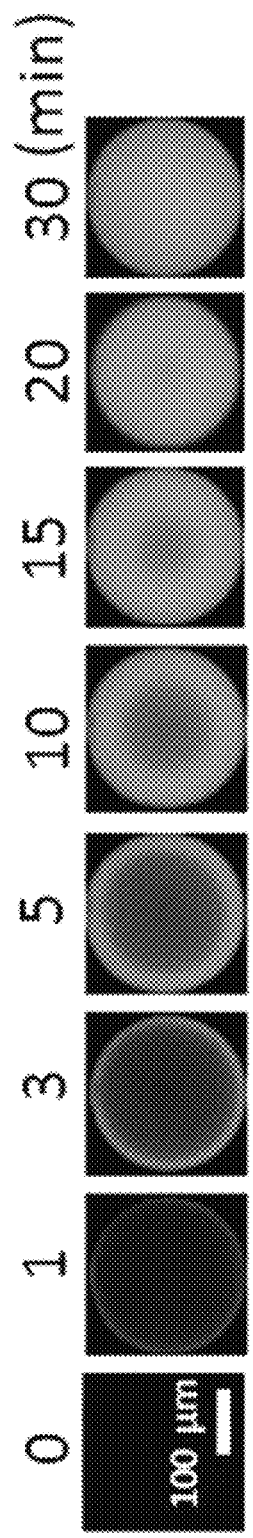
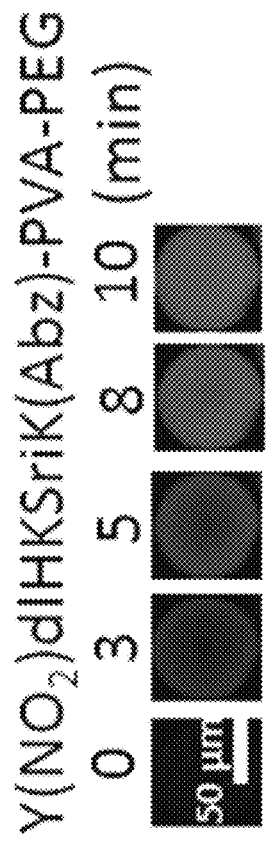
Fig. 27A

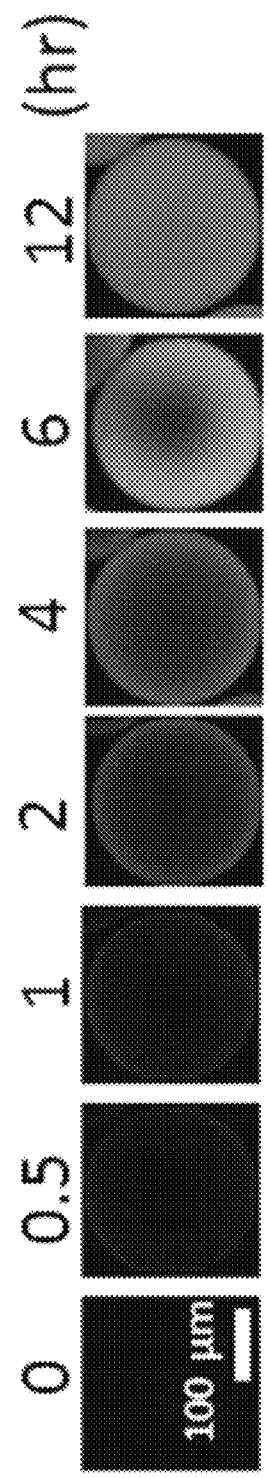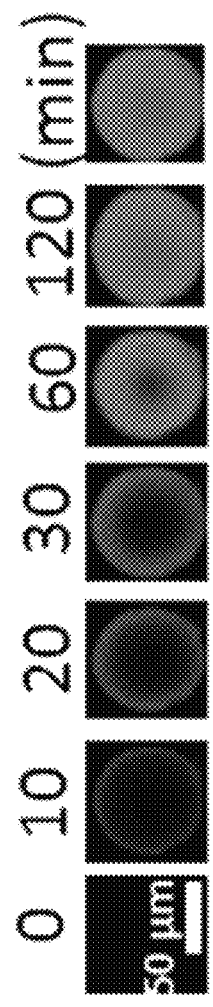
Fig. 27C a DNA binding/BSA competing
| DNA | 1 | 1 | 1 | 1 | - | 1 | - | 1 |
|---|---|---|---|---|---|---|---|---|
| FITC-BSA | - | 1 | 10 | 40 | 1 | 40 | 10 | - |
| $PEG^{5k}(Arg_2Rf)_4$ | 10 | 10 | 10 | 10 | 3 | - | - | - |
(w/w) Loaded
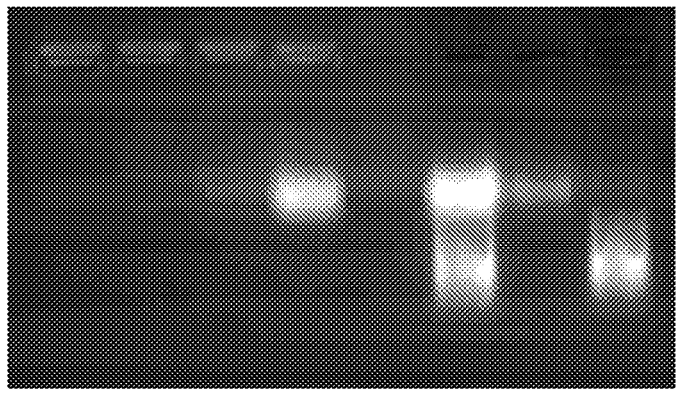
b Attenuation of free Heme Protoporphyrin IX (PPIX) by TD
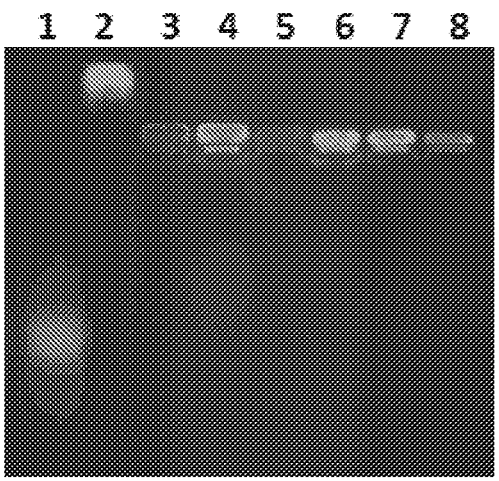
1. Free PPIX
2. 1:20(w/w) PPIX : $PEG^{5k}Arg_8OAc_4$
3. 1:20(w/w) PPIX : $PEG^{5k}Ve_4NH2_8$
4. 1:20(w/w) PPIX : $PEG^{5k}Arg_8C17_4$
5. 1:20(w/w) PPIX : $PEG^{5k}Arg_4C17_4$
6. 1:20(w/w) PPIX : $PEG^{5k}Arg_8Ve_4$
7. 1:20(w/w) PPIX : $PEG^{5k}Arg_4Ve_4$
8. 1:20(w/w) PPIX : $PEG^{5k}Arg_4CHO_4$
FIG. 32

COMPOSITIONS AND DEVICES FOR REMOVAL OF ENDOTOXINS AND CYTOKINES FROM FLUIDS

CROSS REFERENCE TO RELATED APPLICATIONS

This application claims priority to U.S. Provisional Application No. 62/554,845, filed on Sep. 6, 2017, the disclosure of which is hereby incorporated by reference.

STATEMENT REGARDING FEDERALLY SPONSORED RESEARCH

This invention was made with government support under contract no. EB019607, awarded by the National Institutes of Health. The government has certain rights in the invention.

FIELD OF THE DISCLOSURE

The disclosure generally relates to telodendrimers. More particularly the disclosure relates to telodendrimers suitable for removal of inflammation stimulating and/or mediating molecules.

BACKGROUND OF THE DISCLOSURE

With the population aging, the increased use of chemotherapeutics, and the emerging drug-resistant bacteria strains, the incidence of sepsis hospitalization has substantially increased. The mortality rates of sepsis have only marginally decreased even during the modern era of critical care, ranging from 18% to 50% for sepsis and septic shock patients. Lipopolysaccharide (LPS) sheds off from the outer cell membrane of gram-negative (GN) bacteria, which is the most important immunogen frequently causing severe infections in blood stream, i.e. GN sepsis. The binding of LPS to the Toll-like receptors (e.g., TLR-4) on epithelial cells, monocytes and macrophages induces proinflammatory cytokine production, leading to tissue damage, multiple organ failure, and death. The search for a way to neutralize and remove LPS from patient blood has been a consistent interest of researchers seeking an effective sepsis treatment.

Hemoperfusion (HP) is a promising technique to control sepsis by physical removal of the septic molecules from patient blood. PMB-based cartridge (Toraymyxin®) has been approved in Japan and Europe for LPS removal in sepsis treatment. Recently, a CytoSorb® cartridge packed with size-exclusive hydrophobic resins (5-60 kDa) has been approved in Europe to adsorb cytokines nonspecifically in critically ill patients undergoing cardiac surgery in order to prevent cytokine storm. Unfortunately, both Toraymyxin® and CytoSorb® failed to demonstrate the survival benefit in severe sepsis treatment in the most recent randomized controlled clinical trials. Therefore, a novel HP technique is desperately needed in the clinic to simultaneously and efficiently remove endotoxin, cytokines, and a broad range of triggers and mediators of sepsis (e.g., pathogen/damage-associated molecular patterns (PAMPs/DAMPs)) in order to control hyperinflammation for sepsis treatment.

It has been shown that anion exchange resins (e.g., DEAE or PEI groups bound to cellulose) are very well suitable for endotoxin binding. However, the undesired binding of important factors of the intracorporeal coagulation system such as protein C and protein S and the coagulation problems connected thereto are disadvantageous. These coagulation problems can be avoided by the use of a specific sorption agent, which has immobilized antibodies against endotoxins. TLR-4 targeted therapies (e.g., TLR-4 antibodies, and LPS antagonists) have been investigated as ways to treat sepsis by blocking LPS-induced cytokine production. However, these therapies have yet to show significant decrease in mortality of sepsis in clinical trials and their use only has limited applicability for economic reasons. In addition to LPS antibodies, cationic amphiphilic small molecules, peptides, and proteins, have been developed and studied as anti-LPS reagents. Unfortunately, these cationic reagents exhibit nonspecific protein binding and systemic toxicity. Efforts to translate these researches from bench to improved clinical endpoints have to date been unsuccessful. The unsatisfactory clinical outcomes of these reagents are associated with their low potency, non-specificity, and toxicity.

Polymyxin B (PMB), is one of the most potent LPS binders. Its application has been hindered by its severe nephrotoxicity and neurotoxicity which precludes its use systemically. EP 0 129 786 A2 describes an endotoxin detoxification material having a fibrous carrier, on which polymyxin is covalently immobilized. The fibrous carrier is equipped with functional groups to covalently bond polymyxin to the surface of the carrier. The endotoxin detoxification material from EP 0129 786 is on the market as a filler material for an adsorption module (trade name: Toraymyxin) and at the moment it is the only sorption agent which is authorized for clinical treatment of sepsis in the scope of extracorporeal blood purification. A critical review of the effectiveness of fibers carriers having immobilized polymyxin B, in which the quality of the treatment is represented as suboptimal, has only recently been published.

The cytokine storm induced by systemic endotoxin exposure causes hyperinflammatory responses in sepsis. Although organ dysfunction following sepsis can go through a series of molecular and cellular mechanisms, the unpaired inflammatory response represents an important and central component of sepsis. Antibodies targeting proinflammatory cytokines (e.g., TNF and IL-1) have shown clinical benefit but didn't lead to a statistically significant improvement in the 28-day mortality of sepsis because numerous of proinflammatory cytokines need to be neutralized simultaneously. It appears that systemic inflammation in sepsis requires more than anti-cytokine or anti-LPS monotherapy to reduce mortality rates. A CytoSorb® cartridge based on the size exclusive absorbance has been applied for hemoperfusion use to reduce cytokines in the critically ill and cardiac surgery patients to control inflammation. In addition, a PMB-containing cartridge has been used to efficiently remove LPS by hemoperfusion to improve sepsis treatment; however, reductions in sepsis mortality have been modest. There is a need to develop more effective materials for the removal of both LPS and cytokine to control severe inflammation in sepsis.

Apheresis methods are extracorporeally performed methods, in which pathophysiologically-relevant blood and plasma components, for example, biomolecules such as (glyco)proteins, peptides, lipids, lipoproteins, and lipopolysaccharides, but also blood cells and blood plasma, are removed. Apheresis methods can be used for diagnostic and therapeutic purposes, on the one hand, they also represent a very effective possibility for obtaining specific blood components from healthy individuals in a sufficient quantity and in sufficiently high purity, on the other hand. Great significance is ascribed to the therapeutic apheresis, since for specific indications, this is often a very effective alternative, which simultaneously has few side effects, to medicinal treatment. Thus, in plasmapheresis methods, the plasma can either be completely separated and replaced by a substitution solution, or only specific components such as LDL, endotoxins, or immunoglobulins are removed therefrom using a sorption agent and the plasma is subsequently returned to the donor/patient.

To remove endotoxins from a biological fluid (typically blood or blood plasma) which is contaminated with endotoxins, it is brought into close contact with a sorption agent, which is typically located in a sorption apparatus. The endotoxins are bound to the surface of the sorption agent and are removed from the biological fluid. The biological fluid which is freed from endotoxins is returned to the patient. The sorption apparatus is either situated on the blood side in an extracorporeal blood circuit or on the filtrate side in a plasma circuit of an extracorporeal blood purification device. The endotoxin binding capacity and speed are a function of the composition of the sorption agent.

The speed of the endotoxin binding by the sorption agent is decisive for the survival of the patient. The time which remains to remove the endotoxins from the blood of a patient is very short (<12 hours) and can be only a few hours in the case of severe sepsis.

Although the lethality of patients having endotoxin toxicity, in particular sepsis, has been able to be reduced by the clinical application of the above-mentioned Toraymyxin adsorption module, the lethality of patients having severe sepsis and septic shock is still very high in spite of maximum therapy. For this reason and because of the high and rising incidence of septic states, there is a high demand for a sorption agent having improved sorption performance for endotoxins. However, the development of novel and stronger endotoxin-binding (especially LPS-binding) reagents remains of great interest to researchers and clinicians, given the significant and demonstrated role of LPS in sepsis pathopharmacology. There is a need for a more effective endotoxin-binding material for use in cartridges. There is also a need for a nontoxic endotoxin-binding compound that is safe for injection into patients.

SUMMARY OF THE DISCLOSURE

In an aspect, the present disclosure provides sorption materials. The sorption materials comprise telodendrimers that are linear-dendritic copolymers having both charged moieties and binding moieties (e.g., LPS binding moieties) as end groups. Telodendrimers may be attached to a substrate or stationary phase, such as a fiber, solid surface, hydrogel matrix, bead, particle (e.g., microparticles, nanoparticles, and the like), mat, membrane, or porous monolith, and may be attached to an external surface or to an internal surface of the substrate (i.e., the surface of a pore in, such as, for example, a porous fiber, bead or monolith).

In an aspect, the present disclosure provides sorption materials. The sorption materials may exhibit a dual mode of action to control hyperinflammation in sepsis. In an example, a sorption telodendrimer has one or more charged groups and one or more lipophilic and/or hydrophobic LPS binding group (LBM group(s)).

Sorption materials can have the following structure:

(Formula 1a)

(Formula 1b)

where $R^1$ and/or $L^1$ and/or $L^2$ are optional. In an example, sorption materials have at least one compound of formula 1a or a group derived therefrom. In an example, a sorption material having a substrate (e.g., S-$R^1$-$L^1$-D-$(L^2$-$R^2)_{x,y}$ has a plurality of compounds of formula 1a attached to the substrate (e.g., S-$(R^1$-$L^1$-D-$(L^2$-$R^2)_{x,y})_n$, where n refers to the number of compounds on the substrate and is at least one).

In an aspect, the present disclosure provides molecular or nanoparticle (e.g., nanoparticles having a largest dimension, such as, for example, a diameter of 1-100 nm, including every nm value and range therebetween) compositions comprising sorption materials (e.g., sorption materials comprising compound 1a, and optionally, a substrate) of the present disclosure. Non-limiting examples of compositions include solutions, suspensions, emulsions, solid injectable compositions that are dissolved or suspended in a solvent before use, and the like. The injections may be prepared by dissolving, suspending or emulsifying one or more of the active ingredients in a diluent. Examples of diluents, include, but are not limited to distilled water for injection, physiological saline, vegetable oil, alcohol, and a combination thereof. Further, the injections may contain stabilizers, solubilizers, suspending agents, emulsifiers, soothing agents, buffers, preservatives, etc. The injections may be sterilized in the final formulation step or prepared by sterile procedure. The composition of the disclosure may also be formulated into a sterile solid preparation, for example, by freeze-drying, and can be used after sterilized or dissolved in sterile injectable water or other sterile diluent(s) immediately before use.

In an aspect, the present disclosure provides devices comprising one or more sorption materials of the present disclosure. Devices of the present disclosure can be used to remove inflammation stimulating and/or mediating molecules from a fluid (e.g., a bodily fluid).

Sorption materials of the present disclosure are of particular use in extracorporeal blood purification (apheresis), such as for a subject who has or is suspected of having a systemic infection (e.g., systemic bacterial infection) (e.g., sepsis) (i.e., therapeutic use), systemic inflammation, and/or dysfunctional kidneys (e.g., subjects undergoing dialysis). Such blood purification may include the removal of inflammation stimulating and/or mediating molecules (e.g., endotoxins and/or cytokines).

In an aspect, the present disclosure provides methods using sorption materials and devices comprising sorption materials of the present disclosure. Methods of the present disclosure may involve administering a sorption material of the present disclosure to a subject in need of treatment who has been diagnosed with or is suspected of having a systemic bacterial infection (e.g., sepsis) (i.e., therapeutic use) and/or systemic inflammation, and/or passing a bodily fluid of the subject through a device comprising a sorption material of the present disclosure. A method can be carried out in a subject in need of prophylaxis for systemic bacterial infections/illnesses and/or systemic inflammation. Inflammation stimulating and/or mediating molecules of the present disclosure are associated with systemic bacterial infection and/or systemic inflammation. In a method of the present disclosure, one or more or all inflammation stimulating and/or mediating molecules bind to the sorption material of the present disclosure. In various examples, a method is carried out using a device of the present disclosure.

In an example, inflammation stimulating and/or mediating molecules (e.g., endotoxins, cytokines, and the like, and combinations thereof) are removed to a desirable degree and at desirable speed from a biological fluid using sorption materials of the present disclosure. The present disclosure also provides a sorption material that is non-toxic relative to polymyxin. The present disclosure provides methods for using such materials to remove endotoxins and inflammatory cytokines from biological fluids, particularly as a treatment for illness caused by such inflammation stimulating and/or mediating molecules (e.g., endotoxins, cytokines, and the like, and combinations thereof).

In an example, when an inflammation stimulating and/or mediating molecule binds to a sorption material of the present disclosure, the inflammation stimulating and/or mediating molecule is neutralized and cannot bind to anything aside from the sorption material.

In an aspect, the present disclosure provides a method to attenuate endotoxins, cytokines, DAMPs/PAMPs molecules, and the like, and combinations thereof in a fluid (e.g., a bodily fluid, such as, for example, blood, serum, and the like, and a combination thereof, or a culture medium). This includes, for example, the attenuation of endotoxins, cytokines and DAMPs/PAMPs molecules in the blood of subjects diagnosed with sepsis and/or septic shock, and of subjects undergoing dialysis.

BRIEF DESCRIPTION OF THE FIGURES

For a fuller understanding of the nature and objects of the disclosure, reference should be made to the following detailed description taken in conjunction with the accompanying figures.

FIG. 13 shows efficiency for LPS removal in the presence of high concentration of BSA after 4 h incubation with PVA-PEG-$(ArgVE)_4$ resin.

FIG. 14 shows a) a schematic illustration of the formation of telodendrimer nanotrap for LPS affinitive binding. Agarose gel electrophoresis profiles of LPS loading with telodendrimer $PEG^{5k}(ArgVE)_4$ and PMB: b) LPS, originated from E. coli and P. aeruginosa, were loaded by $PEG^{5k}(ArgVE)_4$. c) The stability of FITC-LPS (E. coli) loaded $PEG^{5k}(ArgVE)_4$ nanocomplex in the absent or presence of PMB at different mass ratio. d) The stability of FITC-LPS loaded $PEG^{5k}(ArgVE)_4$ nanocomplex in the absent or presence of serum protein (RB-BSA) at different mass ratio.

Figure 18:
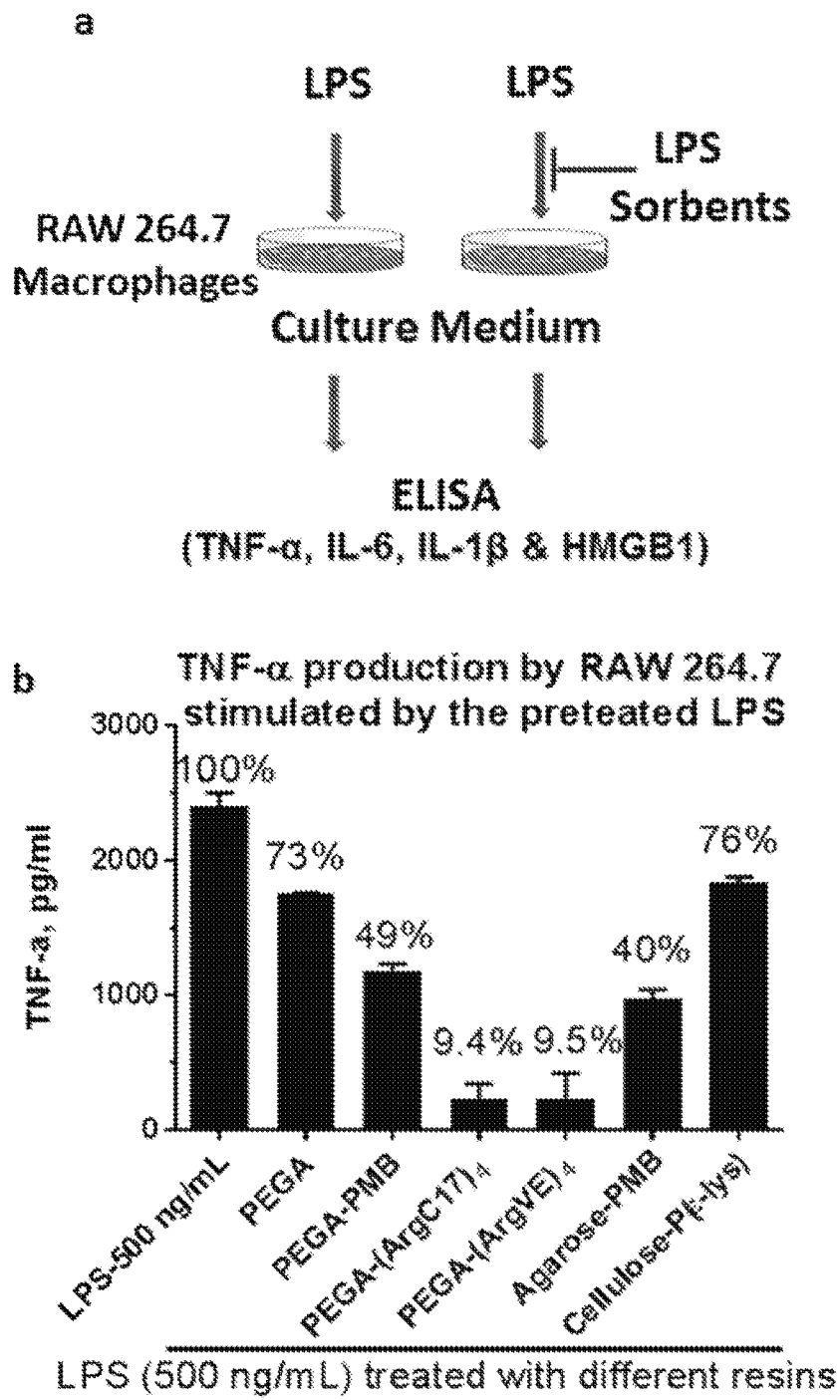

FIG. 18 shows a) a schematic representation of the TNF-α production stimulated by LPS post-resin removal in RAW 264.7 macrophages cell. b) Quantitative amount of TNF-α produced by RAW 264.7 cell as measured by ELISA assay.

Figure 19:
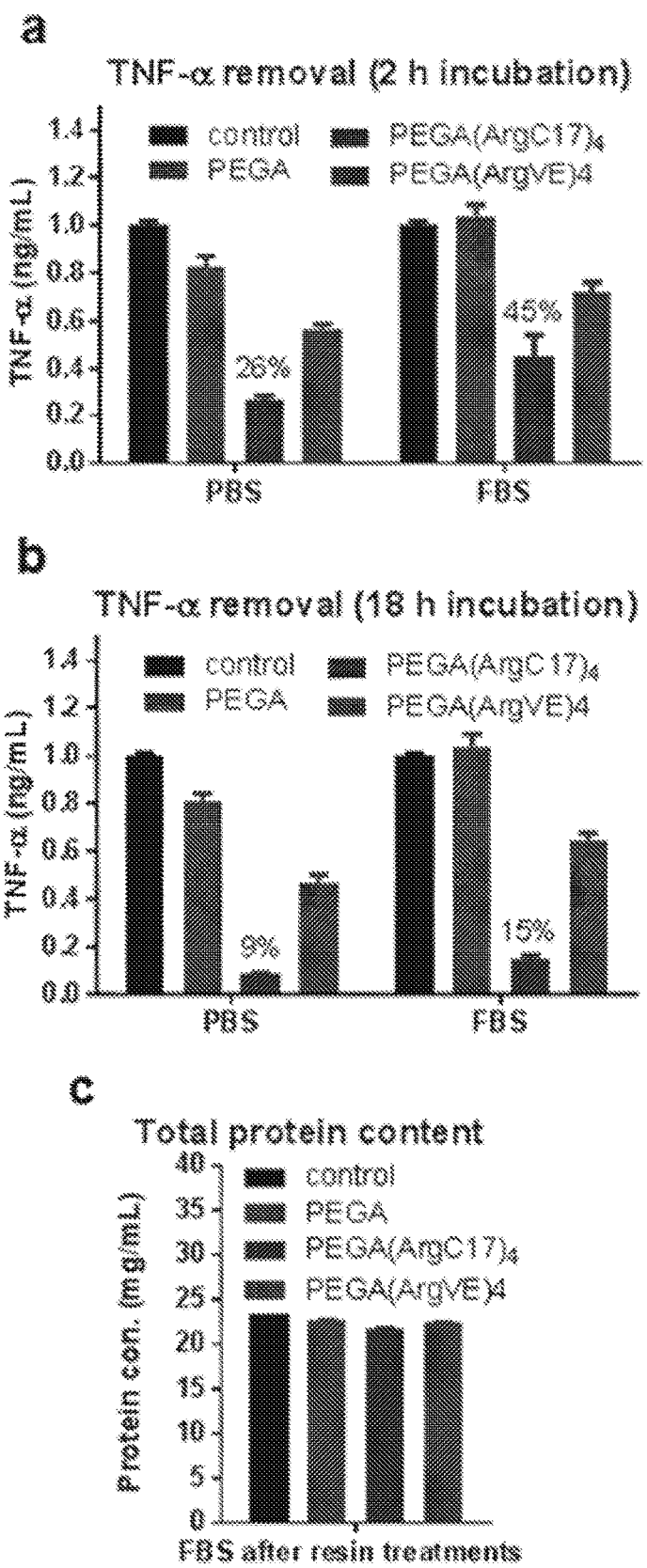

FIG. 19 shows TNF-α removal by different PEGA resins in PBS and FBS respectively after incubation for a) 2 h and b) 18 h. c) Total protein concentration of FBS after resin incubation for 18 h. In each series of four columns, from left to right, the columns correspond to control, PEGA, PEGA9ArgC17)$_4$, and PEGA(ArgVE)$_4$.

Figure 20:
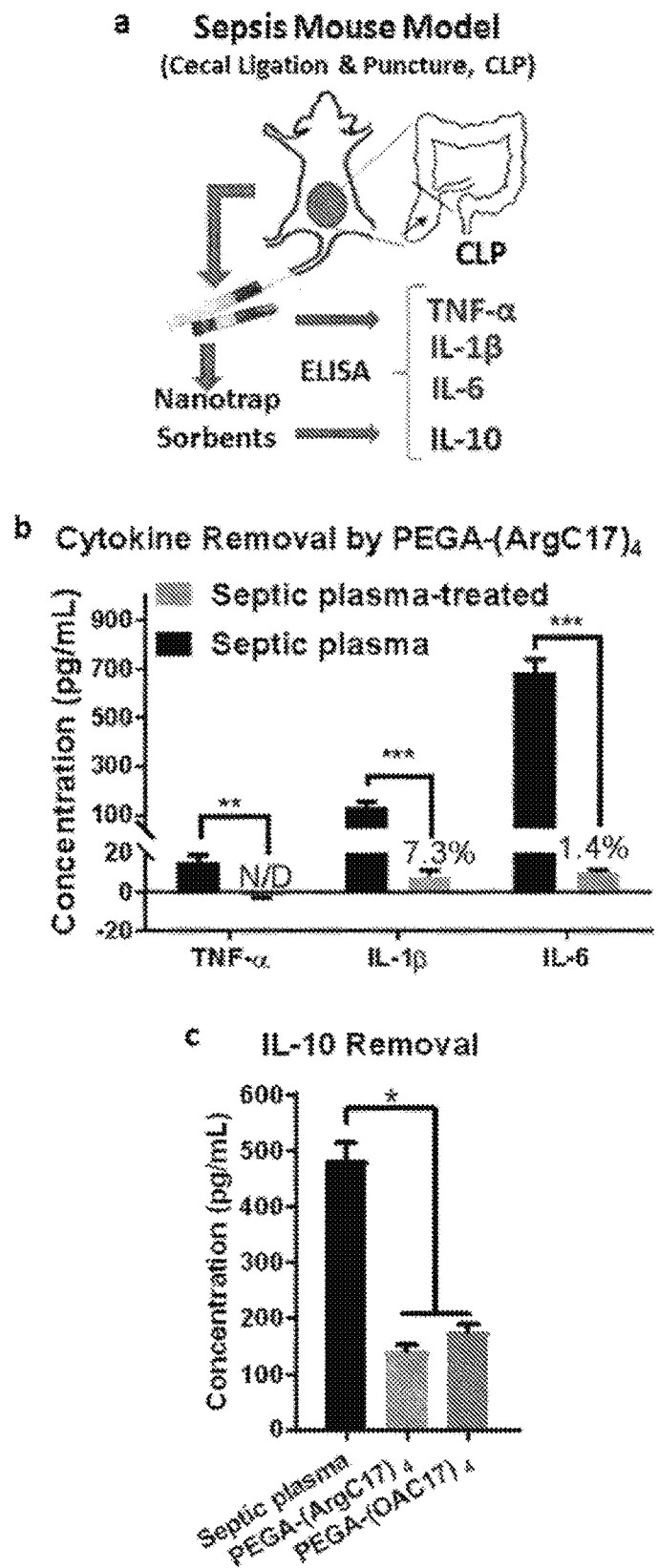

FIG. 20 shows a) a schematic illustration of sepsis mouse model induced by CLP procedure and the experimental design of ex vivo proinflammatory cytokine removal and detection in septic plasma. b) The efficiency of the positively charged PEGA-(ArgC17)$_4$ nanotrap resins for ex vivo scavenging of three major negatively charged proinflammatory cytokines (TNF-α, IL-1β, and IL-6) from the septic plasma obtained from CLP mouse sepsis models. c) The adsorption efficiency of the positively charged anti-inflammatory cytokine IL-10 by PEGA-(ArgC17)$_4$ or PEGA-(OAC17)$_4$ nanotrap resins from CLP-septic mice plasma. N/D: non-detectable; * P<0.05;  P<0.01; * P<0.001.

Figure 21:
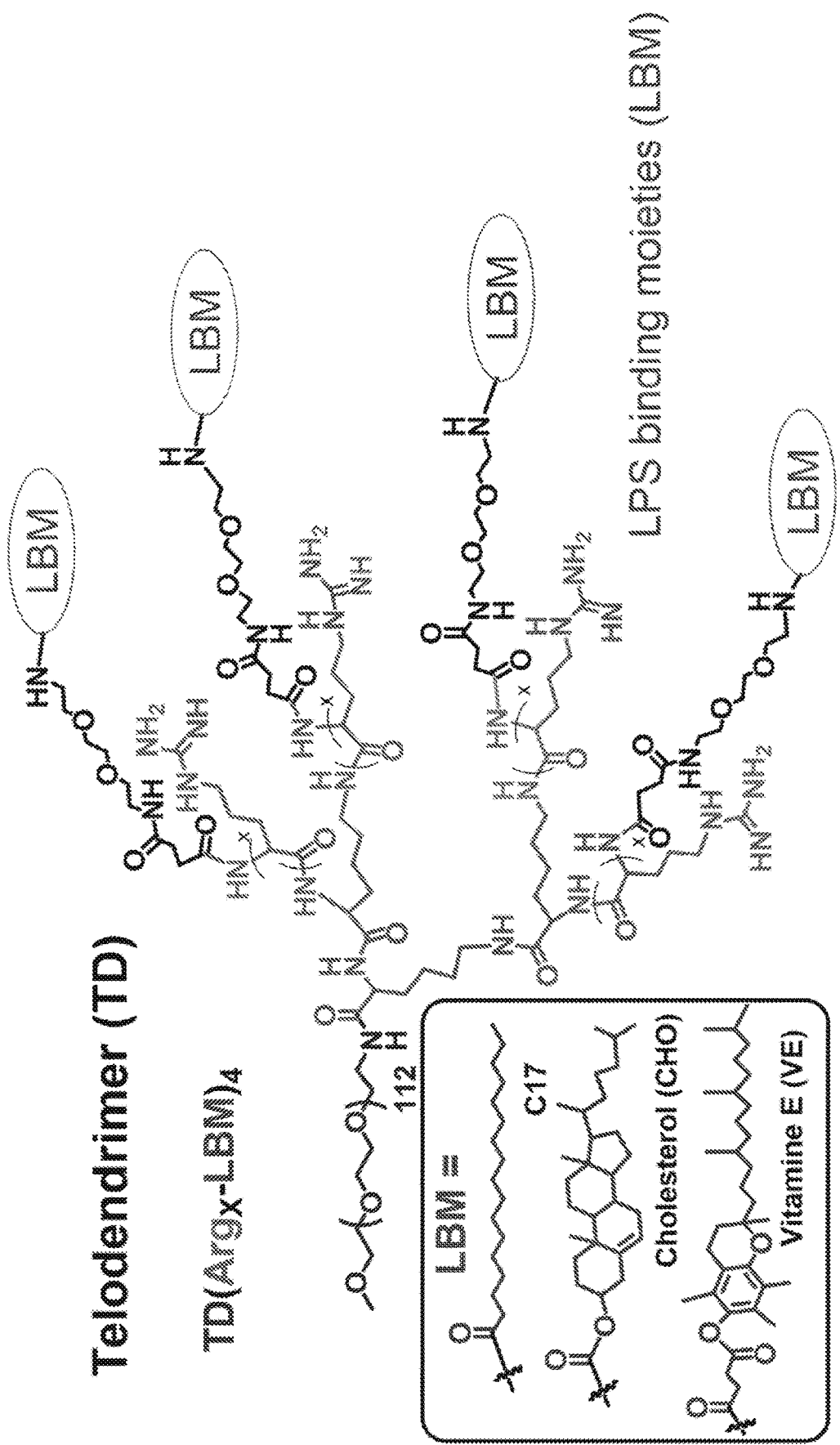

FIG. 21 shows chemical structures of telodendrimers with varying LPS binding moieties (LBM).

Figure 22:
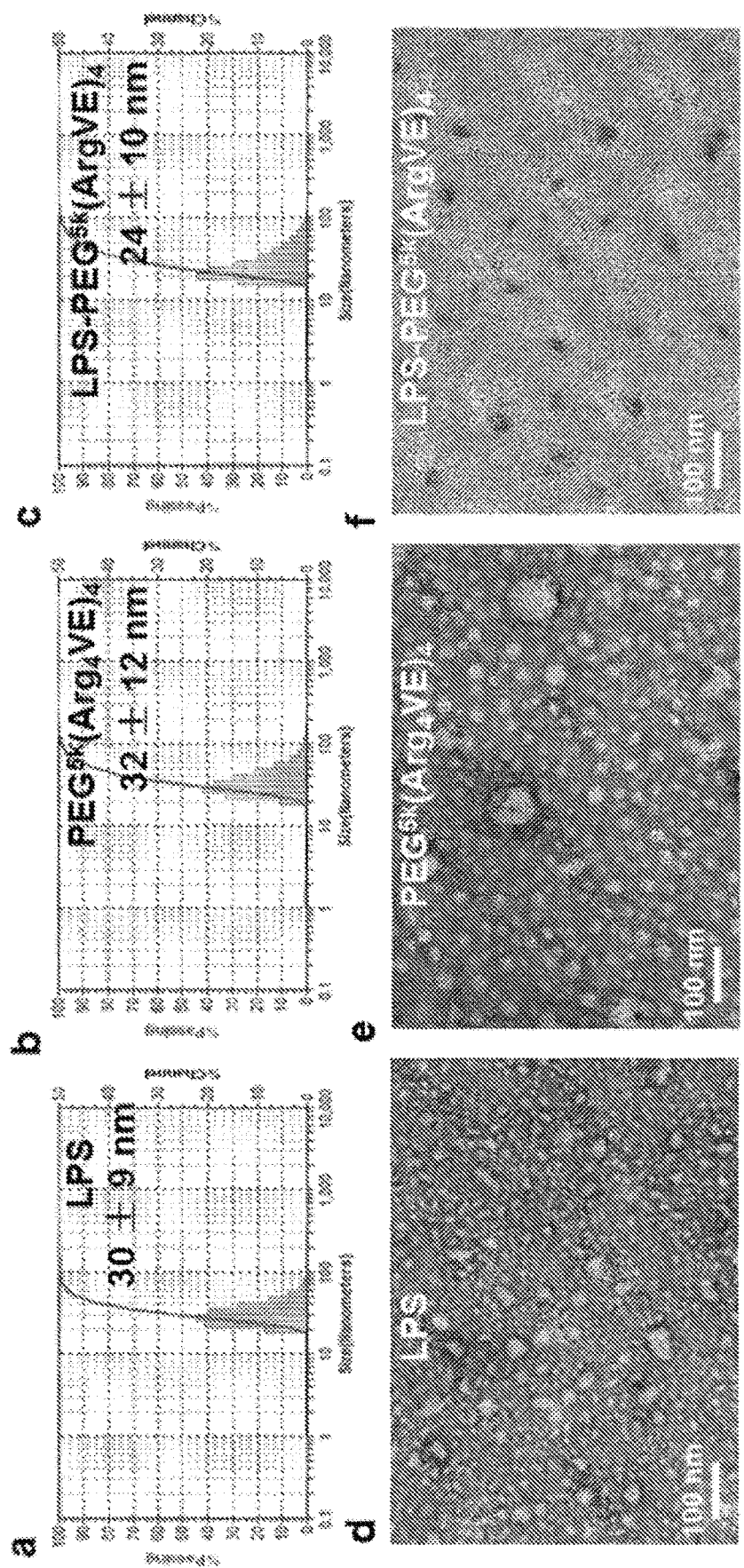

FIG. 22 shows particle size characterizations by DLS (a-c) and TEM (d-f) characterization for LPS (a and d), telodendrimer PEG$^{5k}$(ArgVE)$_4$ (b and e) and LPS loaded nanotrap (c and f).

Figure 23:
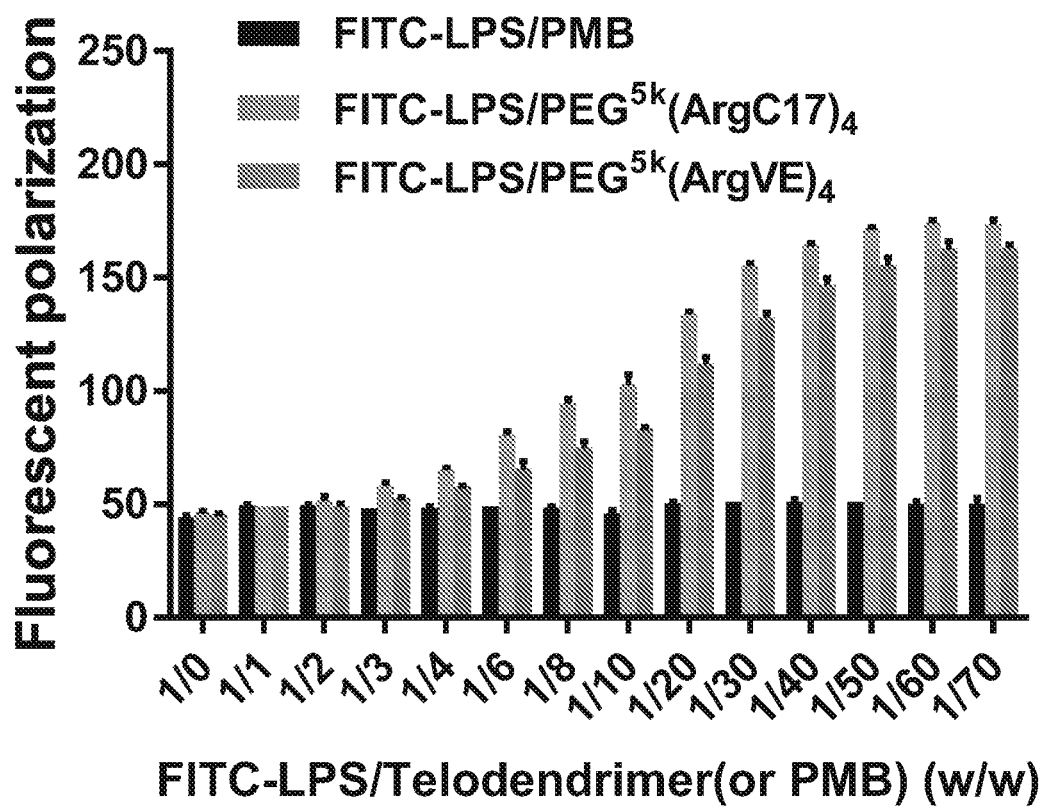

FIG. 23 shows fluorescent polarization of FITC-LPS (10 µg/mL, <CMC of LPS) in nanocomplex of PMB, PEG$^{5k}$(ArgC17)$_4$, and PEG$^{5k}$(ArgVE)$_4$ in PBS.

Figure 24:
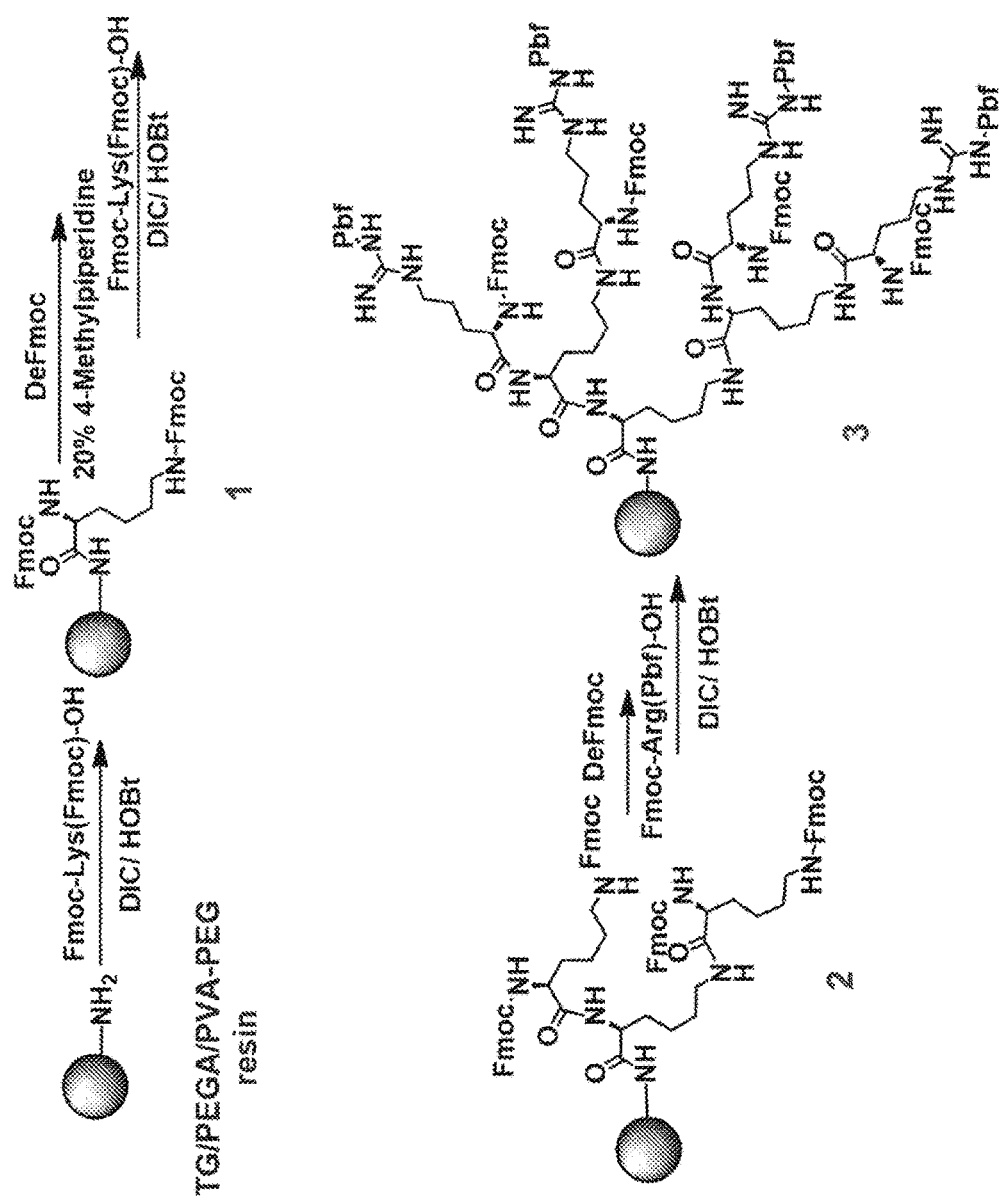
Figure 24:
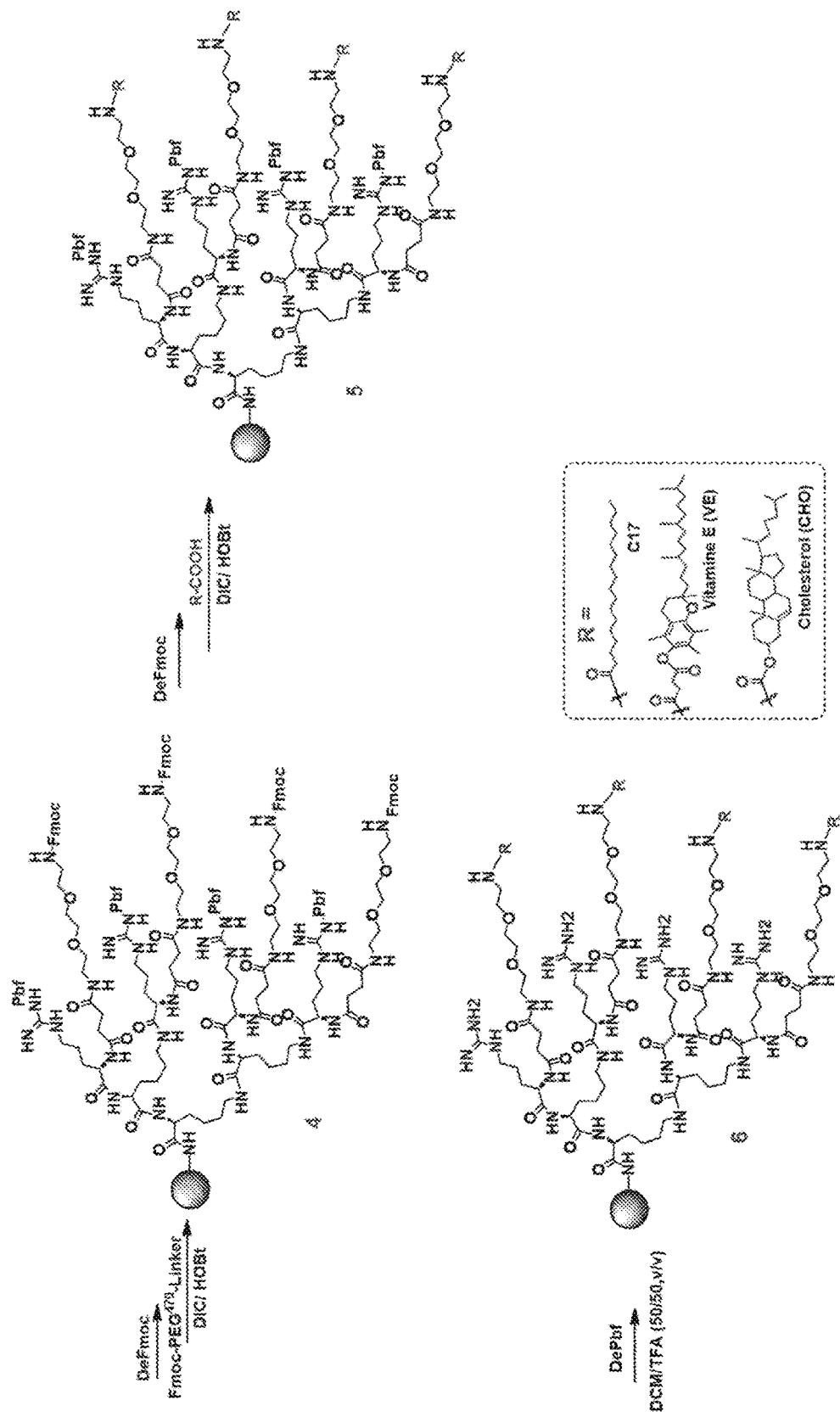

FIG. 24 shows a stepwise synthetic route for resin functionalization with telodendrimer for LPS removal.

Figure 25:
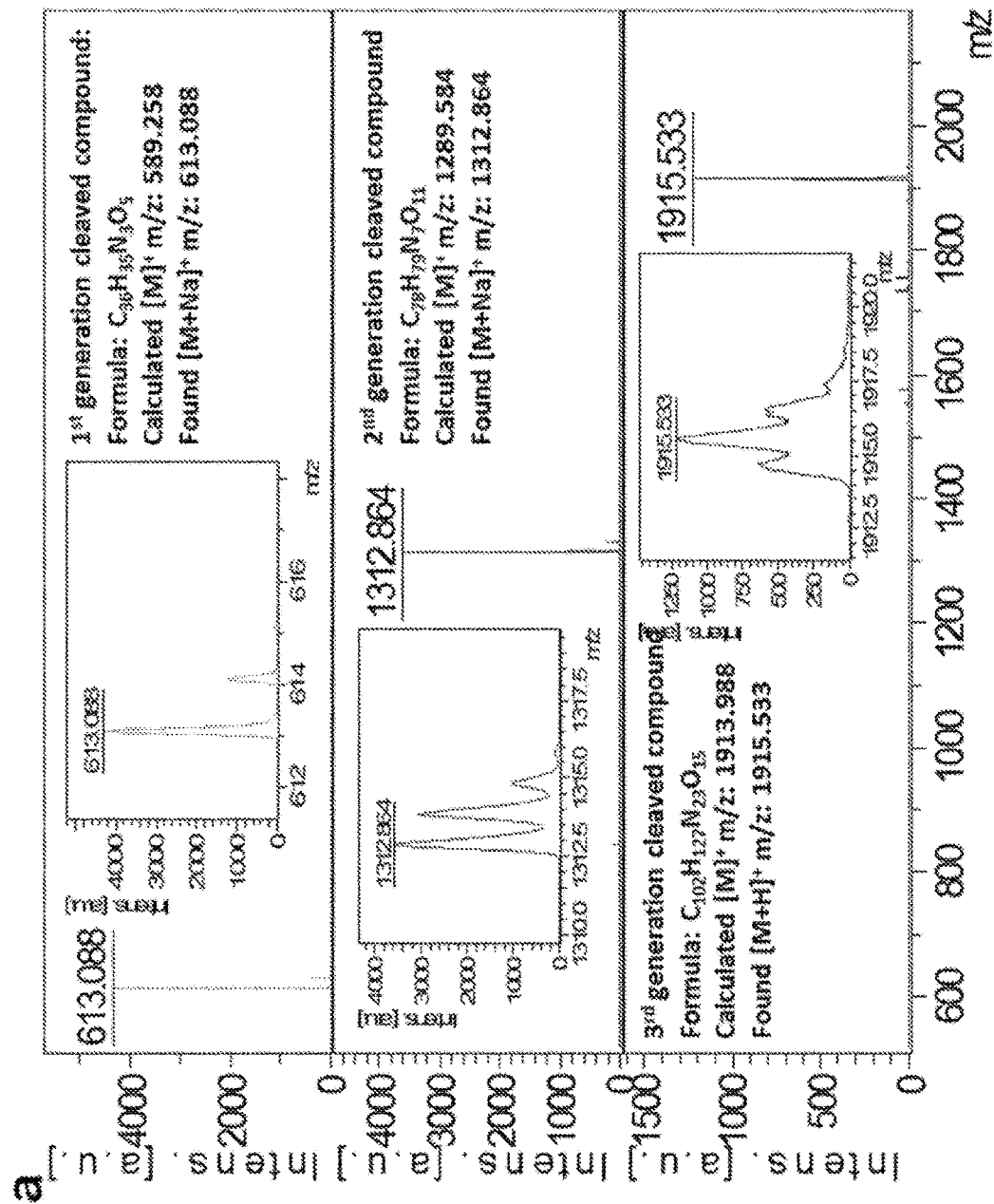
Figure 25:
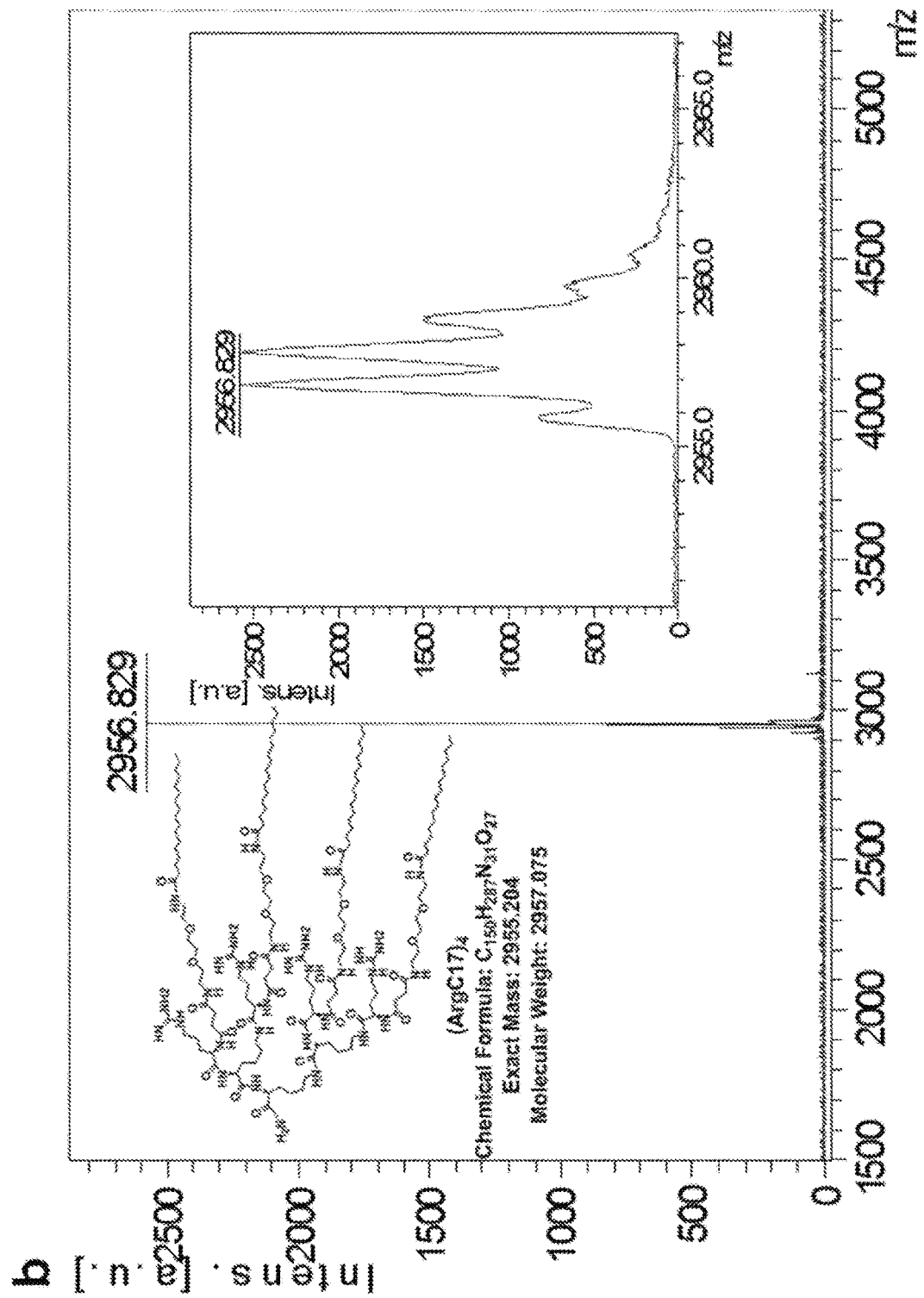
Figure 25:
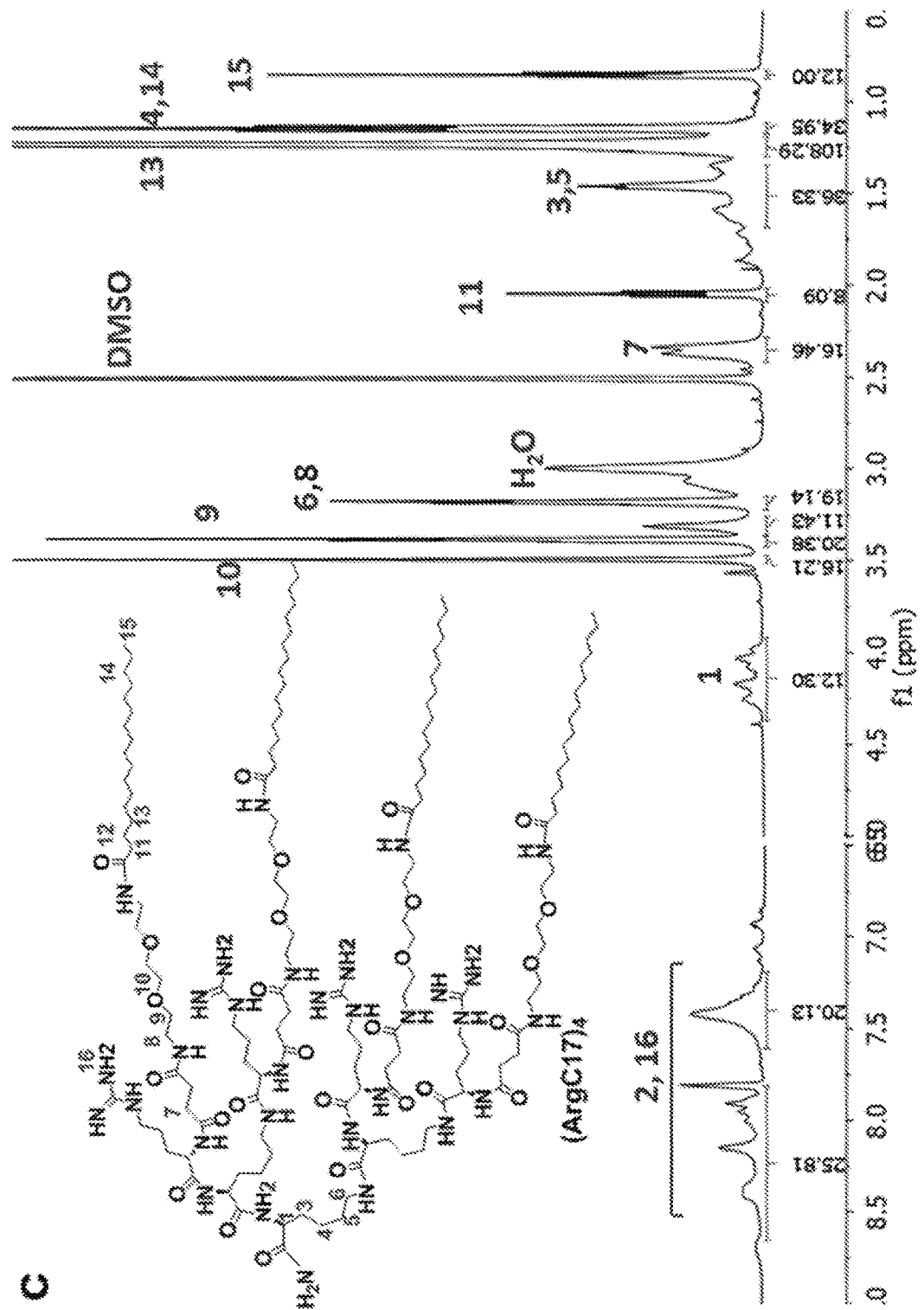

FIG. 25 shows structural characterizations of intermediates synthesized on Rink resin. a) Stacked MALDI-TOF spectra of intermediates at each dendritic generation. b) MADLI-TOF spectrum of (ArgC17)$_4$ cleaved from Rink resin. c) $^1$H NMR spectrum of (ArgC17)$_4$, recorded in DMSO-d$_6$.

Figure 26:
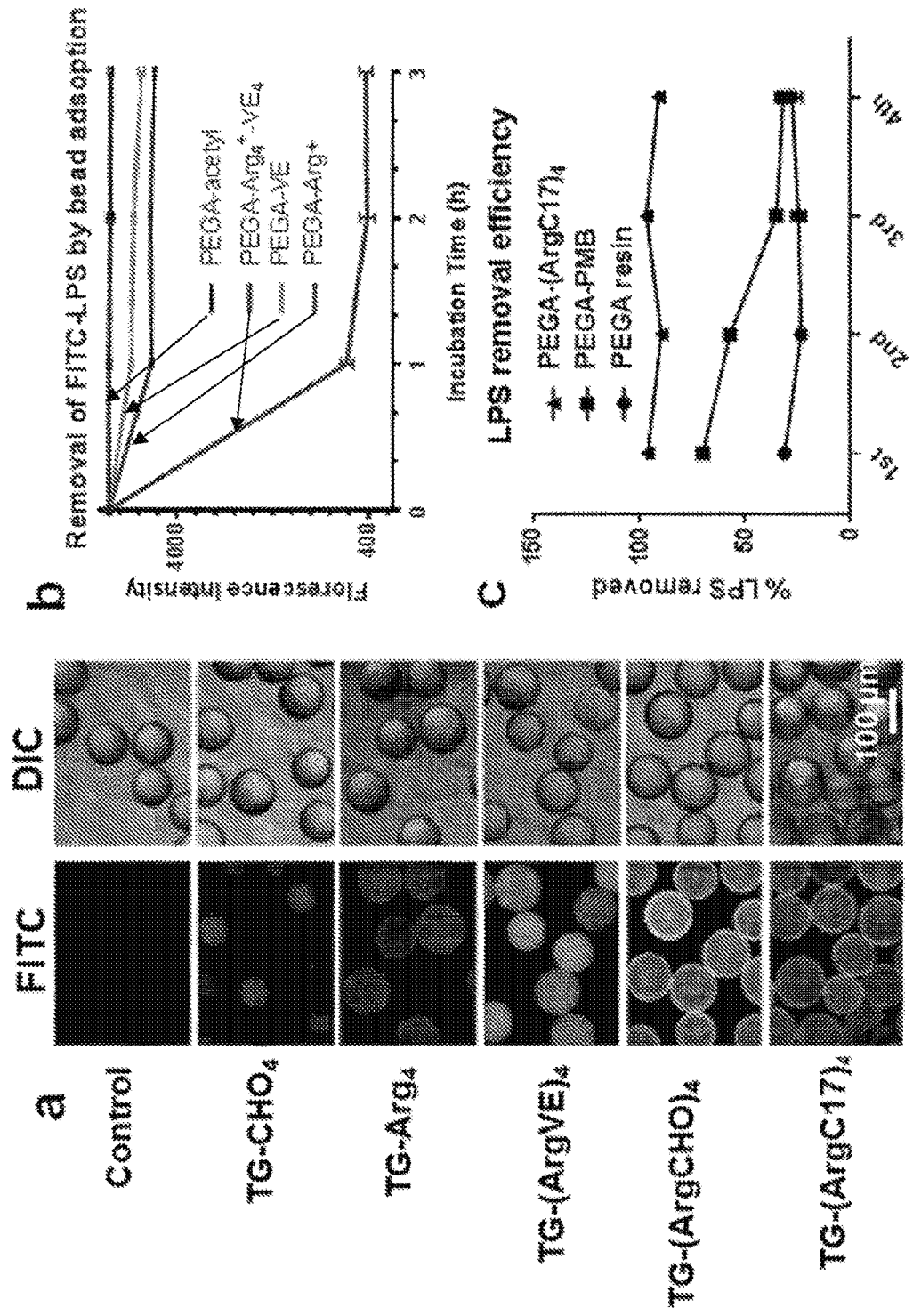

FIG. 26 shows a) a fluorescent microscopy images of FITC-LPS adsorption on resins modified with different functionalities. b) FITC-LPS removal efficiency of PEGA resins modified with different functionalities. c) The LPS removal efficiency (2 h incubation in PBS) of PEGA-(ArgC17)$_4$ resin after several cycles of regeneration using 0.2 M NaOH in ethanol.

Figure 27B:
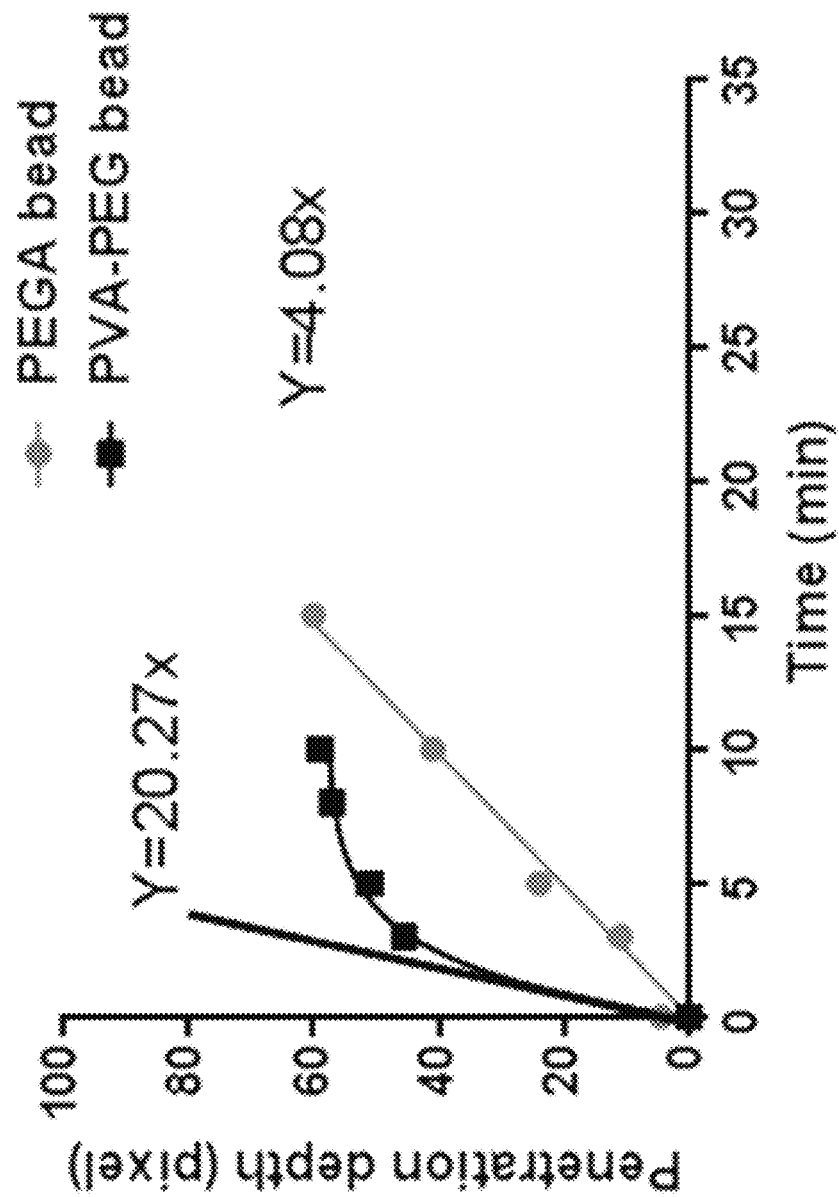
Figure 27D:
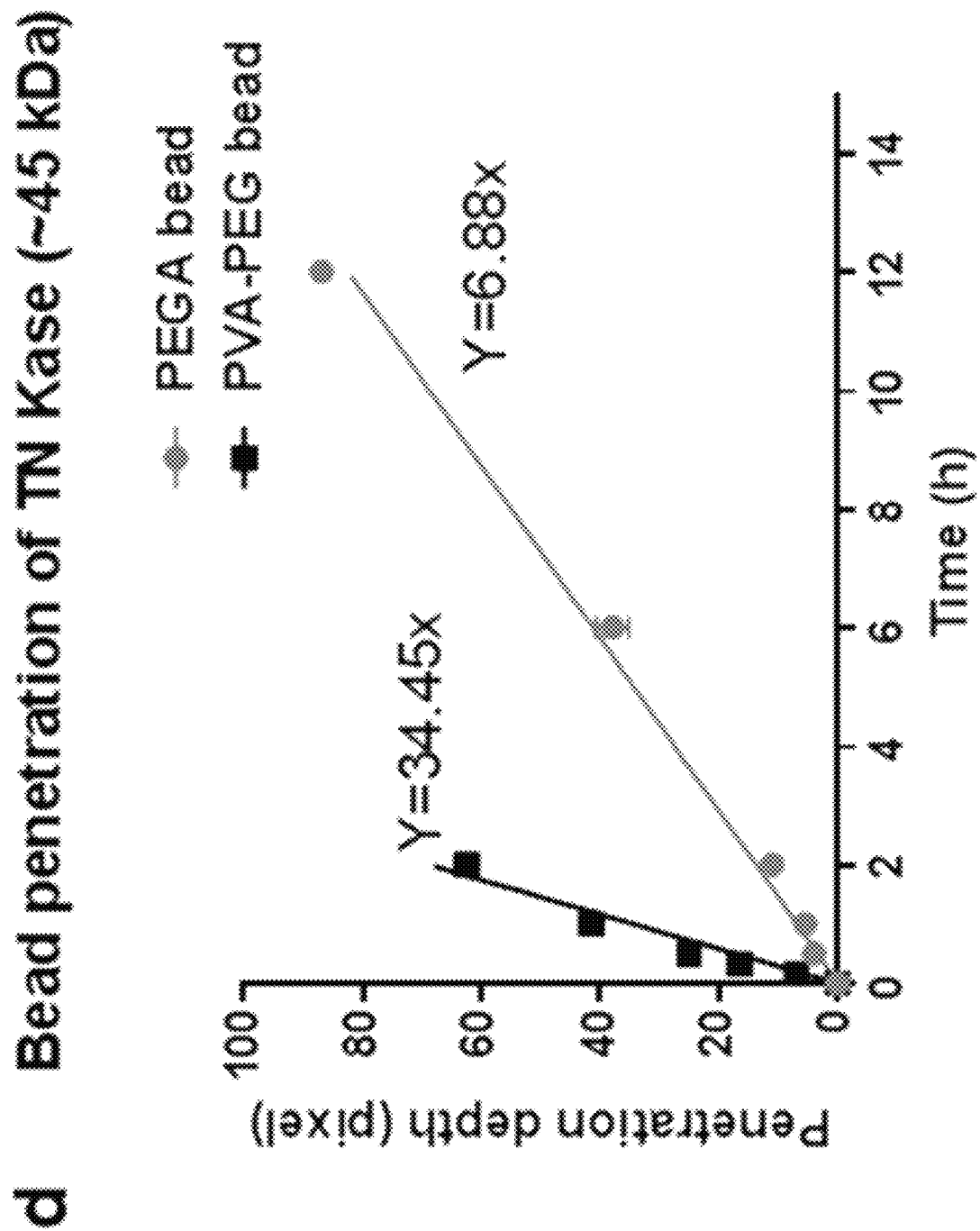

FIG. 27 shows kinetic penetration of proteins into PEGA and PVA-PEG resin, respectively. Trypsin (24 kDa) and TNKase (Tenecteplase) (45 kDa) were used as model proteins. a) Confocal fluorescent images of Trypsin penetration into PEGA and PVA-PEG resin. b) Kinetic penetration depth vs. time of Trypsin. c) Confocal fluorescent images of TNKase penetration into PEGA and PVA-PEG resin. d) Kinetic penetration depth vs. time of TNKase.

Figure 28:
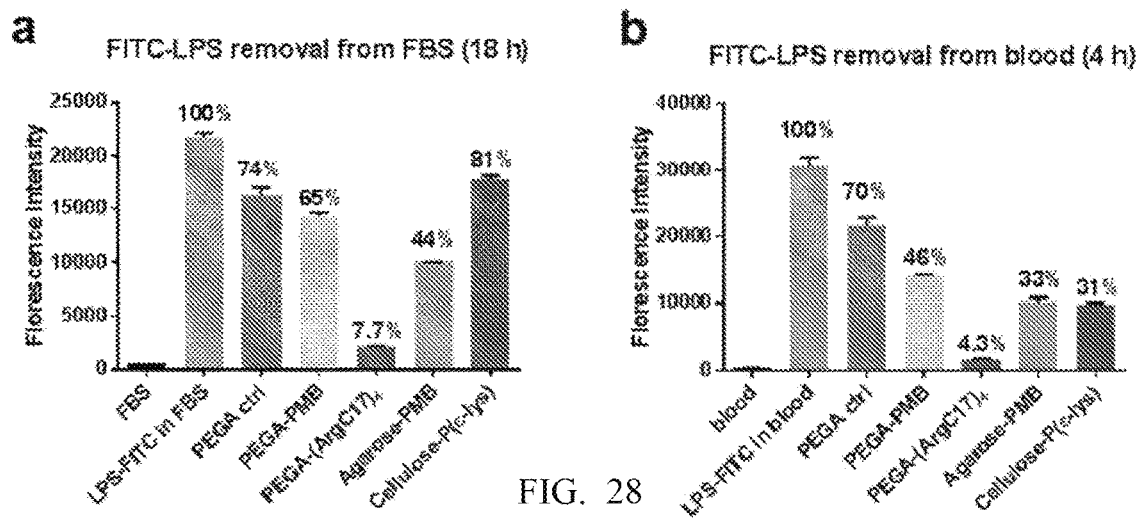

FIG. 28 shows removal efficiency of FITC-LPS at a high concentration (10 µg/mL) by nanotrap hydrogel resins in comparison with other sorbent resins from FBS a) and whole blood b) after 18 h and 4 h incubation, respectively.

Figure 29:
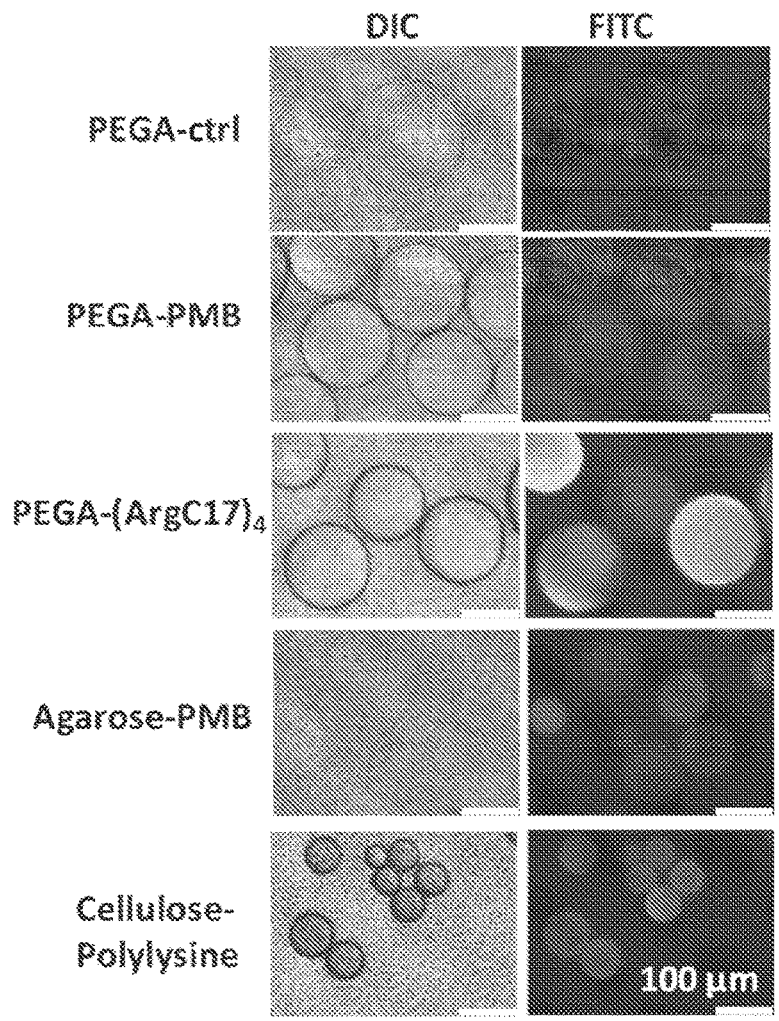

FIG. 29 shows fluorescent microscopy images showing the FITC-LPS removal by various resins from whole blood.

FIG. 30 shows a) MALDI-TOF MS analysis of the protein mixture solution of α-LA (0.5 mg/mL) and BSA (5 mg/mL) before and after incubation with PEGA-(ArgC17)$_4$ bead at bead/solution ratio of 1:10 (v/v) overnight: Significant reduction of α-LA by ~50% was observed relative to BSA, leading to the saturation of resin with protein and the capacity was calculated to be 13 µg α-LA/mg resin. b) The MALDI-TOF MS spectrum of proteins eluted from PEGA-(ArgC17)$_4$ resin by 6 M guanidine treatment: only α-LA was detected without observable BSA signals.

Figure 31:
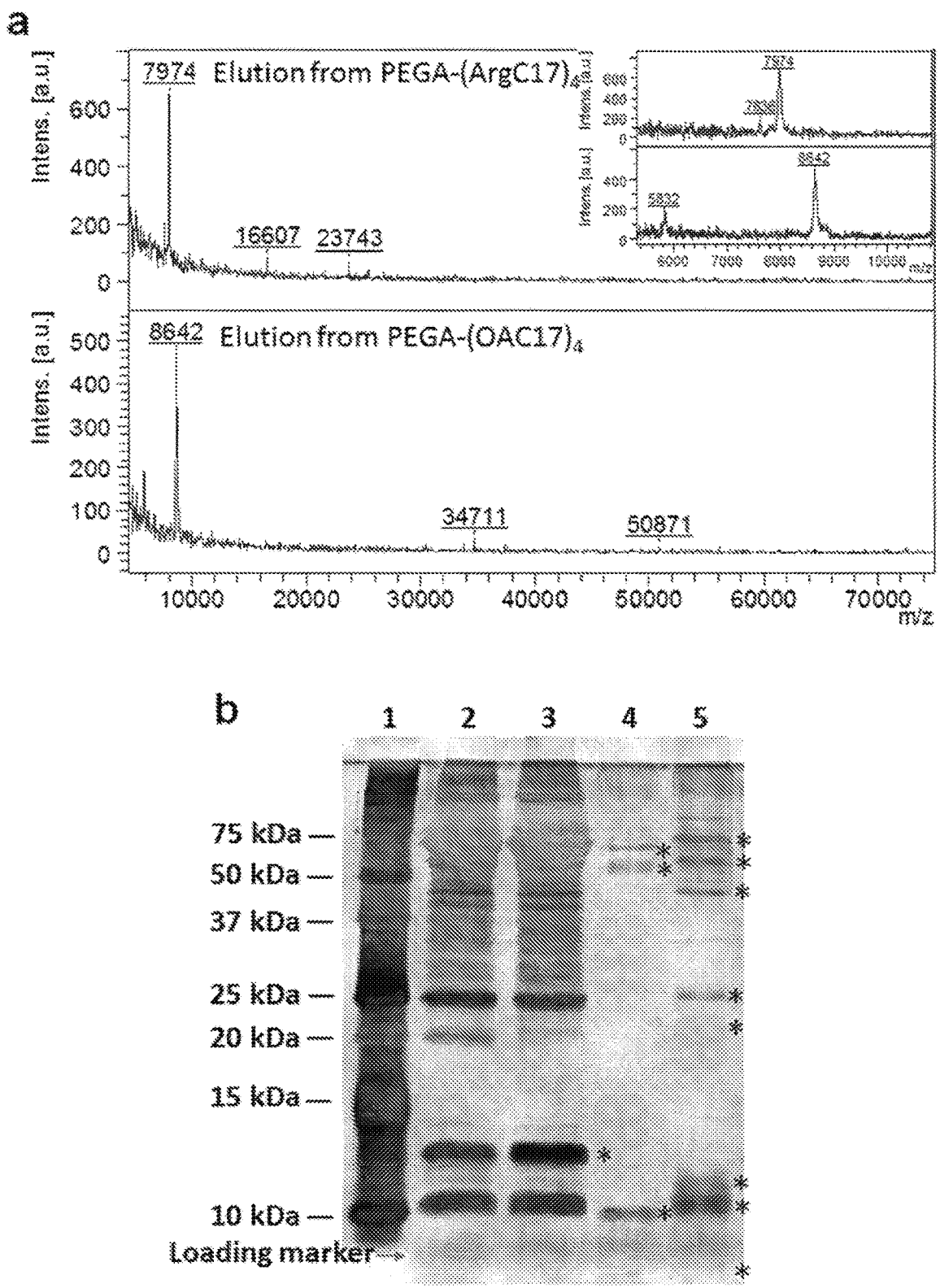

FIG. 31 shows a) adsorption profiles of both PEGA-(ArgC17)$_4$ and PEGA-(OAC17)$_4$ nanotrap resins from CLP-septic mice plasma detected by MALDI-TOF MS after 8 M urea elution. Different abundant serum proteins were detected at 7974 and 8642 m/z in the elution from positive PEGA-(ArgC17)$_4$ and negative PEGA-(OAC17)$_4$, respectively. b) Silver-staining of 20% SDS PAGE of septic plasma before/after bead treatments and 8M urea elution of adsorbed proteins from resins soaked in septic plasma: Lane 1: Protein ladder; Lane 2: Sham plasma (100×) dilution; Lane 3: Septic plasma (100×) dilution; Lane 4: Elution from PEGA-(ArgC17)$_4$ resin soaked with septic plasma and eluted by 8M urea; Lane 5: Elution from PEGA-(OAC17)$_4$ resin soaked with septic plasma and eluted by 8M urea. * marks the bands not shown or with significant intensity difference in the counterpart resin adsorption or the plasma samples.

FIG. 32 shows a) agarose gel electrophoresis profiles of DNA (from fish sperm) and BSA loading by telodendrimer (PEG$^{5k}$(Arg$_2$Rf)$_4$). b) Agarose gel electrophoresis profiles showing the attenuation of protoporphyrin IX (PPIX) by a series of telodendrimers.

Figure 33:
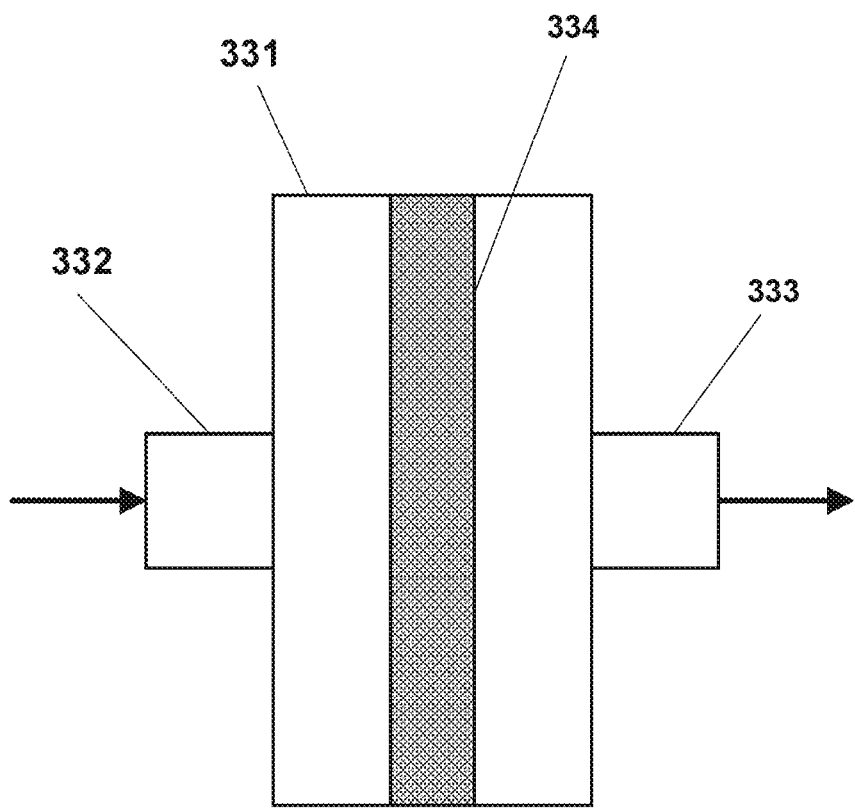

FIG. 33 shows a schematic of a device of the present disclosure. The device depicted is a guard column having a housing (331), an inlet (332), an outlet (333), and a sorption material of the present disclosure (334), where the arrows indicate the flow of a fluid through the device.

Figure 34:
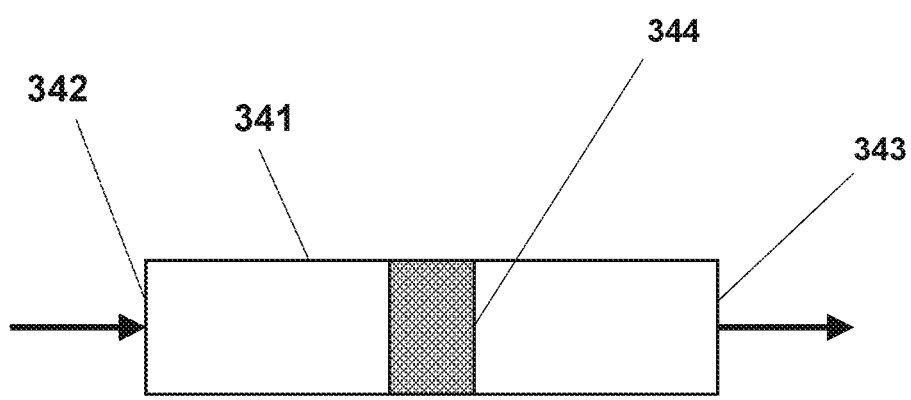

FIG. 34 shows a schematic of a device of the present disclosure. The device depicted is a guard column having a housing (341), an inlet (342), an outlet (343), and a sorption material of the present disclosure (344), where the arrows indicate the flow of a fluid through the device.

DETAILED DESCRIPTION OF THE DISCLOSURE

Although claimed subject matter will be described in terms of certain embodiments and examples, other embodiments and examples, including embodiments and examples that do not provide all of the benefits and features set forth herein, are also within the scope of this disclosure. Various structural, logical, process step, and electronic changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

As used herein, the term "protein" includes peptides (generally 50 amino acids or less), polypeptides (generally 100 amino acids or less), and proteins (greater than 100 amino acids). The protein may be a therapeutic protein (e.g., a cytotoxic protein or insulin). The protein may be an antibody, enzyme, or other bioactive protein.

As used herein, the term "moiety" refers to a part (substructure) or functional group of a molecule that is part of the telodendrimer structure. For example,

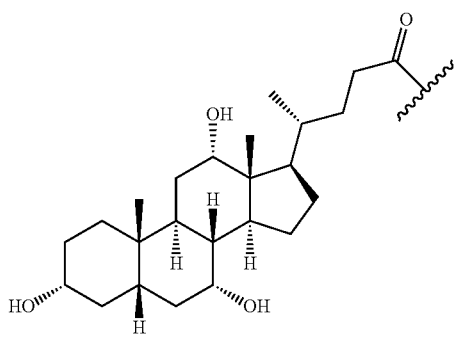

refers to a cholic acid moiety,

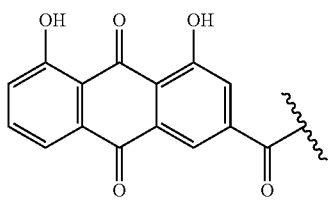 [SMILES: *C(=O)c1cc(O)c2c(c1)C(=O)c1cccc(O)c1C2=O]

refers to a rhein moiety,

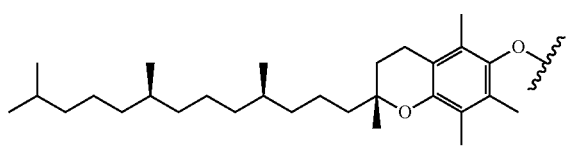 [SMILES: *Oc1c(C)c(C)c2c(c1C)CC[C@@](C)(CCC[C@H](C)CCC[C@H](C)CCCC(C)C)O2]

refers to a vitamin E moiety,

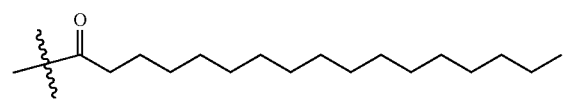 [SMILES: *C(=O)CCCCCCCCCCCCCCCC]

refers to a C17 moiety,

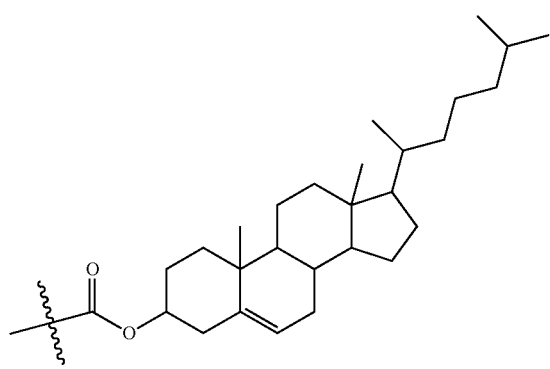 [SMILES: *C(=O)OC1CCC2(C)C(=CCC3C2CCC2(C)C(C(C)CCCC(C)C)CCC32)C1]

refers to a cholesterol moiety.

As used herein, the terms "dendritic polymer" or "dendritic polymer moiety" refer to branched polymers containing a focal point, a plurality of branched monomer units, and a plurality of end groups. The monomers are linked together to form arms (or "dendritic polymer moiety") extending from the focal point and terminating at the end groups. The focal point of the dendritic polymer can be attached to other segments of the compounds of the disclosure, and the end groups may be further functionalized with additional chemical moieties. The dendritic polymer can be composed of, for example, branched lysine and/or branched arginine moieties.

As used herein, the terms "monomer" and "monomer unit" refer to a diamino carboxylic acid, a dihydroxy carboxylic acid, or a hydroxyl amino carboxylic acid. Examples of diamino carboxylic acid groups of the present disclosure include, but are not limited to, 2,3-diamino propanoic acid, 2,4-diaminobutanoic acid, 2,5-diaminopentanoic acid (ornithine), 2,6-diaminohexanoic acid (lysine), (2-aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present disclosure include, but are not limited to, glyceric acid, 2,4-dihydroxybutyric acid, glyceric acid, 2,4-dihydroxybutyric acid, 2,2-bis(hydroxymethyl)propionic acid, and 2,2-bis(hydroxymethyl)butyric acid. Examples of hydroxyl amino carboxylic acids include, but are not limited to, serine and homoserine. One of skill in the art will appreciate that other monomer units can be used in the present disclosure. Monomers of the present disclosure can have a bond connectivity of, for example,

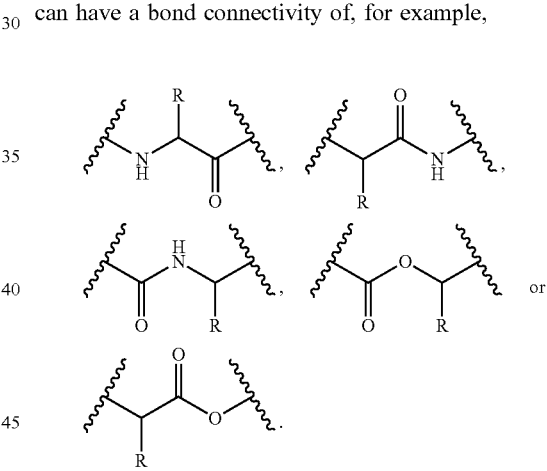

For example, when a monomer is defined as a lysine moiety, with a bond connectivity of A-Lys-B, where A and B are generic appendages, then it can be assumed that the structure can be any one of the following:

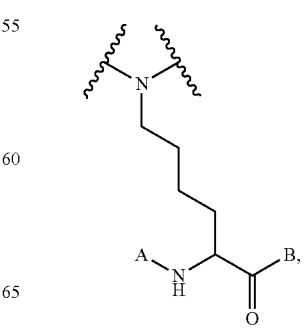

-continued

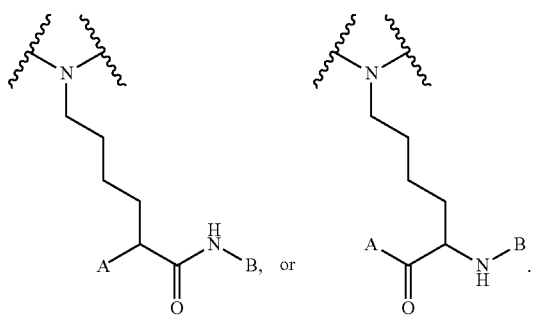

As used herein, the term "linker" of "spacer" refers to a chemical moiety that links (e.g., via covalent bonds) one segment of a dendritic conjugate to another segment of the dendritic conjugate. The types of bonds used to link the linker to the segments of the telodendrimers include, but are not limited to, amides, amines, esters, carbamates, ureas, thioethers, thiocarbamates, thiocarbonate, and thioureas. For example, the linker ($L^1$, $L^2$), individually at each occurrence in the telodendrimer, can be a polyethylene glycol moiety, polyserine moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety. The linker can also be a cleavable linker. In certain embodiments, combinations of linkers can be used. For example, the linker can be an enzyme cleavable peptide moiety, disulfide bond moiety or an acid labile moiety. One of skill in the art will appreciate that other types of bonds can be used in the present disclosure. In certain embodiments, the linker $L^1$ and $L^2$ can be

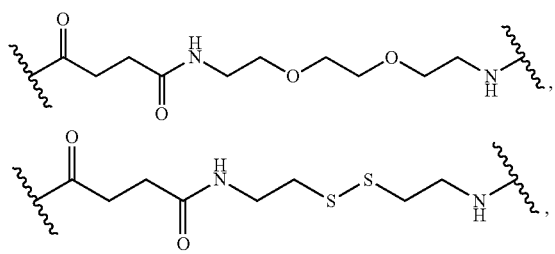

or a combination thereof, or other peptide sequence or spacer molecules.

As used herein, PEG group refers to a polyethylene glycol group or groups derived from polyethylene glycol. For example, the structure of PEG is

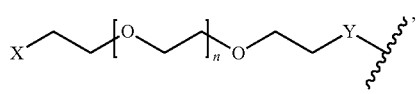

where X is selected from the group consisting of —NH$_2$, —OH, —SH, —COOH, —OMe, —N$_3$, —C═CH$_2$, and —≡CH, Y is selected from the group consisting of —C(═O)O—, —OC(═O)—, —OC(═O)NH—, —NHC(═O)—, —NHC(═O)O—, —NH—, —O—, —S—,

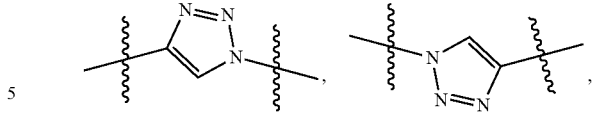

—N(PEG)-, —NHCOLys(PEG)-, —NHCO[branched Lys (PEG)]$_n$NH—, -Lys-, -Lys(PEG)-, -Lys(PEG)-Lys, -Lys (PEG)-Lys(PEG)-, Lys(PEG-Lys-Lys(PEG), and -Lys (PEG)-Lys(Lys(PEG)$_2$)-Lys- and n is the number of repeating unit in a range of 1 to 72736, including all integer values and ranges therebetween.

As used herein, the term "oligomer" or "oligomer moiety" refers to fifteen or fewer monomers, as described above, covalently linked together. The monomers may be linked together in a linear or branched fashion. The oligomer may function as a focal point for a branched segment of a telodendrimer.

As used herein, the term "hydrophobic group/moiety" refers to a chemical group/moiety that is water-insoluble or repelled by water. Examples of hydrophobic groups/moieties include, but are not limited to, long-chain alkanes and fatty acids, lipids, vitamins, natural compounds, herbal extracts, fluorocarbons, silicones, certain steroids such as cholesterol, bile acids, and certain polymers such as, for example, polystyrene and polyisoprene.

As used herein, the term "hydrophilic group/moiety" refers to a chemical group/moiety that is water-soluble or attracted to water. Examples of hydrophilic groups/moieties include, but are not limited to, alcohols, short-chain carboxylic acids, quaternary amines, sulfonates, phosphates, sugars, and certain polymers such as, for example, PEG, PVA.

As used herein, the term "amphiphilic compound" refers to a compound having both hydrophobic portions and hydrophilic portions. For example, the amphiphilic compounds of the present disclosure can have one hydrophilic part of the compound and one hydrophobic part of the compound, for example, bile acids, cholic acids, riboflavin, chlorogenic acid, and the like.

As used herein, the terms "treat", "treating" and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subject" refers to animals such, for example, as mammals. Suitable examples of mammals include, but are not limited to, primates (e.g., humans), cows, sheep, goats, horses, dogs, cats, rabbits, rats, mice, and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

The term "sorption material" in the context of this disclosure is to be understood as a material for performing a sorption, preferably an adsorption, i.e., molecules which are located in a biological fluid are fixed by the surface forces of the sorption material. In the description, the terms "adsorption agent" or "adsorbent" or "adsorber" are also used instead of the term "sorption material". According to the disclosure, the sorption material is provided for the adsorption of inflammation stimulating and/or mediating molecules (e.g., endotoxins and/or cytokines) from a biological fluid having of inflammation stimulating and/or mediating molecules (e.g., endotoxins and/or cytokines). The sorption material according to the disclosure is used above all in extracorporeal blood purification, in particular in patients having septic states.

The expression "biological fluid" used in the scope of the disclosure can relate to cell-free liquids, in particular blood plasma, or to liquids containing cells, in particular blood. Since it is also necessary in the course of extracorporeal blood purification to introduce other liquids, for example, solutions containing coagulation inhibitors (heparin solution, citrate solution) or substitution solutions (electrolytes, liquids to compensate for the liquid loss) into the extracorporeal blood circuit or into a blood plasma circuit, a biological fluid is also to be understood as diluted blood or diluted blood plasma. The present disclosure is primarily intended for the field of human medicine and therefore primarily relates to human biological fluids. However, this does not preclude the sorption materials, devices, and/or methods of the present disclosure of also being used in the field of veterinary medicine. In an example, biological fluids are bodily fluids.

The present disclosure provides sorption materials that bind to inflammation stimulating and/or mediating molecules. Sorption materials of the present disclosure can comprise telodendrimers, optionally attached to a substrate. The sorption materials of the present disclosure may be used as a component of a device. Methods of using sorption materials of the present disclosure include in vivo administration of the sorption material to a subject in need of or suspected of having a bacterial infection (e.g., systemic bacterial infection) and/or inflammation (e.g., systemic inflammation) and ex vivo contact of the sorption material with a fluid of the subject in need of or suspected of having a bacterial infection (e.g., systemic bacterial infection) and/or inflammation (e.g., systemic inflammation). Further described are methods of attenuating endotoxins, cytokines and DAMPs/PAMPs molecules, and the like in the blood of subjects diagnosed with sepsis and/or septic shock, and of subjects undergoing dialysis and methods of making antifouling surfaces.

In an aspect, the present disclosure provides sorption materials. The sorption materials comprise at least one compound (e.g., telodendrimers that are linear-dendritic copolymers having both charged moieties and binding moieties (e.g., LPS binding moieties) as end groups). Compounds (e.g., telodendrimers) may be attached to a substrate or stationary phase, such as a fiber, solid surface, hydrogel matrix, bead, particle (e.g., microparticles, nanoparticles, and the like), mat, membrane, or porous monolith, and may be attached to an external surface or to an internal surface of the substrate (i.e., the surface of a pore in, such as, for example, a porous fiber, bead or monolith).

In an aspect, the present disclosure provides sorption materials. The sorption materials may exhibit a dual mode of action to control hyperinflammation in sepsis. In an example, a sorption telodendrimer has one or more charged groups and one or more lipophilic and/or hydrophobic LPS binding group (LBM group(s)).

Sorption materials can have the following structure:

$R^1$-$L^1$-D-$(L^2$-$R^2)_{x,y}$  (Formula 1a)

S-$R^1$-$L^1$-D-$(L^2$-$R^2)_{x,y}$  (Formula 1b)

where $R^1$ and/or $L^1$ and/or $L^2$ are optional. In an example, sorption materials have at least one compound of formula 1a or a group derived therefrom. In an example, a sorption material having a substrate (e.g., S-$R^1$-$L^1$-D-$(L^2$-$R^2)_{x,y}$ has a plurality of compounds of formula 1a attached to the substrate (e.g., S-($R^1$-$L^1$-D-$(L^2$-$R^2)_{x,y})_n$, where n refers to the number of compounds on the substrate and is at least one).

For Formulas 1a and 1b: $R^1$ connects the telodendrimer (e.g., having the structure $L^1$-D-$(L^2$-$R^2)_{x,y}$) to the substrate. In an example, $R^1$ is a bond (e.g., a covalent bond). In an example, $R^1$ is a group that comprises the reaction product of two reacted functional groups. Non-limiting examples of reaction products include reaction products of Click reactions (e.g., triazoles and derivative thereof and the like), Michael additions, Diels-Alder reactions, amide bond formation reactions (e.g., amides), thio-maleimide additions, thio-ene additions, acylation reactions (e.g., esters and the like), and the like. Reactive groups, include, but are not limited to, hydroxyls, carboxylic acids, alkynes, azides, thiols, amines, acylhydrazines, maleimides, dienes, double bonds, biotin, peptides, proteins, and histidine tags. In an example, $R^1$ conjugates (e.g., a covalent bond between) a telodendrimer to a substrate (e.g., a solid substrate). In another example, $R^1$ is a reaction product linking a telodendrimer to a substrate (e.g., a solid substrate or hydrogel). In an example, $R^1$ is a terminal group (e.g., a reactive group that did not react). In an example, $R^1$ is a group that has an affinity for, and can therefore bind to, a substrate (e.g., a solid substrate or hydrogel). An affinity group is a ligand for a receptor (e.g., biotin, which a ligand for streptavidin, histidine tag, which is a ligand for nickel, and folic acid, which a ligand for a folate receptor). Examples of affinity groups include, but are not limited to, biotin, histidine tag, peptides, sugars, aptamer, small molecules (e.g., folic acid), and the like.

$L^1$ and $L^2$ are spacer molecules (e.g., spacer groups), which are also referred to herein as linker(s) or linker groups. Linker groups are optional. Examples of spacer molecules include, but are not limited to, oligo(ethylene glycol) moiety, polyserine moiety, enzyme cleavable peptide moiety, disulfide bond moiety and acid labile moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety. In an example, $L^1$ conjugates a telodendrimer to a solid substrate.

D is a dendritic polymer moiety having one or more branched monomer units, a plurality of end groups $R^2$, and optionally, one or more linker groups $L^2$. In an example, at each occurrence in the compound the branched monomer unit D is independently selected from the group consisting of a di- or tri-amino carboxylic acid moiety, a di- or tri-hydroxy carboxylic acid moiety, a hydroxyl amino carboxylic acid moiety, and the like.

R² are end groups of the dendritic polymer and are independently at each occurrence in the compound selected from the group consisting of charged moieties, LPS-binding moieties (LBMs), and combinations thereof. The charged moiety R² may be (or comprise or comprise moieties derived from) one or more positively or one or more negatively charged groups, including, but not limited to, $1^{st}$, $2^{nd}$, $3^{rd}$ and $4^{th}$ amine (e.g., primary, secondary, tertiary, or quaternary amines), charged amino acids (e.g., guanidine, arginine, and the like), imidazole, amidine, tetrazole, hydroxylamine; carboxyl, phosphate, sulfonate, methanesulfonamide, sulfonamide, or oxalic acid functional groups; the LBM R² end groups may be (or comprise moieties derived from): long-chain alkanes ($C_1$-$C_{50}$) (e.g., C17 as described herein) and fatty acids ($C_1$-$C_{50}$), aromatic molecules, esters, halogens, nitro compounds, anthracyclines, fluorocarbons, silicones, certain steroids such as, for example, cholesterol, terpenoids, vitamins (e.g., Vitamin E), and polymers (e.g., PLGA, polycaprolactone, polylactic acid, polyglycolic acid, polystyrene and polyisoprene, and polyvinyl pyridine), and groups derived therefrom.

x is the number of R² end groups that are charged moieties, and ranges from 1-32, and any integer value (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) and range therebetween. In examples, x is 4-8 (e.g., 4, 5, 6, 7, or 8), or from 4-16 (e.g., 4, 5, 6, 7, 8, 9, 10, 11, 12, 13, 14, 15, or 16), or from 6-12 (e.g., 6, 7, 8, 9, 10, 11, or 12), or from 8-16 (e.g., 8, 9, 10, 11, 12, 13, 14, 15, or 16), or from 4-32, or from 8-32. In an example, x equals 3, 4, 5, 6, 8, 12, 16, 24, or 32.

y is the number of R² end groups that are LBMs, and ranges from 1-32, and any integer value (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) and range therebetween. In examples, y ranges from 2-8 (e.g., 2, 3, 4, 5, 6, 7, or 8), or from 4-8 (e.g., 4, 5, 6, 7, or 8), or from 4-16 (e.g., 4, 5, 6, 7, 8, 9, 10, 11, 12, 13, 14, 15, or 16), or from 4-32, or y equals 2, 3, 4, 5, 6, 8, 12, 16 or 32. In various examples, the ratio of x:y is 1:1, 1:2, 2:1, 3:1, 3:2, or 4:1. In an example, x=8 and y=4. In an example, x=4 and y=4. In an example, x=8 and y=8. In an example, x=4 and y=8.

S is a substrate (e.g., a solid substrate or hydrogel network). A substrate is anything that can bind (e.g., covalent bond to) a compound (e.g., a telodendrimer). A substrate may be a solid substrate. In an example, the substrate is a hydrogel network, fiber, bead, particle, mat, membrane, porous monolith, or the like. Non-limiting examples of substrates include Rink resins, Tentagel resins, PVA-PEG resins, PEGA resins, polysaccharides beads (e.g., cellulose, agarose, alginate, dextran, hyluronic acid, pullulan, chitosan, pectin, and the like, and combinations thereof), synthetic or natural fibers, membranes or mats, PEG, peptides (e.g., aggregated peptides), proteins (e.g., aggregated proteins), polynucleic acids (e.g., aggregated polynucleic acids), silicon, metals, paramagnetic or magnetic particle, any material used in chromatography columns, and the like. The dendritic structure of 1(a) can be immobilized on the surface of a solid matrix (e.g., fibers or mat surface) or homogenously distributed in a porous resin or hydrogel matrix or beads (nano- or microparticles) via covalent bonds (e.g., bonds formed via click reactions, Michael additions, Diels-Alder reactions, amide bond formation reactions, thio-maleimide additions, thio-ene additions, and the like). The substrate may have a hydrophobic surface, hydrophilic surface, or a combination thereof. In an example, the solid substrate is porous. In an example, S is a porous carrier, where the pores are size-exclusion pores or hydrogel networks with a molecular weight cutoff of less than or equal to 50 kDa. In an example, where the substrate is one of or more of peptides, proteins, or polynucleic acids, the peptides, proteins, and/or polynucleic acids are crosslinked and/or aggregated such that the material is a supramolecular structure (e.g., fibril comprising a self-assembled (e.g., aggregated) peptide). In an example, a substrate has a plurality of groups formed from the reaction between one or more telodendrimers of the present disclosure and the substrate.

In an example, a sorption material comprises one or more compounds (e.g., telodendrimers) each compound having the structure of formula 1a or derivatives thereof.

Figure 3:
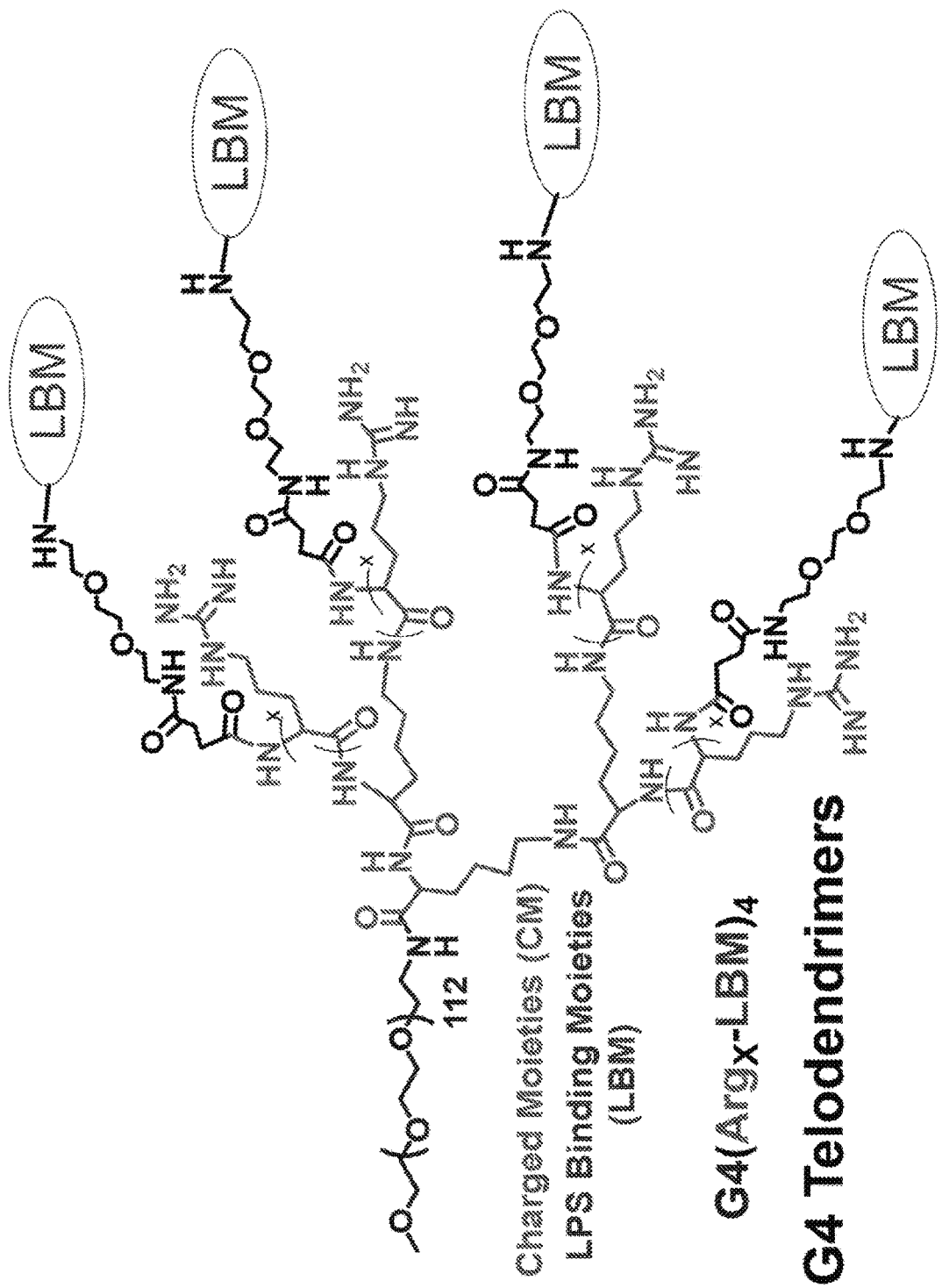
FIG. 3 shows structures of the representative LPS-binding G4 telodendrimers.

In an example, a compound of a sorption material is 1a-PEG-block-dendrimer (called telodendrimer). The structure is shown in FIG. 3, wherein the R¹ is a polyethylene glycol moiety (PEG), having a molecular weight of 44 Da to 100 kDa, including all Da values and ranges therebetween (examples of PEG-containing telodendrimers are provided in PCT patent application PCT/US2016/051266, the disclosure of which is incorporated herein by reference in its entirety).

Figure 4:
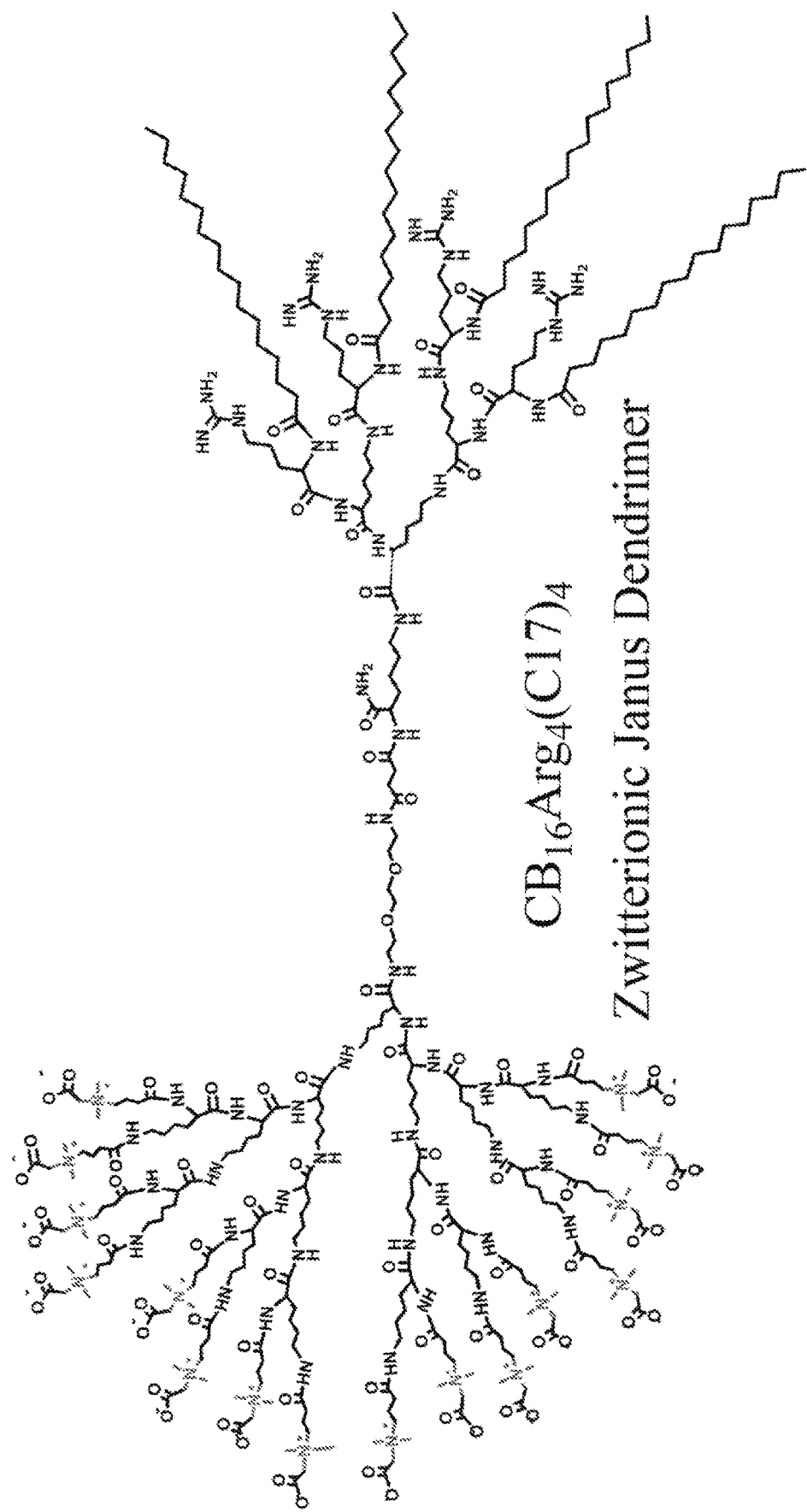
FIG. 4 shows structures of a representative zwitterionic LPS-binding Janus dendrimer $CB_{16}Arg_4(C17)_4$.

In an example, a compound of a sorption material is 1a-zwitterionic-dendrimer. The structure is shown in FIG. 4, wherein the R¹ is a zwitterionic group comprising one or more zwitterionic dendron, zwitterionic linear group (which can be formed from a zwitterionic linear compound or zwitterionic polymer), or a combination thereof (examples of zwitterionic telodendrimers and zwitterionic Janus dendrimers are provided in U.S. Pat. Appln. No. 62/464,892, the disclosure of which is incorporated herein by reference in its entirety).

In various examples, the backbone of the zwitterionic linear compounds and/or zwitterionic dendrimers are formed from amide bonds, ester bonds, ether bonds, or a combination thereof. In an example, the zwitterionic linear compounds are linear compounds comprising a linear polymer backbone comprising one or more pendant zwitterionic moieties/groups covalently bound to the polymer backbone (e.g., a linear polymer backbone comprising two or more branching monomers covalently bound to form a linear compound of branching moieties and one or more zwitterionic moieties groups covalently bound to a branching moiety or branching moieties). In an example, the branching monomer is lysine and the zwitterionic linear compound is linear polylysine with one or more zwitterionic moieties groups covalently bound to a lysine moiety or lysine moieties. The zwitterionic moieties/groups may be independently, at each occurrence in the compound, selected from the group consisting of carboxybetain groups/moieties (with one or two carbon spacers), glycerylphosphorylcholine groups/moieties, choline phosphate groups/moieties, sulfobetaines, ammoniosulfates, carboxytriazolium, and pyridiniosulfonate.

A zwitterionic linking group (ZLG) can be used to link a dendron (e.g., a zwitterionic dendron) to $L^1$ or D. The ZLG can have a terminal amino acid or terminal amino acid-$NH_2$ group (e.g., lysine group or terminal lys-$NH_2$ group). The ZLG can have a terminal group (e.g., an amine or amide group) that can be used to initiate dendrimer synthesis (e.g., a liquid phase dendrimer synthesis). In an example, the zwitterionic linking group (ZLG) has the following structure:

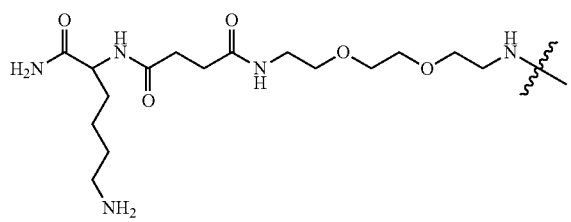 [SMILES: *NCCOCCOCCNC(=O)CCC(=O)NC(CCCCN)C(N)=O]

or an analog thereof.

In an example, the sorption material of the present disclosure has a desirable endotoxin sorption capacity and endotoxin sorption speed. The sorption materials of the present disclosure have a higher affinity for LPS than polymyxin B without its toxicity, which is unexpected. Having a high LPS affinity has therapeutic advantages, in particular for patients having sepsis, because a large volume of biological fluid can be freed of endotoxins in a short time. The survival chances of patients having severe sepsis may be improved by the sorption material of the present disclosure. As already noted, the speed of the endotoxin binding by the sorption agent may be important to the survival of the patient. The treatment duration in the scope of extracorporeal blood purification can also be shortened due to the sorption material of the present disclosure, whereby chronological, financial, human resources, and the like can be saved. In such an example, the sorption material comprises at least one compound having a structure of 1a, where $R^2$ is chosen from a combination of cholesterol-arginine, a combination of heptadecanoic acid-arginine, and a combination vitamin E-arginine, where x=8 and y=4 for each combination.

In an example, the sorption material of the present disclosure captures a broad range of inflammatory molecules, in addition to endotoxins. Non-limiting examples of inflammatory molecules include cytokines, inflammatory Damage-associated molecular patterns (DAMPs) and pathogen-associated molecular patterns (PAMPs) molecules through, such as, for example, the combination of charge and hydrophobic effects. Size exclusive effects of porous or hydrogel substrates enable inflammatory molecules to diffuse into the substrate and be captured by the compound attached to the substrate. Using size exclusive pores to scavenge inflammatory mediators and stimulators is effective relative to unimodal immune modulation therapies to control hyperinflammation for sepsis treatment.

Pathogen-associated molecular patterns (PAMPs) are molecular structures or molecules that are shared by most pathogenic bacteria and some viruses. Non-limiting examples of PAMPs include microbial nucleic acids, including, for example, DNA (e.g., unmethylated CpG motifs), double-stranded RNA (dsRNA), single-stranded RNA (ssRNA), 5'-triphosphate RNA, lipoproteins, surface glycoproteins, and membrane components (e.g., peptidoglycans, lipoteichoic acid, lipopolysaccharide (LPS), glycosylphosphatidylinositol, and the like), and the like.

Damage-associated molecular patterns (DAMPs) are endogenous molecules that are constitutively expressed and released upon tissue damage, resulting in activation of the immune system. Non-limiting examples of DAMPs include, high-mobility group box 1 (HMGB1), heat shock proteins (HSP), RNA and DNA, mitochondria, histones, interleukin-1α, heme, hyaluronan, and peroxiredoxin (PRDX), and the like.

Sorption materials of the present disclosure have a simple production, because the sorption materials of the disclosure are produced using peptide chemistry methods known in the art.

The pore size of the solid substrate (e.g., porous carrier) is affects the endotoxin adsorption. It is therefore desirable, also for reasons of reproducibility, if the solid substrate (e.g., porous carrier) has a defined mean pore size. The mean pore size of the carrier always relates to that before the attachment of the compound (e.g., telodendrimer).

In an example, the mean pore size can be tuned if the substrate (e.g., porous carrier) is produced from a synthetic polymer. Although a person skilled in the art in this field knows what the term "mean pore size of a polymer" is to be understood as and how the porosity or the mean pore size can be intentionally set, this term will nonetheless be briefly defined here for reasons of clarity. The mean pore size relates to the mean diameter of the pores. In a Gaussian size distribution of the pore diameters, the mean pore diameter is the pore diameter which corresponds to the maximum of the distribution curve. In various examples, the mean pore diameter is determined by one or more methods known in the art, such as, for example, mercury intrusion or nitrogen adsorption methods (e.g., as described in Weber et al. 2008. Neutral styrene divinylbenzene copolymers for adsorption of toxins in liver failure. Biomacromolecules 9(41322-1328)). The pore size of a polymer may be set by variation of one or more of the concentration of the participating monomers or co-monomers, the solvent, or the modulator. The smaller the pores of the polymer are selected to be, the larger the internal surface area of the polymer which is available for sorption, in particular adsorption. The larger the pores, it is expected the better the accessibility of the pores for larger molecules. Production methods for a synthetic, hydrophobic polymer of defined pore size, which can be used for the instant disclosure, are known in the art (e.g., Weber et al. 2008).

In an example, it has been shown that desirable inflammatory mediating and/or mediating molecules (e.g., endotoxin) sorption can be achieved by the sorption material if the substrate (e.g., carrier, such as, for example, a bead or polymer substrate) has a mean pore size of at least 15 nm. It is known in the art that a substrate preferably has a mean pore size of at least 30 nm. For clinical application of extracorporeal blood purification, however, it is favorable if the mean pore size of the uncoated carrier is not greater than 120 nm. The internal surface area of the sorption material would otherwise become too small; the result would be a reduction of the endotoxin sorption capacity (endotoxin adsorption capacity). In an example, a hard resin has a pore size of 300-500 µm, including every µm value and range therebetween.

In an example, the uncoated substrate has a mean pore size of approximately 80-100 nm, including all 0.1 nm values and ranges therebetween. In this variant, the elimination of endotoxins from a biological fluid occurs with desirable speed and efficiency. Only a small quantity of sorption agent is therefore required to bind a large quantity of endotoxin. For example, the concentration of this variant of the sorption agent according to the disclosure, when it is used as a suspension in an extracorporeal plasma circuit, can be selected as 1% (weight-percent volume-percent). An extracorporeal plasma circuit which contains a suspension of a sorption agent in the form of microparticles represents a central component of a Microspheres-based Detoxification System (MDS). An MDS is known in the art and found in EP 0776223 B and U.S. Pat. No. 5,855,782.

In addition, the form of the sorption material during the sorption procedure is also important. In an example, the sorption material of the present disclosure is in the form of microparticles. The particle size influences the kinetics of the adsorption. In addition, with a small particle size, there is a large surface area/volume ratio. In an advantageous subvariant, the microparticles have a particle size of 20 μm or less.

In an example, the microparticles are used in an MDS. The microparticles circulate as a suspension in a purification circuit (plasma circuit) on the filtrate side of a membrane filler. However, if the membrane filler leaks, the danger exists that microparticles will reach the extracorporeal blood circuit and then the body of the patient and will result in a lung embolism therein. For this reason, it is advantageous in a further subvariant if the microparticles have a particle size of 8 μm or less, preferably, 5 μm or less, since the danger of a lung embolism can be avoided at these small particle sizes.

In an aspect, the present disclosure provides molecular or nanoparticle (e.g., nanoparticles having a largest dimension, such as, for example, a diameter of 1-100 nm, including every nm value and range therebetween) compositions comprising sorption materials (e.g., sorption materials comprising compound 1a, and optionally, a substrate) of the present disclosure. Non-limiting examples of compositions include solutions, suspensions, emulsions, solid injectable compositions that are dissolved or suspended in a solvent before use, and the like. The injections may be prepared by dissolving, suspending or emulsifying one or more of the active ingredients in a diluent. Examples of diluents, include, but are not limited to distilled water for injection, physiological saline, vegetable oil, alcohol, and a combination thereof. Further, the injections may contain stabilizers, solubilizers, suspending agents, emulsifiers, soothing agents, buffers, preservatives, etc. The injections may be sterilized in the final formulation step or prepared by sterile procedure. The composition of the disclosure may also be formulated into a sterile solid preparation, for example, by freeze-drying, and can be used after sterilized or dissolved in sterile injectable water or other sterile diluent(s) immediately before use.

The compositions may include one or more pharmaceutically acceptable carrier. Pharmaceutically-acceptable carriers include, but are not limited to, sugars, such as lactose, glucose and sucrose; starches, such as corn starch and potato starch; cellulose, including sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The composition, if desired, can also contain minor amounts of wetting or emulsifying agents, or pH buffering agents. Additional non-limiting examples of pharmaceutically acceptable carriers can be found in: *Remington: The Science and Practice of Pharmacy* (2005) 21st Edition, Philadelphia, Pa. Lippincott Williams & Wilkins.

In an aspect, the present disclosure provides devices comprising one or more sorption materials of the present disclosure. Devices of the present disclosure can be used to remove inflammation stimulating and/or mediating molecules from a fluid (e.g., a biological fluid, such as, for example, a bodily fluid).

Sorption materials of the present disclosure are of particular use in extracorporeal blood purification (apheresis), such as for a subject who has or is suspected of having a systemic infection (e.g., systemic bacterial infection) (e.g., sepsis) (i.e., therapeutic use), systemic inflammation, and/or dysfunctional kidneys (e.g., subjects undergoing dialysis). Such blood purification may include the removal of inflammation stimulating and/or mediating molecules (e.g., endotoxins and/or cytokines).

In an example, the sorption agent can be used as a filler material for a sorption device. In various examples, a sorption device is implemented as a column or cartridge. Depending on which blood purification device or which blood purification method (e.g., hemoperfusion, plasmapheresis/plasmasorption and the like) is used, the sorption device can be situated on the blood side in an extracorporeal blood circuit or in a plasma circuit on the filtrate side. The biological fluid (e.g., blood or blood plasma) passes the sorption apparatus, the endotoxins binding to the immobilized sorption telodendrimers of the sorption agent. The purified blood or plasma is returned to the patient. Examples of sorption device configurations are known in the art. For example, the Cytosorb® cartridge from CytoSorbents Corporation is an example of a sorption apparatus already approved in Europe for extracorporeal absorption of cytokines; and the Toraymyxin from Spectral Medical Inc. is an extracorporeal direct hemoperfusion adsorption column incorporating polymyxin B covalently immobilized to polystyrene fibers which is approved in Japan and Europe for removing endotoxin in the bloodstream. The basic design, manufacture and use of such columns and cartridges is well known in the art, although all current sorption apparatus for endotoxin removal fall short in terms of therapeutic outcomes.

In an example, a device of the present disclosure comprises a housing defining an inlet and an outlet, where the inlet and the outlet are in fluid communication with one another, and the housing is configured such that the fluid enters the housing through the inlet and exits the housing through the outlet; and a sorption material is disposed in the housing (e.g., a sorption material bound to a substrate disposed in the housing), where the sorption material is a sorption material of the present disclosure.

In an example, the sorption material is bound to a substrate as described herein. The substrate is disposed on at least a portion of or all of a surface of the housing. For example, the sorption material is attached to the housing, in other examples, the sorption material is loose within the housing. In various examples, the sorption material is maintained within the housing by mechanical (e.g., size exclusion filter the sorption material cannot pass through), electrical, magnetic or other means.

Designing and building devices containing materials (e.g., sorbents) that selectively remove substances from liquids being passed through the device (e.g., columns, cartridges) is well known. Examples of devices are cartridges for removing toxins from serum for sepsis treatment (e.g., Cytosorb and Toraymyxim cartridges) or dialysis (e.g., Fresenius' Diasafe® plus and NxStage RRT and Chronic dialysis cartridges), filters to purify water (e.g., Brita, Woder 10K Gen3 In-Line Filter), columns for removing target substances from solutions (e.g., affinity chromatography columns). The techniques and designs used in the design of such prior art devices can be applied to the present disclosure. Various other form factors are known in the art.

In an example, the sorption material of the present disclosure is used in a plasma circuit, in which the sorption material is distributed as a suspension in the plasma. An example of such a plasma circuit is found as a device element in an above-described MDS. The sorption material provided in suspension in a plasma circuit is preferably in the form of microparticles.

Although the endotoxin sorption material according to the present disclosure is primarily provided for use in extracorporeal blood purification (apheresis), usage in chromatography is within the scope of the present disclosure. The sorption material can thus be used as a filler material for chromatography columns for purifying endotoxin-loaded blood or blood plasma. Other applications for removing endotoxins from biological fluids or water are also within the scope of the present disclosure. Specifically, any material that is or can be used as the stationary phase substrate in an affinity chromatography column and any material to which an antigen, antibody, enzyme, receptor, biomolecule, ligand, protein or nucleic acid can be bound, bonded, coupled or otherwise attached. FIG. 34 depicts a schematic of a chromatography column containing a sorption material of the present disclosure.

The sorption material of the present disclosure or a device containing a sorption material of the present disclosure or a plasma circuit containing a suspension of a sorption material of the present disclosure is particularly suitable for treating a sepsis.

In an example, a device of the present disclosure includes a device such as a cartridge for use in an apparatus, such as, for example, a guard column. FIG. 33 depicts a schematic of a guard column containing a sorption material of the present disclosure.

In various examples, a method is carried out using a device of the present disclosure.

In an aspect, the present disclosure provides methods using sorption materials and devices comprising sorption materials of the present disclosure. Methods of the present disclosure may involve administering a sorption material of the present disclosure to a subject in need of treatment who has been diagnosed with or is suspected of having a systemic bacterial infection (e.g., sepsis) (i.e., therapeutic use) and/or systemic inflammation, and/or passing a bodily fluid of the subject through a device comprising a sorption material of the present disclosure. A method can be carried out in a subject in need of prophylaxis for systemic bacterial infections/illnesses and/or systemic inflammation. Inflammation stimulating and/or mediating molecules of the present disclosure are associated with systemic bacterial infection and/or systemic inflammation. In a method of the present disclosure, one or more or all inflammation stimulating and/or mediating molecules bind to the sorption material of the present disclosure. In various examples, a method is carried out using a device of the present disclosure.

In an example, inflammation stimulating and/or mediating molecules (e.g., endotoxins, cytokines, and the like, and combinations thereof) are removed to a desirable degree and at desirable speed from a biological fluid using sorption materials of the present disclosure. The present disclosure also provides a sorption material that is non-toxic relative to polymyxin. The present disclosure provides methods for using such materials to remove endotoxins and inflammatory cytokines from biological fluids, particularly as a treatment for illness caused by such inflammation stimulating and/or mediating molecules (e.g., endotoxins, cytokines, and the like, and combinations thereof).

In an example, when an inflammation stimulating and/or mediating molecule binds to a sorption material of the present disclosure, the inflammation stimulating and/or mediating molecule is neutralized and cannot bind to anything aside from the sorption material.

In an example, inflammation stimulating and/or mediating molecules are endotoxins, lipopolysaccharides, cytokines, damage associated molecular patterns (e.g., gene molecules, HMGB1 protein, histone proteins, ATP, and the like, and combinations thereof), and the like, and combinations thereof. Inflammation stimulating and/or mediating molecule are often associated with sepsis. Methods of the present disclosure can be used to treat and/or ameliorate the symptoms of sepsis.

In an example, the systemic infection is caused by one or more bacteria, viruses, or fungi, or a combination thereof. Non-limiting examples of bacteria include *E. coli, P. aeruinosa, E. corrodens, Haemophilus influenza, S. aureus, Streptococcus* species, *Enterococcus* species and *Neisseria*, and the like, and combinations thereof.

In an example, systemic inflammation is caused by an external insults. Examples of external insults include, but are not limited to, traumas, burns, cardiac surgery, pancreatitis, CAR-T cancer immunotherapy, and the like, and combinations thereof.

The present disclosure provides in vivo and ex vivo methods of treating a subject having or suspected of having a systemic bacterial infection and/or systemic inflammation.

In an example, an in vivo method of the present method comprises administering to the subject in need of treatment a sorption material of the present disclosure and, optionally, isolating the sorption material bound to one or more or all of the inflammation stimulating and/or mediating molecules.

In an example, in an in vivo method of the present disclosure, a sorption material of the present disclosure may be bound to a solid substrate or hydrogel network. Suitable solid substrates include substrates described herein and those known in the art. Non-limiting examples of solid substrates include Rink resins, Tentagel resins, PVA-PEG resins, PEGA resins, Chemmatrix resins, porous adsorption resins, polysaccharide beads, synthetic or natural fibers, membranes, mats, peptides (e.g., aggregated peptides), proteins (e.g., aggregated proteins), polynucleic acids (e.g., aggregated polynucleic acids), silicon, metals, magnetic particles (e.g., paramagnetic particles), chromatographic materials, and combinations thereof. Such substrates may be porous and/or may have size-exclusion pores with a molecular weight cutoff of less than or equal to 50 kDa. In an example, hydrogel networks may have size-exclusion pores with a molecular weight cutoff of less than or equal to 50 kDa. Additionally, the sorption materials may have an $R^1$ as described herein.

In an example, one or more sorption material and/or one or more composition comprising one or more sorption material described herein is administered to a subject in need of treatment using any known method and route, including, but not limited to, oral, parenteral, subcutaneous, intraperitoneal, intrapulmonary, intranasal and intracranial injections. Parenteral infusions include, but are not limited to intramuscular, intravenous, intraarterial, intraperitoneal, and subcutaneous administration. Topical and/or transdermal administrations are also encompassed.

In an example, in an ex vivo method of the present disclosure, a biological fluid (e.g., a bodily fluid, such as, for example, blood, serum, culture media, or a combination thereof) of a subject in need of treatment of or suspected of having a systemic infection (e.g., systemic bacterial infection) and/or systemic inflammation is passed through a housing containing one or more sorption material of the present disclosure.

In an example, a biological fluid is passed through the inlet of the housing in which one or more sorption material of the present disclosure is disposed. The sorption material of the present disclosure is bound (e.g., covalently bonded) to a substrate that is disposed in the housing. The biological fluid contacts the sorption material and the biological fluid eventually exits the housing through the outlet of the housing. Upon contacting the sorption material, inflammation stimulating and/or mediating molecules may bind to the one or more sorption materials of the present disclosure. Suitable substrates include substrates described herein and those known in the art. Non-limiting examples of substrates include Rink resins, Tentagel resins, PVA-PEG resins, PEGA resins, Chemmatrix resins, porous adsorption resins, polysaccharide beads, synthetic or natural fibers, membranes, mats, peptides (e.g., aggregated peptides), proteins (e.g., aggregated proteins), polynucleic acids (e.g., aggregated polynucleic acids), silicon, metals, magnetic particles (e.g., paramagnetic particles), chromatographic materials, and combinations thereof. Such substrates may be porous and/or may have size-exclusion pores with a molecular weight cutoff of less than or equal to 50 kDa. In an example, hydrogel networks may have size-exclusion pores with a molecular weight cutoff of less than or equal to 50 kDa. The particle sizes of the filling substrate for whole-blood hemoperfusion use are 100-1000 μm, including all μm values and ranges therebetween. In an example, the particle sizes are 200-300 μm or 300-500 μm or 500-800 μm or 800-1000 μm, including all μm values and ranges therebetween for each stated range.

In an example, an ex vivo method is a method for removing, for example, endotoxins from a biological fluid, in which a biological fluid contaminated with, for example, endotoxins is brought into contact with the sorption material of the present disclosure. As described herein, the biological fluid can pass a sorption device which contains the sorption material. However, the sorption material can also be suspended in the biological fluid. An example of the latter is the above-described MDS. The biological fluid can be blood or blood plasma. In addition, because the sorption telodendrimers and sorption material are nontoxic, the sorption agent and/or sorption telodendrimers of the present disclosure can be added to blood intracorporeally to incapacitate or remove endotoxins and/or cytokines. In an example, in a method of the present disclosure, telodendrimers of the present disclosure are used to remove endotoxins (e.g., LPSs) without substantial or observable binding (e.g., removal) of one or more factors of the intracorporeal coagulation system such as, for example, protein C and protein S, and/or coagulation problems.

Additionally, the sorption materials may have an $R^1$ group chosen from polyethylene glycol groups (e.g., polyethylene glycol groups having a molecular mass of 5,000 Da), zwitterionic groups (e.g., polymers/oligomers of phosphoryl choline, polymers/oligomers of choline phosphates, polymers/oligomers of carboxybetaine, polymers/oligomers of sulfobetaine, and the like, and combinations thereof), and the like, and combinations thereof. $R^1$ groups are bound (e.g., covalently bonded) to the solid substrate.

In an example, a device of the present disclosure (e.g., a guard column/cartridge comprising a sorption material of the present disclosure) is used in conjunction with dialysis methods known in the art. A device of the present disclosure may be incorporated into a dialysis machine to, for example, remove exogenous endotoxins, cytokins, DAMPs/PAMPs, and the like, and combinations thereof.

In an aspect, the present disclosure provides a method to attenuate endotoxins, cytokines, DAMPs/PAMPs molecules, and the like, and combinations thereof in a fluid (e.g., a bodily fluid, such as, for example, blood, serum, and the like, and a combination thereof, or a culture medium). This includes, for example, the attenuation of endotoxins, cytokines and DAMPs/PAMPs molecules in the blood of subjects diagnosed with sepsis and/or septic shock, and of subjects undergoing dialysis.

In an example, a method to attenuate an endotoxin (e.g., a plurality of endotoxins that are the same or different) comprises a fluid (e.g., a bodily fluid) comprising endotoxins (e.g., a plurality of endotoxins that are the same or different) with a sorption material of the present disclosure, and incubating the fluid comprising endotoxins with the sorption agent, such that the endotoxin is attenuated.

Non-limiting examples of endotoxins that can be attenuated include, lipopolysaccharide (LPS), Lipoteichoic acid (LTA), and the like, and combinations thereof.

In an aspect, the present disclosure provides a method for making an antifouling surface.

In an example, a method to make an antifouling surfaces comprises: i) attaching a protecting group to a reactive group on at least a portion of an exterior surface of a substrate; ii) synthesizing or conjugating a sorption material of the present disclosure on at least a portion of an interior surface of the substrate, iii) removing the protecting group; and iv) conjugating antifouling materials to the exterior surface of the substrate, where the surface of the substrate is resistant to adhesion of cells and/or biomolecules.

Non-limiting examples of cells and/or biomolecules include red blood cell, white blood cells, platelet and other circulating cells; biomolecules include serum albumin, globulin, opsonin proteins, complement proteins, coagulating proteins and lipoapoproteins.

In an example, the sorption material used in the method to make an antifouling surface comprises an $R^1$ group chosen from polyethylene glycol groups (e.g., a polyethylene glycol group having a mass of 5,000 Da), a zwitterionic group (e.g., polymers/oligomers of phosphoryl choline, polymers/oligomers of choline phosphates, polymers/oligomers of carboxybetaine, polymers/oligomers of sulfobetaine, and the like, and combinations thereof), and the like, and combinations thereof.

In an example, the sorption material is bound to a first substrate that is disposed on a second substrate. The second substrate is the substrate upon which the method of making an antifouling surface is being performed. The first substrate is a solid substrate or hydrogel substrate as described herein.

The steps of the method described in the various embodiments and examples disclosed herein are sufficient to carry out the methods of the present disclosure. Thus, in an embodiment, the method consists essentially of a combination of the steps of the methods disclosed herein. In another embodiment, the method consists of such steps.

In the following Statements, various examples of the sorption materials and methods of using same are described:
Statement 1. A method for treating a subject having or suspected of having a systemic infection (e.g., systemic bacterial infection) and/or systemic inflammation (e.g., hemoperfusion) comprising contacting a biological fluid from the subject with at least one sorption material (e.g., where contacting comprises passing a fluid, such as, for example, a biological fluid, such as, for example, a bodily fluid through a housing, where the housing includes at least one inlet and at least one outlet, where the at least one inlet and the at least one outlet are in fluid communication with one another, and the housing is configured such that the fluid enters the housing through the inlet and exits the housing through the outlet, where at least one sorption material of the present disclosure is disposed in the housing) (e.g., where the sorption material comprises at least one compound bound to a substrate, where the compound has the following structure:

$$R^1\text{-}L^1\text{-}D\text{-}(L^2\text{-}R^2)_{x,y}$$

where $R^1$ is a bond or group attaching $L^1$ or D to the substrate; $L^1$ and $L^2$ independently at each occurrence are optional and are linker groups; D is a dendritic polymer moiety having one or more branched monomer units (X), and a plurality of end groups; $R^2$ independently at each occurrence is an end group of the dendritic polymer; x is the number of $R^2$ end groups that are charged moieties and ranges from 1-32, including all integer values (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) and ranges therebetween; and y is the number of $R^2$ end groups that are each independently a lipophilic moiety or a hydrophobic moiety and ranges from 1-32, including all integer values (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) and ranges therebetween, and where at least a portion of or all of the one or more of or all of inflammation stimulating and/or mediating molecules bind to the sorption material).

Statement 2. The method according to Statement 1, where the biological fluid is blood, serum, culture media, or a combination thereof.

Statement 3. The method according to Statement 1 or Statement 2, where $R^1$ is a polyethylene glycol group.

Statement 4. The method according to any one of the preceding Statements, where the substrate is a hydrogel network or solid substrate (e.g., a fiber, bead, particle, mat, membrane, porous monolith, or the like).

Statement 5. The method according to Statement 4, where the solid substrate is porous.

Statement 6. The method according to any one of the preceding Statements where the systemic infection (e.g., systemic bacterial infection) is caused by *E. coli*, *P. aeruinosa*, *E. corrodens*, *Haemophilus influenza*, *S. aureus*, *Streptococcus* species, *Enterococcus* species and *Neisseria* and/or the systemic inflammation is caused by trauma, burn, cardiac surgery, pancreatitis or CAR-T cancer immunotherapy.

Statement 7. A device for removing inflammation stimulating and/or mediating molecules from a fluid (e.g., a biological fluid) (e.g., hemoperfusion) comprising: a housing defining an inlet and an outlet, where the inlet and the outlet are in fluid communication with one another, and the housing is configured such that the fluid enters the housing through the inlet and exits the housing through the outlet; and a sorption material of the present disclosure is disposed in the housing, (e.g., where the sorption material comprises at least one compound bound to a substrate, where the compound has the following structure:

$$R^1\text{-}L^1\text{-}D\text{-}(L^2\text{-}R^2)_{x,y}$$

where $R^1$ is a bond or group attaching $L^1$ or D to the substrate; $L^1$ and $L^2$ independently at each occurrence are optional and are linker groups; D is a dendritic polymer moiety having one or more branched monomer units (X), and a plurality of end groups; $R^2$ independently at each occurrence is an end group of the dendritic polymer; x is the number of $R^2$ end groups that are charged moieties and ranges from 1-32 (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32), including all integer values and ranges therebetween; and y is the number of $R^2$ end groups that are each independently a lipophilic moiety or a hydrophobic moiety and ranges from 1-32 (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32), including all integer values and ranges therebetween).

Statement 8. A sorption material comprising at least one compound, optionally, bound to a substrate, (e.g., a sorption material of the present disclosure, where the compound has the following structure:

$$R^1\text{-}L^1\text{-}D\text{-}(L^2\text{-}R^2)_{x,y}$$

where $R^1$ is a bond or group attaching $L^1$ or D to the substrate; $L^1$ and $L^2$ independently at each occurrence are optional and are linker groups; D is a dendritic polymer moiety having one or more branched monomer units (X), and a plurality of end groups; $R^2$ independently at each occurrence is an end group of the dendritic polymer; x is the number of $R^2$ end groups that are charged moieties and ranges from 1-32, including all integer values (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) and ranges therebetween; and y is the number of $R^2$ end groups that are each independently a lipophilic moiety or a hydrophobic moiety and ranges from 1-32 (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32), including all integer values and ranges therebetween).

Statement 9. The sorption material according to Statement 8, where the sorption material is capable of binding inflammation stimulating and/or mediating molecules.

Statement 10. The sorption material according to Statement 8 or Statement 9, where the inflammation stimulating or mediating molecules are chosen from endotoxins, LPSs, cytokines, damage associated molecular patterns, and combinations thereof.

Statement 11. The sorption material according to any one of Statements 8-10, where the compound preferentially binds to the LPS, endotoxins, cytokines, or a combination thereof over albumin and/or globulin.

Statement 12. The sorption material according to any one of Statements 8-11, where $R^1$ is chosen from polyethylene glycol group/moiety, a zwitterionic group/moiety, or a combination thereof.

Statement 13. The sorption material according to any one of Statements 8-12, where the zwitterionic group/moiety is chosen from polymers/oligomers of phosphoryl choline, polymers/oligomers of choline phosphates, polymers/oligomers of carboxybetaine, polymers/oligomers of sulfobetaine, analogs thereof, and combinations thereof.

Statement 14. The sorption material according to any one of statements 8-13, where the substrate is a hydrogel network or solid substrate (e.g., a fiber, bead, particle, mat, membrane, porous monolith, or the like).

Statement 15. The sorption material according to Statement 14, where the solid substrate is chosen from Rink resins, Tentagel resins, PVA-PEG resins, PEGA resins, Chemmatrix resins, porous adsorption resins, polysaccharide beads, synthetic or natural fibers, membranes, mats, peptides (e.g., aggregated peptides), proteins (e.g., aggregated proteins), polynucleic acids (e.g., aggregated polynucleic acids), silicon, metals, magnetic particles, PEG, chromatographic materials, and combinations thereof.

Statement 16. The sorption material according to Statement 15, where the magnetic particles are paramagnetic particles.

Statement 17. The sorption material according to any one of Statements 8-16, where the compound is homogenously disposed on the substrate.

Statement 18. The sorption material according to any one of Statements 8-17, where the solid substrate is porous.

Statement 19. The sorption material according to Statement 18, where at least a portion of the hydrogel network or solid substrate has size-exclusion pores with a molecular weight cutoff of less than or equal to 50 kDa.

Statement 20. The sorption material according to any one of Statements 8-19, where the compound is bound to the solid substrate via a covalent bond.

Statement 21. The sorption material according to any one of Statements 8-20, further comprising a pharmaceutically acceptable carrier.

Statement 22. A method for treating a subject having or suspected of having a systemic infection (e.g., systemic bacterial infection) and/or systemic inflammation, comprising administering to the subject a sorption material of the present compound (e.g., a sorption material comprising at least one compound, where the compound has the following structure:

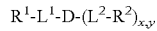

where $R^1$ is a bond or group attaching $L^1$ or D to the substrate; $L^1$ and $L^2$ independently at each occurrence are optional and are linker groups; D is a dendritic polymer moiety having one or more branched monomer units (X), and a plurality of end groups; $R^2$ independently at each occurrence is an end group of the dendritic polymer; x is the number of $R^2$ end groups that are charged moieties and ranges from 1-32, including all integer values (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) and ranges therebetween; and y is the number of $R^2$ end groups that are each independently a lipophilic moiety or a hydrophobic moiety and ranges from 1-32, including all integer values (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) and ranges therebetween, where at least a portion of or all of the one or more of or all of inflammation stimulating and/or mediating molecules bind to the sorption material).

Statement 23. The method according to Statement 22, where the sorption material further comprises a pharmaceutically acceptable carrier.

Statement 24. The method according to Statement 22 or Statement 23, where the sorption material is bound to a solid substrate.

Statement 25. The method according to any one of Statements 22-24, where the inflammation stimulating and/or mediating molecules are chosen from endotoxins, lipopolysaccharides, cytokines, damage associated molecular patterns, and combinations thereof.

Statement 26. The method according to Statement 25, where the damage associated molecular patterns are chosen from gene molecules, HMGB1 protein, histone proteins, ATP, and combinations thereof.

Statement 27. The method according to any one of Statements 22-26, further comprising isolating the compound bound to one or more of or all of the inflammation stimulating and/or mediating molecules.

Statement 28. The method according to any one of Statements 22-27, where the systemic infection (e.g., systemic bacterial infection) is caused by E. coli, P. aeruinosa, E. corrodens, Haemophilus influenza, S. aureus, Streptococcus species, Enterococcus species and Neisseria, and/or the systemic inflammation is caused by trauma, burn, cardiac surgery, pancreatitis or CAR-T cancer immunotherapy.

Statement 29. A method for attenuating endotoxins, cytokines, DAMPs/PAMPs, and the like, and combinations thereof in a fluid comprising: i) contacting a fluid comprising endotoxins with a sorption material of the present disclosure (e.g., a sorption material comprising at least one compound, where the compound has the following structure:

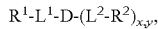

where $R^1$ comprises an end group; $L^1$ and $L^2$ independently at each occurrence are optional and are linker groups; D is a dendritic polymer moiety having one or more branched monomer units (X), and a plurality of end groups; $R^2$ independently at each occurrence is an end group of the dendritic polymer; x is the number of $R^2$ end groups that are charged moieties and ranges from 1-32, including all integer values (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) and ranges therebetween; and y is the number of $R^2$ end groups that are each independently lipophilic moieties or hydrophobic moieties and ranges from 1-32, including all integer values (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) and ranges therebetween; and ii) incubating the fluid comprising endotoxins with the sorption agent; where the endotoxin is attenuated).

Statement 30. The method according to Statement 29, where the endotoxin is chosen from lipopolysaccharide (LPS), Lipoteichoic acid (LTA), and combinations thereof.

Statement 31. A method for making an antifouling surface comprising: i) attaching a protecting group to a reactive group on at least a portion of an exterior surface of a substrate; ii) synthesizing or conjugating a sorption material of the present disclosure on at least a portion of an interior surface of the substrate (e.g., a sorption material comprising at least one compound, where the compound has the following structure:

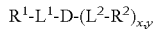

where $R^1$ comprises an end group; $L^1$ and $L^2$ independently at each occurrence are optional and are linker groups; D is a dendritic polymer moiety having one or more branched monomer units (X), and a plurality of end groups; $R^2$ independently at each occurrence is an end group of the dendritic polymer; x is the number of $R^2$ end groups that are charged moieties and ranges from 1-32, including all integer values (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) and ranges therebetween; and y is the number of $R^2$ end groups that are each independently lipophilic moieties or hydrophobic moieties and ranges from 1-32, including all integer values (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) and ranges therebetween; iii) removing the protecting group; and iv) conjugating antifouling materials to the exterior surface of the substrate, where the surface of the substrate is resistant to adhesion of cells and/or biomolecules).

Statement 32. The method according to Statement 31, where the antifouling material is chosen from polyethylene glycol, a zwitterionic material, or a combination thereof.

Statement 33. The method according to Statement 32, where the zwitterionic material is chosen from polymers/oligomers of phosphoryl choline, polymers/oligomers of choline phosphates, polymers/oligomers of carboxybetaine, polymers/oligomers of sulfobetaine, derivatives thereof, and combinations thereof.

Statement 34. The method according to any one of Statements 31-33, where the reactive group is chosen from amines, hydroxyls, thiols, azides, alkynyls, carboxylic acids, hydroxylamines, and combinations thereof.

The following examples are presented to illustrate the present disclosure. They are not intended to limiting in any matter.

Example 1

This example provides synthesis of use of sorption materials of the present disclosure.

In this example, the sorption material of the present disclosure bound lipopolysaccharides (LPS) through the combination of both charge and lipophilic or hydrophobic interactions (endotoxins are lipopolysaccharides in the cell wall of gram-negative bacteria and are released by cell lysis). Both the charged and lipophilic or hydrophobic groups of the telodendrimers (e.g., their geometry, structure and density) was tailored based on the structure of LPS to optimize the LPS-binding affinity. An electrophoresis assay revealed that the telodendrimers showed stronger binding affinity to LPS than the nonspecific protein bindings. They also show stronger LPS-binding affinity in comparison to polymyxin B (PMB), an antibiotic which is currently the gold standard of LPS-binding compounds. These telodendrimers attenuate LPS in vitro to prevent LPS by stimulating macrophage cells and decreasing proinflammatory cytokine production (e.g., TNF-α). Because these materials are non-toxic, they may be used to remove LPS systemically by IV injection of the sorption material into the bloodstream of a patient to bind and attenuate LPS activity spontaneously, therefore decreasing inflammation reactions in sepsis patients. In addition, these LPS-binding moieties can be conjugated in a size-exclusive hydrogel resin for extracorporeal removal of LPS from the blood of a severely septic patient. In addition, small-sized cytokines can also be absorbed and removed by these resins, which restrict large-sized serum proteins from competing for the active binding sites within the polymer resins by size exclusion. The simultaneous removal of both LPS and cytokines, as well as proinflammatory DAMPs/PAMPs molecules may improve the treatment of severe septic patients and save more lives together.

Figure 6:
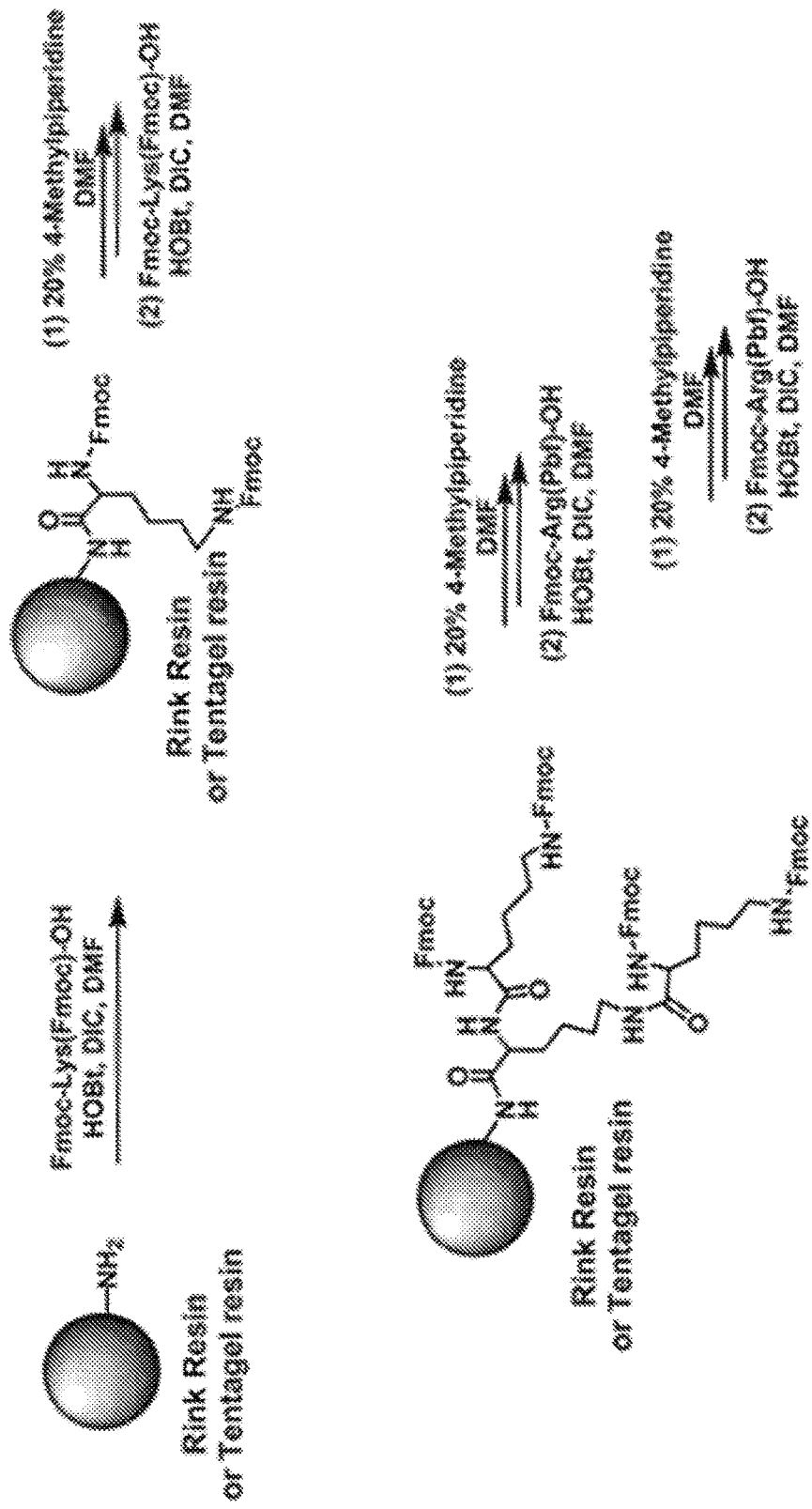
FIG. 6 shows a synthetic route for the solid phase supported LPS-binding dendron and the cleavage into solution from Rink resin.
Figure 6:
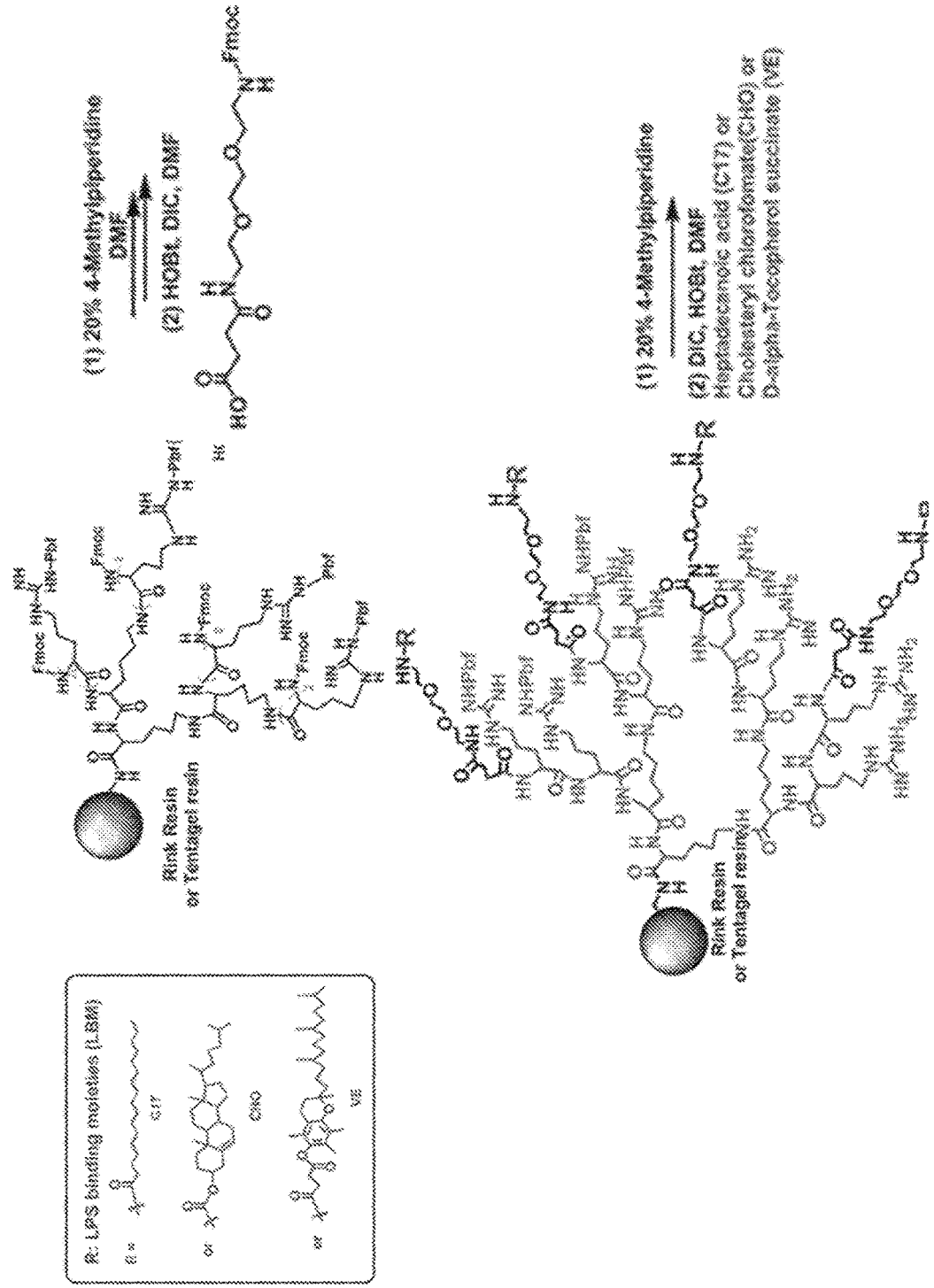
Figure 6:
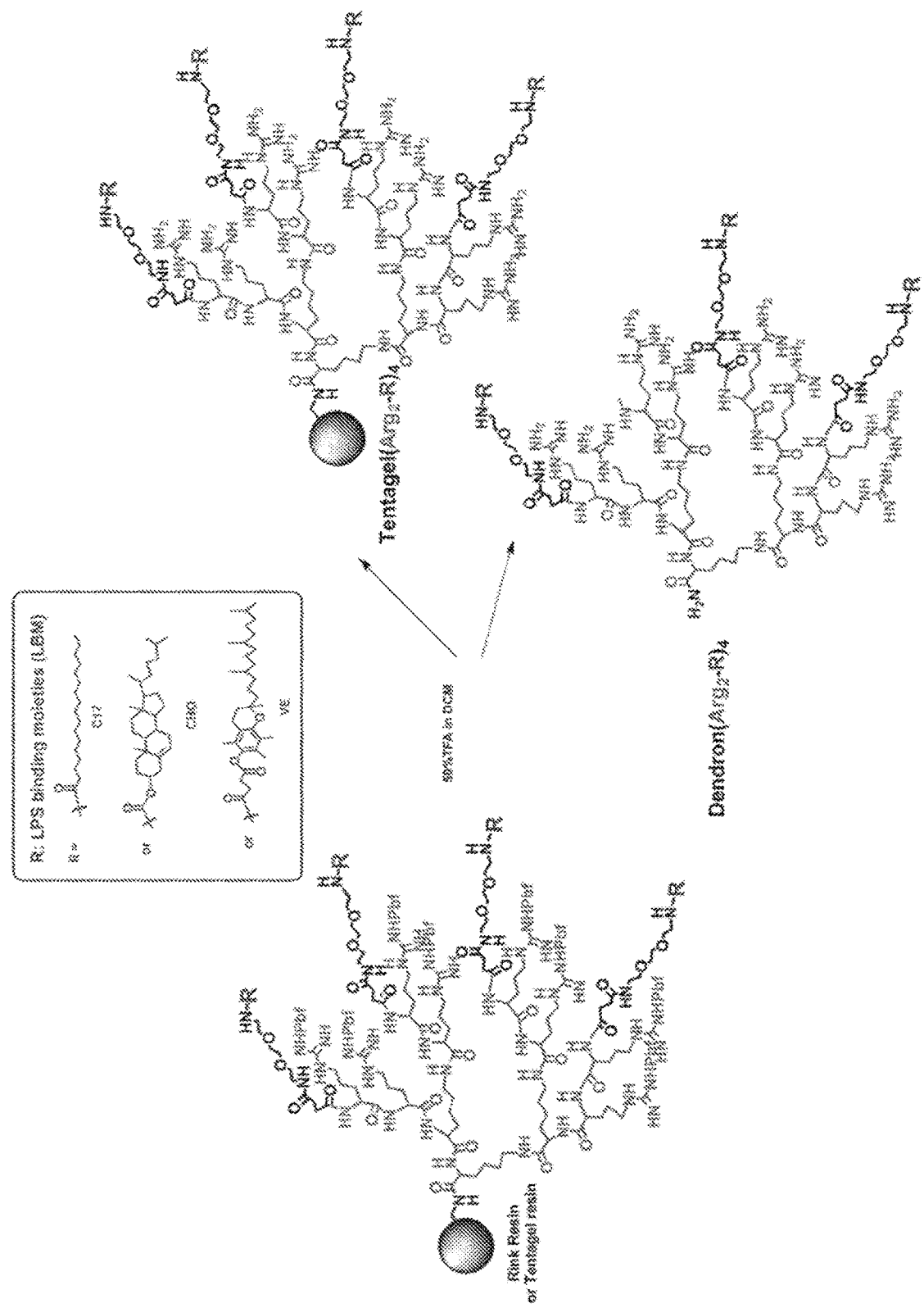

Solid phase synthesis of LPS-binding dendrons (FIG. 6). Starting from Rink amide resin (0.59 mmol/g) or Tentagel resin (0.24 mmol/g), (Fmoc)-Lys(Fmoc)-OH and Fmoc-PEG-COOH linker, were coupled sequentially following the standard Fmoc peptide synthesis procedures (FIG. 6). All reactants were in 3-fold excess with respect to the amine functional group on resin. After second generation dendritic oligolysine synthesis, (Fmoc)-Lys(Dde)-OH or (Fmoc)-Lys(Boc)-OH will be used to introduce the outer ($3^{rd}$) layer of oligolysine on acid sensitive Rink resin and acid stable Tantagel resin, respectively, to introduce the orthogonally protected amine groups for charge and hydrophobic moiety conjugation. DIC/HOBt were used as coupling reagents. Fmoc protection was removed by the treatment of resin with 20% 4-methylpiperidine solution in DMF for 30 min. Dde group was removed by the treatment of 2% hydrazine in DMF for 10 min. Boc protecting group was removed by the treatment of 50% TFA in DCM for 30 min. After the completion of each step reaction, residual reactants were removed under filtration and washed three times with copious solvents of DMF, DCM, and MeOH sequentially. Positively charged Arginine or lysine were conjugated onto the α-amino position of lysine after de-Fmoc procedure. The LPS-binding hydrophobic building blocks were conjugated on the γ-amine on the peripheral lysine after de-Boc or de-Dde protecting groups after the insertion of a triethyleneglycol linker molecule via standard peptide synthesis procedure.

Both LPS-binding dendron were synthesized on Rink and Tentagel resin and were treated with TFA/TIS/$H_2O$ (95/2.5/2.5, v/v/v) cocktail to cleave the protecting groups off the lysine or arginine group, at the same time to cleave the whole dendron from Rink resin into solution. In parallel, LPS-binding dendron on Tentagel resin are ready for LPS adsorption and removal. Alternatively, Tentagel can be replaced with any type of hydrophilic resins, such as, for example, PEGA resin, PVA-PEG resin, functionalized polysaccharide resin and the fibers as a solid support.

Figure 7:
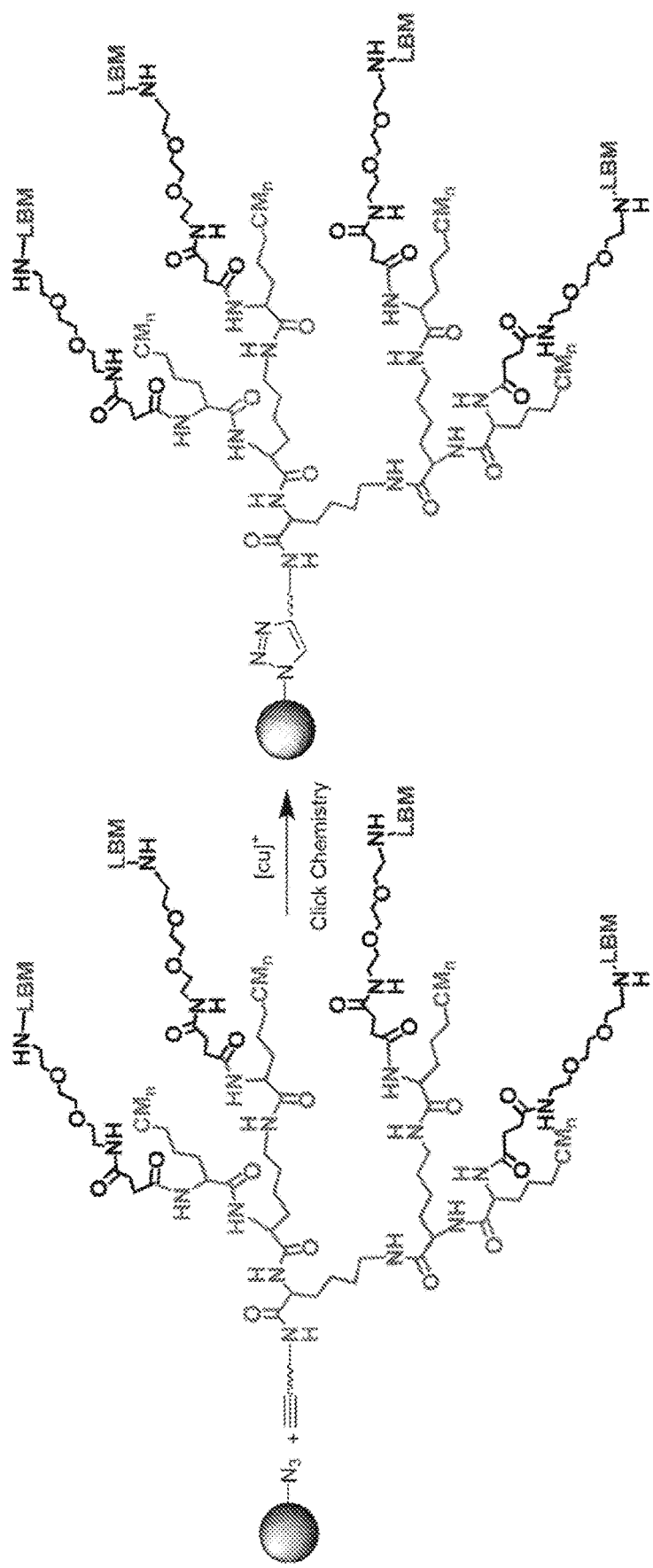
FIG. 7 shows conjugation of LPS-binding dendron to a solid matrix via Click Chemistry between azide and alkyne functional groups.

Conjugation of LPS-binding dendron onto a solid matrix (FIG. 7). Hydrogel resin or membranes, fibers made from synthetic or natural polymers can be chemically modified to introduce a functional group, such as, for example, a carboxylic acid, azide, alkyne, amine, double bond or thiol groups. The LPS-binding dendron can be synthesized on Rink resin and a complimentary reactive functional groups can be introduced prior to the focal point of the dendron, which is integrated as a reactive functionality with the dendron cleaved from Rink resin. As shown in FIG. 7, an alkynyl-functionalized dendron can be immobilized on a solid support decorated with azide groups via a $[Cu]^+$ catalyzed Click chemistry in aqueous or organic solvents, such as, for example, DMF.

Figure 5:
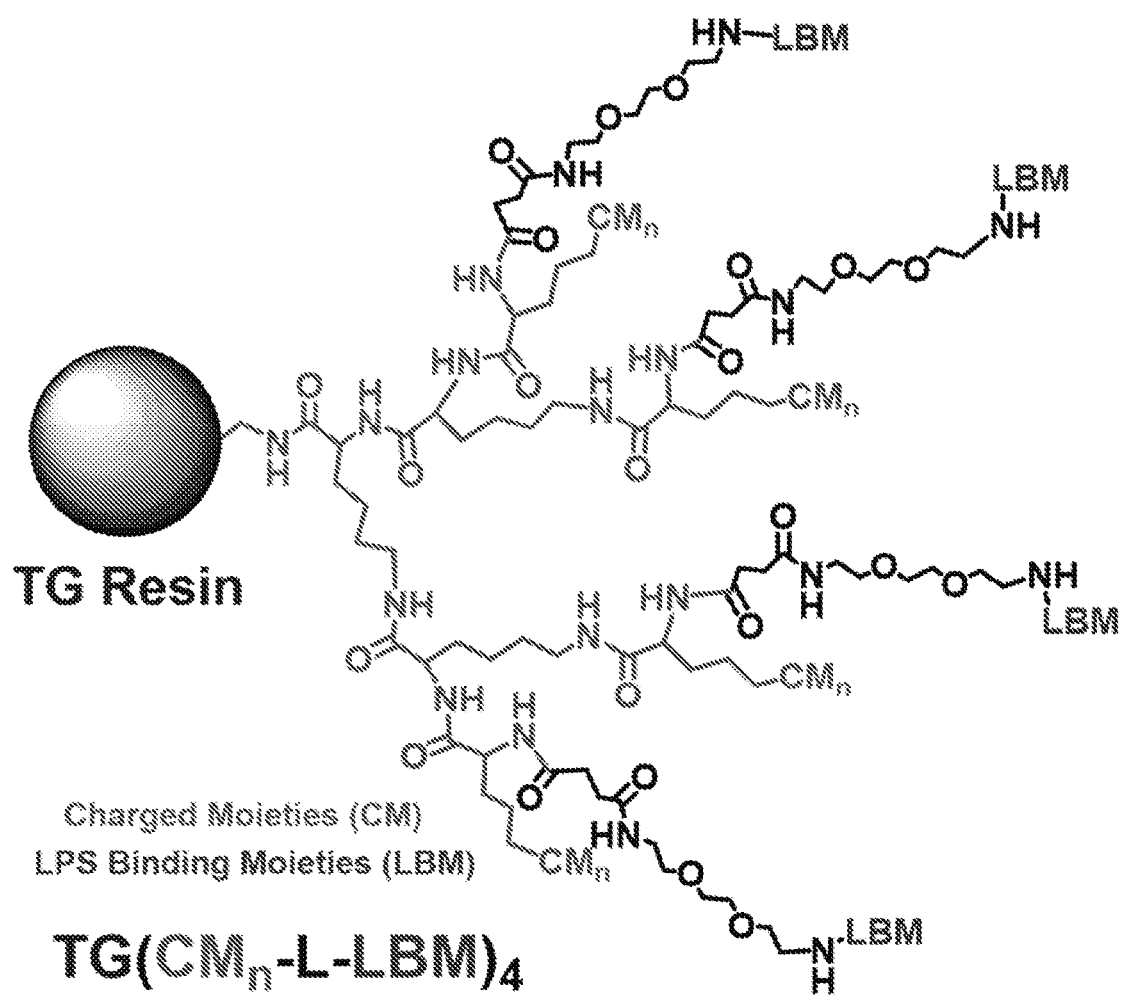
FIG. 5 shows solid resin supported dendritic LPS binding moieties.

Structure-based design and synthesis of telodendrimers. Charge optimization: a series of positive charge moieties (CMs) (FIGS. 1 & 5) can be introduced onto the dendritic peripheral on TG resin with vitamin E (VE) as effective LPS binding moieties as demonstrated in our previous studies. The beads were incubated with FITC-LPS at 10 μg/mL (CAC of LPS: 13 μg/mL) in the presence of PMB for short incubation to increase stringency of screening to identify one or two most efficient CMs.

Figure 8:
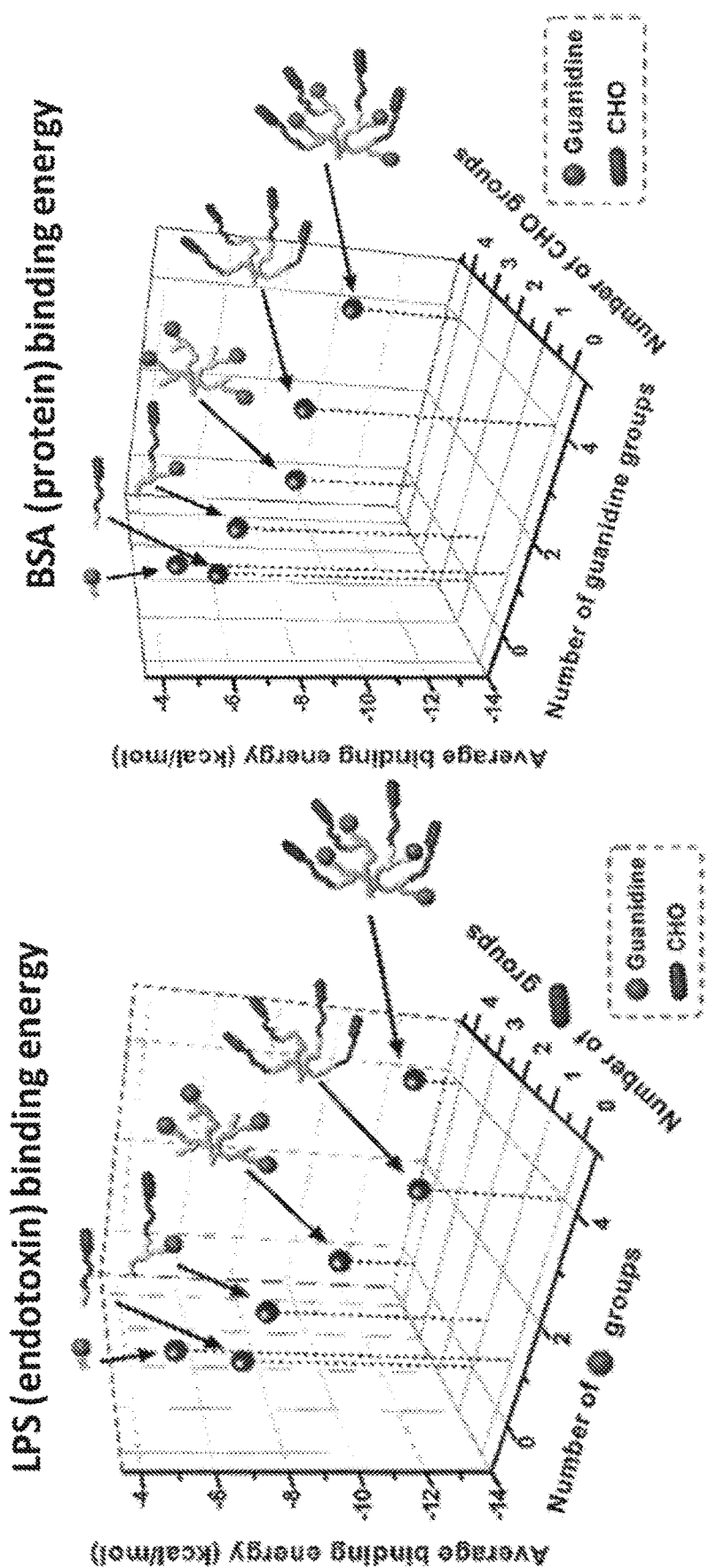
FIG. 8 shows docking energies of G4 dendron subunits with LPS and BSA respectively. It indicates that G4 telodendrimer binds LPS more favorably than BSA binding.

Virtual screening: In order to increase the accuracy of ranking in virtual screening, five stable conformations of LPS obtained from five individual molecular dynamic (MD) simulations were used to screen library compounds for LPS binding as shown in FIG. 8. A library of natural compounds (n=100) compiled in our previous study for drug-specific nanocarrier design will be further enriched (n=200) for LPS docking by including abundant and available hydrophobic natural compounds to match lipid A structure (e.g., fatty acids, abundant lipids, terpenes/terpenoids, hydrophobic vitamins, biogenic small molecules, and herbal extracts recorded in Pubchem database, and the like). The top 20 LBMs ranked consistently in five individual docking studies will be selected for G4 telodendrimer synthesis.

Electrophoresis Assays. The binding capacities of the telodendrimers with LPS and/or BSA were studied and compared with PMB binding using electrophoresis assay. The electrophoresis was carried out in 1.5% agarose gel (tris-borate-EDTA (TBE) buffer) at constant current of 20 mA for 2 h. The gel was imaged by a Bio-Rad Universal Hood II Imager (Bio-Rad Laboratories, Inc.) under SYBR Green modes or photographed under UV illumination.

On-bead binding assays. To perform the on-bead binding assay, the desired amount of resin bead was weighed, hydrated, and incubated with dye-labeled biological molecules (BSA and LPS) in PBS for defined time period. Then, the incubation solutions were removed and the beads were washed with PBS for three times. BSA-RB and/or LPS-FITC bound beads were then visualized under fluorescence microscope.

Spectroscopic characterization. Transmission electron microscopy (TEM) characterization of nanoparticle was performed on a JEOL JEM-1400 operated at 80 kV. Samples were prepared by applying aliquots of a nanoparticle solution on a glow discharged carbon-coated copper grids (CF300-CU, 300 mesh, Electron Microscopy Sciences). Negative staining was achieved using uranyl acetate solution (1%). The hydrodynamic sizes of nanoparticles were acquired by dynamic light scattering (DLS) using particle analyzer (Microtrac) equipped with equipped with 780 nm laser diode.

Figure 1:
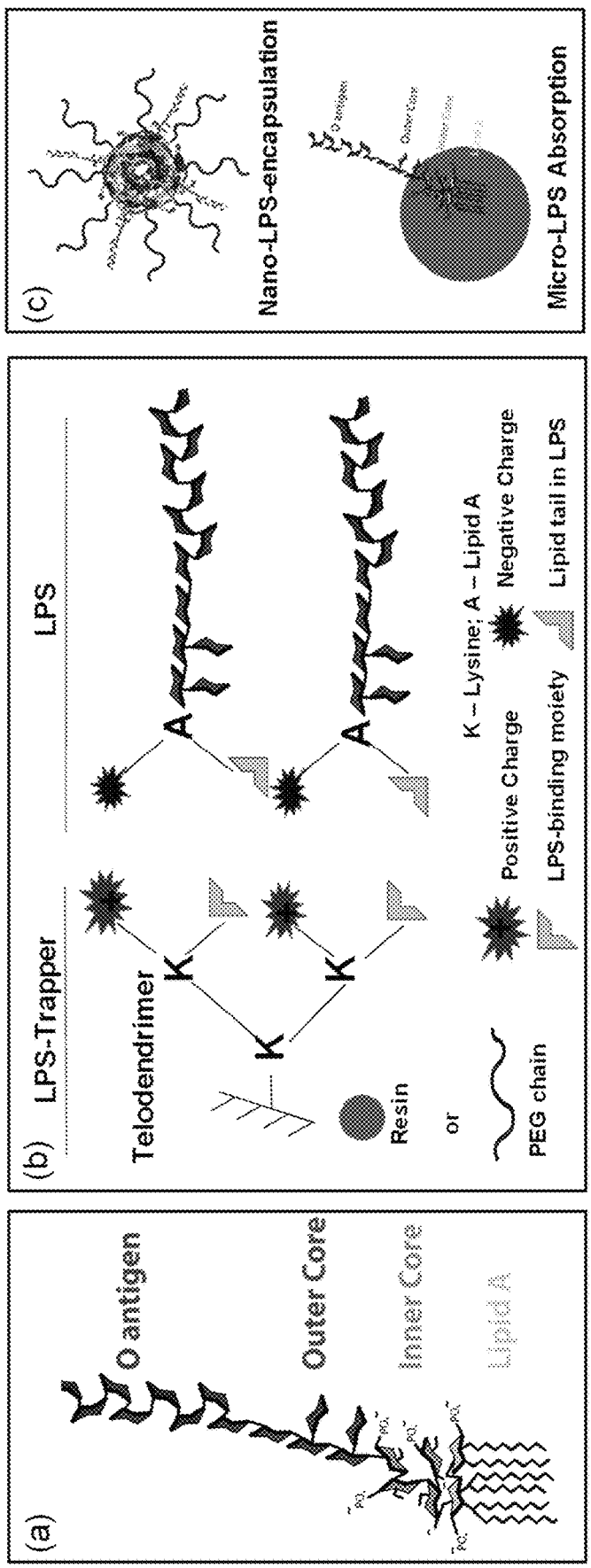
FIG. 1 shows (a) a diagram showing the structure of LPS. (b) Design of LPS-trapper by mapping both the charge and hydrophobic structures of lipid A in LPS for efficient LPS binding. (c) Models for LPS-encapsulation in telodendrimer nanoparticle and the LPS-absorption in the resin immobilized with telodendrimers.

Structure of lipopolysaccharide (LPS). LPS, also known as lipoglycans and endotoxins, consist of a lipid A and a polysaccharide composed of O-antigen, outer core and inner core joined by a covalent bond (FIG. 1). LPS is found in the outer membrane of Gram-negative bacteria, and elicit strong immune responses in animals. Lipid A is, in normal circumstances, a phosphorylated glucosamine disaccharide decorated with multiple fatty acids. These hydrophobic fatty acid chains anchor the LPS in and immobilize it on the bacterial membrane, and the rest of the LPS projects from the cell surface. The lipid A domain is responsible for part of the toxicity of Gram-negative bacteria. When bacterial cells are lysed by the immune system, fragments of membrane containing lipid A are released into the circulation, causing fever, diarrhea, and possible fatal endotoxic shock (also called septic shock). The Lipid A moiety is a very conserved component of the LPS. The significant negative charges and hydrophobic fatty acid chains also provide a strong anchor for molecular recognition for LPS binding/attenuation for sepsis treatment.

Rational design of a versatile nanocarrier for selective LPS binding. A well-defined PEGylated-dendritic system (named Generation 1 or G1 telodendrimer) for efficient anticancer drug delivery was previously developed. Novel hybrid G2 and functional-segregated G3 telodendrimers have been further developed by introducing drug binding moieties (DBM) identified by structure-based virtual screening to increase drug affinity within nanocarriers. The specific architecture design and the unique amphiphilic cholic acid (CA) ensures the stability and dispersability of nanocarriers bearing different DBMs. Further, a G4 telodendrimer for protein/peptide delivery was designed by introducing precisely both charges and hydrophobic protein binding molecules (PBMs) to fine-tune the protein binding affinity in sub-30 nm micelles. It was found that multivalent and synergistic combination of optimal charge and hydrophobic interactions is essential for efficient protein delivery. Therefore, G4 telodendrimer can be engineered for cytokine capturing.

Compared to the heterogeneous protein surface, lipid A has a well-defined structure with distinct charges and hydrophobic alkyl chains, which serves as a uniformed template for precise G4-telodendrimer design. Desirable charges and hydrophobic fragments can be introduced at the right proximity and density by the aid of computational approaches to fine-tune LPS binding moieties (LBMs) to the lipid A domain (FIG. 1). As shown in FIG. 3, G4 telodendrimers with four or eight positively charged arginines and different hydrophobic groups have been prepared for LPS binding. The biocompatible PEG outer shell of telodendrimer micelle sequesters its charges and hydrophobic domains and the lipid A region of LPS (FIG. 1) in nanoparticle, promising to reduce non-specificity and toxicity such as that encountered in the use of PMB for systemic LPS attenuation. Lipoteichoic acid (LTA), together with peptidoglycane, causes gram-positive bacteria sepsis. LTA has a similar lipid structure to lipid A. G4 telodendrimers and G4 telodendrimer micelles are desirable for attenuating LTA in addition to LPS. The replacement of PEG with zwitterionic carboxylic betaine in G4 telodendrimer results in a Janus dendrimer for LPS binding (FIG. 4).

Molecular Docking Assays. As shown in FIG. 8, the binding energies of the G4 dendritic fragments with BSA and LPS increase with the increased valence and the combination of charge and hydrophobic interactions. Four branched $(ArgCHO)_4$ binding to LPS is stronger than LPS' binding to BSA, with a ~2 kcal/mol lower docking energy. Interestingly, it was found that an increased number of hydrophobic cholesterol (CHO) didn't alter the telodendrimer's binding energy with BSA—e.g., CHO vs. ArgCHO vs. $CHO_4$. In contrast, tetramer $CHO_4$ binds LPS more strongly than CHO, indicating ample opportunities for hydrophobic interactions in binding with LPS with its large and clustered hydrophobic lipid A domain. In comparison, BSA may only have smaller hydrophobic surface/cavities, which can't accommodate an increased number of hydrophobic CHO of the $CHO_4$ telodendrimer for multivalent interactions.

Efficient telodendrimer nanocarrier for LPS binding. A flexible linker can be inserted between the charged moieties (e.g., arginine) and hydrophobic domains (e.g., CHO, VE) in the G4 telodendrimer to match lipid A structure. As shown in FIG. 9, LPS can aggregate into large 25~50 nm nanoparticles as observed under TEM, which were reported to be >100 nm in the literature. G4 telodendrimer $PEG^{5k}Arg_4VE_4$ form small micelles measured by both DLS and TEM analysis. After LPS loading, telodendrimers formed LPS-$G4(ArgVE)_4$ micelles (1:4 n/n)<25 nm in size, as observed under TEM (FIG. 9).

Electrophoresis assays. Agarose native gel electrophoresis was used to characterize LPS and BSA loading efficiency in G4 telodendrimer micelles, based on the charge and size effects. As shown in FIG. 10*a*, free rhodamine B-labeled BSA (RB-BSA) and FITC-labeled LPS (FITC-LPS) migrate down due to the negative charge and small sizes. After loaded in G4 micelles, their size becomes large and their charges are neutralized, which leads to the entrapment of LPS and BSA in the loading vials. Both LPS and BSA can be efficiently encapsulated in nanoparticles formed by $G4(ArgVE)_4$ telodendrimers at a 1:4 molar ratio. Even with an increase of the amount of BSA in the LPS-BSA mixture by a factor of five, providing five times as much BSA to compete with LPS for loading into the telodendrimers nanoparticles, LPS is still stably loaded into the $G4(ArgVE)_4$ nanoparticles. Some BSA can be trapped in the nanocarrier, indicated by the overlapping of red and green signal in the vial yielding yellow color (FIG. 10*a*). Extra RB-BSA leaks out from the loading well with the increasing concentration of BSA. Polymyxin B is known to bind LPS strongly in vitro and in vivo. However, the PMB-LPS complex was observed to be unstable in electrophoresis, even at a 1:40 molar ratio. It may be due to the small molecular weight of PMB relative to LPS. In contrast, G4 telodendrimers self-assemble into nanoparticles, which are more robust in trapping LPS in electrophoresis and may be more efficient in attenuating LPS binding with TLR-4 on immune cells. $G4(ArgVE)_4$ telodendrimers can encapsulate LPS stably even in the presence of 40 fold more PMB (FIG. 10*b*). As shown in FIG. 11, zwitterionic dendrimers $CB_{16}$-

Arg$_4$-VE$_4$ and GPC$_8$-Arg$_4$-VE$_4$ can bind to LPS and form nanocomplex efficiently, similar to G4 telodendrimers.

Affinitive resin for LPS and protein absorption. Both PMB and the dendritic moieties of G4 telodendrimers can be immobilized on polymer hydrogel resins (e.g., Tentagel® (TG) resin). As shown in FIG. 12a, TG-(ArgVE)$_4$ resin (i.e., ArgVE$_4$ bonded to TG) exhibits a stronger binding and higher LPS loading capacity than TG-PMB resin. In addition, with the addition of free PMB in the solution, TG-PMB showed observably reduced FITC-LPS intensity on the beads. In comparison, TG-(ArgVE)$_4$ resin maintains its LPS binding intensity. A highly-swollen hydrogel resin using PEGylated PVA polymer has been designed. The pore sizes in PVA-PEG resin as well as in TG resin allows for efficient diffusion of both LPS and small sized proteins (e.g., myoglubin (Mb)). In contrast larger sized BSA (65 kDa) can't penetrate into such hydrogel resins (FIG. 12b). The co-incubation of Rb-BSA and FITC-LPS with PVA-PEG(Arg-VE)$_8$ resin clearly revealed the size selectivity (FIG. 12c). The exclusion of large proteins is essential to reduce the competition of serum albumin protein moieties and antibodies with LPS and small molecular weight proteins (e.g., cytokines).

An appropriate pore size is important for efficient diffusion within a short period of time (1-2 hour), which allows for efficient clearance of cytokines and LPS by hemoperfusion. PEGA resin is another hydrogel resin which is more suitable for aqueous enzymatic reactions due to the larger pore sizes than TG resin. To compare the protein diffusion rate in different hydrogel resins, a FRET pair was immobilized (quenched) bridged by a peptide sequence, which is TNKase (~45 kDa) substrate. Upon TNKase diffusing into the beads, the peptide substrate is cleaved and bead becomes fluorescent. As shown in FIG. 12d, PVA-PEG resin allows for faster TNKase diffusion (within 2 hours) than PEGA resin (~12 hours). In addition the surface chemistry and physical properties of a resin are important for the antifouling and anticoagulant properties of packing materials. In addition, the absorbance of serum protein on the bead surface can be avoided by specific surface modification. Using a previously developed way to partition bead into multiple layers, as shown in FIG. 12e, amino groups on TG resin were partitioned into two or three layers with different protecting groups so that only the free amino layer can be stained blue by bromophenol blue. In this way, extra PEG or zwitterionic moieties were introduced on a thin surface layer of the PVA-PEG resin and PEGA resin to prevent cell adhesion and serum protein absorbance for better hemocompatibility and efficient LPS and cytokine removal.

In vitro LPS removal and attenuation. As shown in FIG. 13, after the incubation of FITC-LPS solution with PVA-PEG-(ArgVE)$_4$ resin for 4 h, greater than 99% of LPS was removed from the supernatant based on the fluorescence analysis. Even with 10,000-fold more BSA, LPS removal efficiency was only slightly decreased but was still more than 99%.

Discussion One aspect of the present disclosure is based on a novel dendritic charged amphiphilic structure for LPS and cytokine binding by the synergistic multivalent charge and hydrophobic interactions (FIG. 1). The solution form of the LPS binding dendron can be synthesized on cleavable Rink resin and cleaved into solution. The material binds LPS and destabilizes bacteria membranes as a bactericide.

Figure 2:
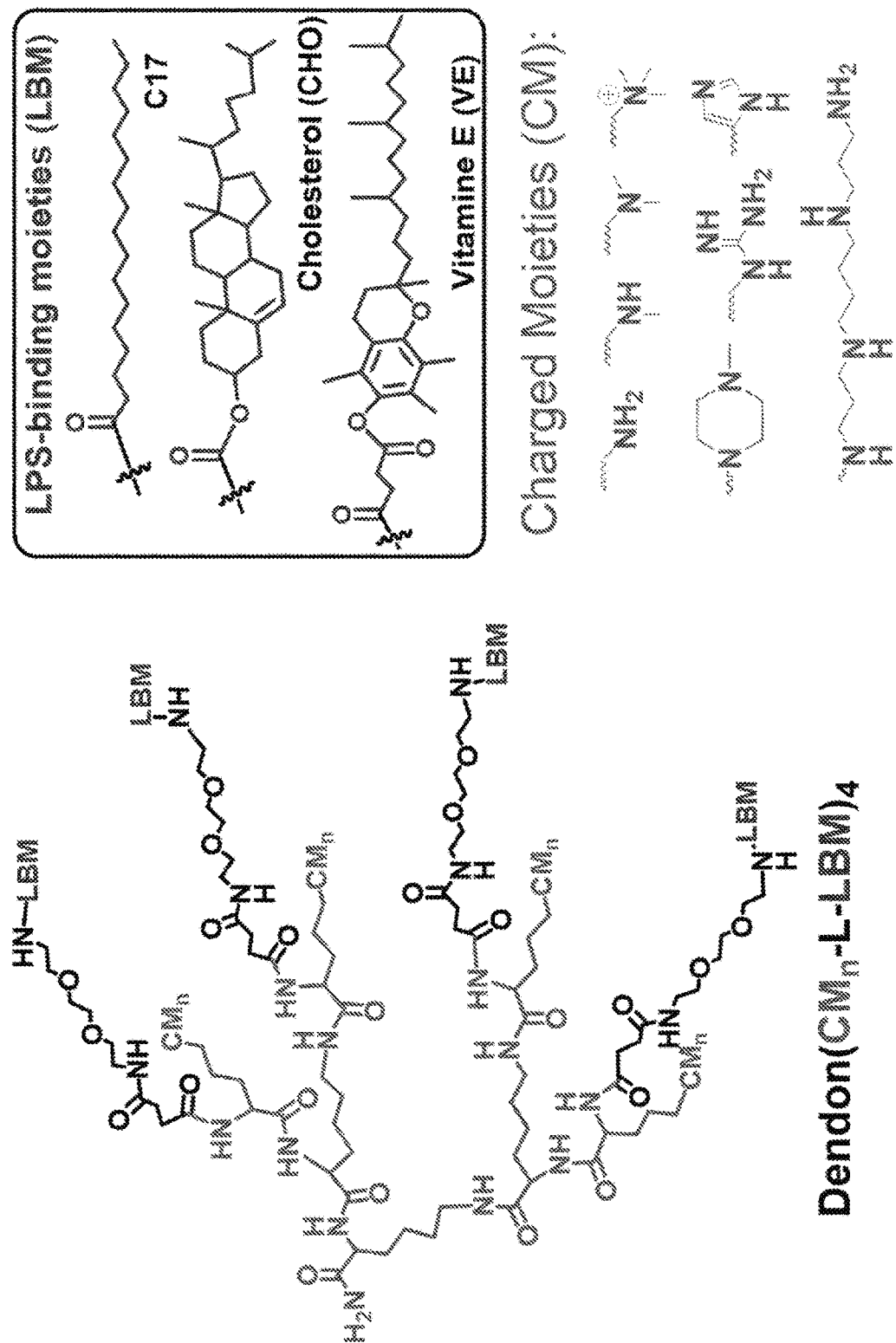
FIG. 2 shows dendron structures with the selection of charges and LPS binding moieties.

The following embodiments have been developed for the applications in sepsis control: 1$^{st}$, this amphiphilic dendron (FIG. 2) can be synthesized on a linear hydrophilic polymer, (e.g., PEG) (FIG. 3) or zwitterionic material (FIG. 4), to form telodendrimer nanoparticle in solution, which can be applied for systemic application to attenuate LPS in sepsis patient. 2$^{nd}$, the amphiphile can be synthesized or conjugated on a size exclusive hydrogel resin (FIGS. 5, 6 & 7), which can be packed into column for the removal of both LPS and small sized protein (e.g., cytokines), by blood filtration to reduce inflammation reactions in sepsis.

Figure 9:
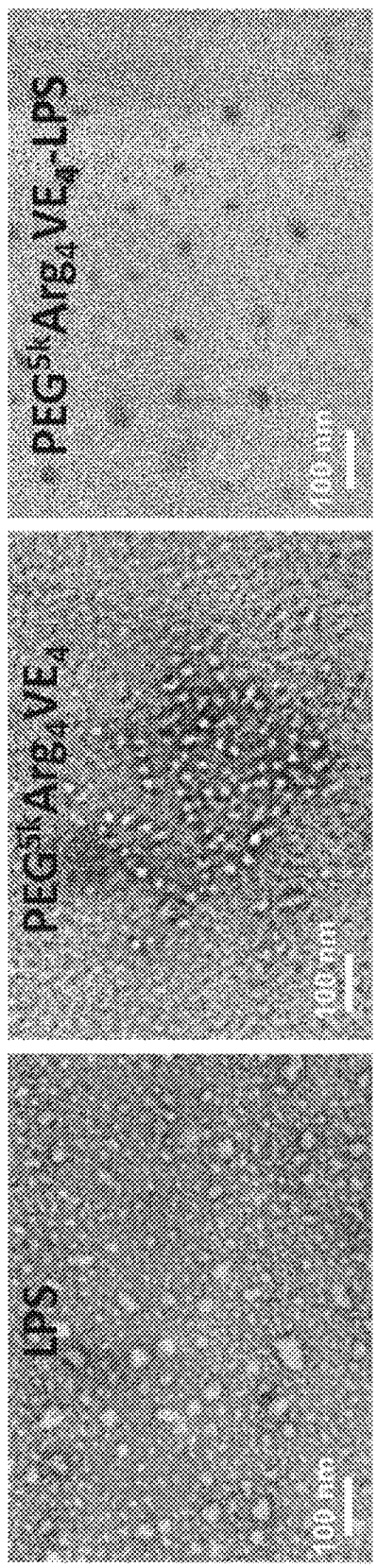
FIG. 9 shows particle sizes distribution under transmittance electronic microscopy (TEM) for LPS, the empty and LPS-loaded $PEG^{5k}Arg_4VE_4$ micelles.
Figure 10:
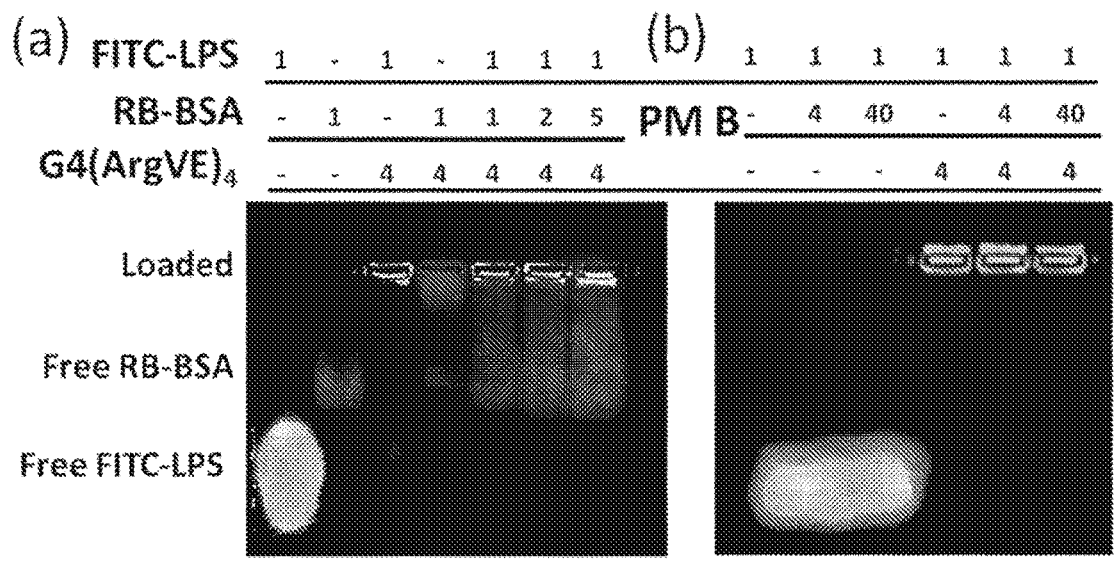
FIG. 10 shows (a) electrophoresis assays revealed that LPS and BSA can be loaded in $G4(ArgVE)_4$ nanocarrier efficiently at 1:4 of molar ratio; in addition, LPS was preferred to be loaded in nanocarrier in the presence of 5 fold more BSA; (b) PMB-LPS complex was shown to be not stable at even 1:40 in molar ratio; Instead, LPS can be stably loaded in $G4(ArgVE)_4$ in the presence of a 40-fold more PMB.
Figure 11:
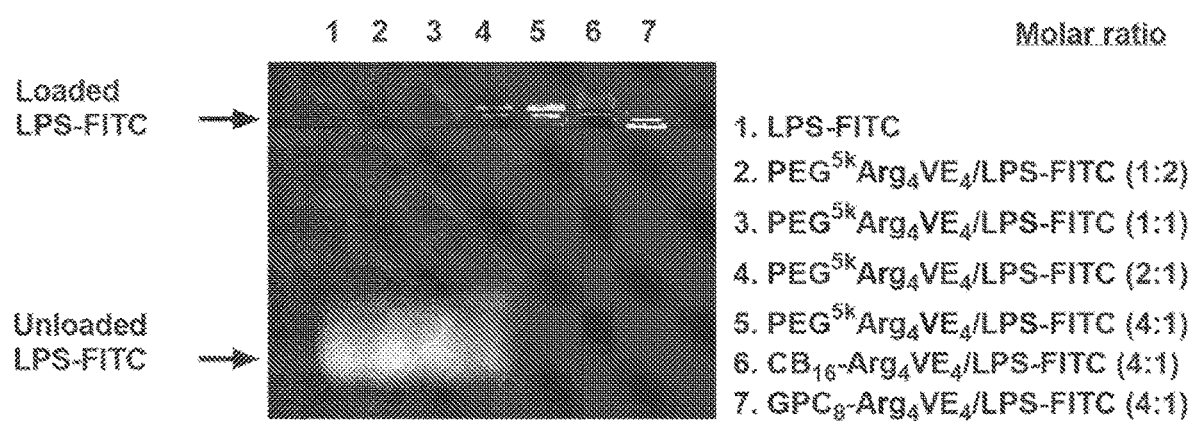
FIG. 11 shows electrophoresis assays revealed that LPS can be loaded in $PEG(ArgVE)_4$ telodendrimers efficiently at 1:4 of molar ratio; in addition, LPS can be efficiently loaded in zwitterionic Janus dendrimer $CB_{16}-Arg_4-VE_4$ and $GPC_8-Arg_4-VE_4$ at 1:4 of molar ratio.
Figure 12:
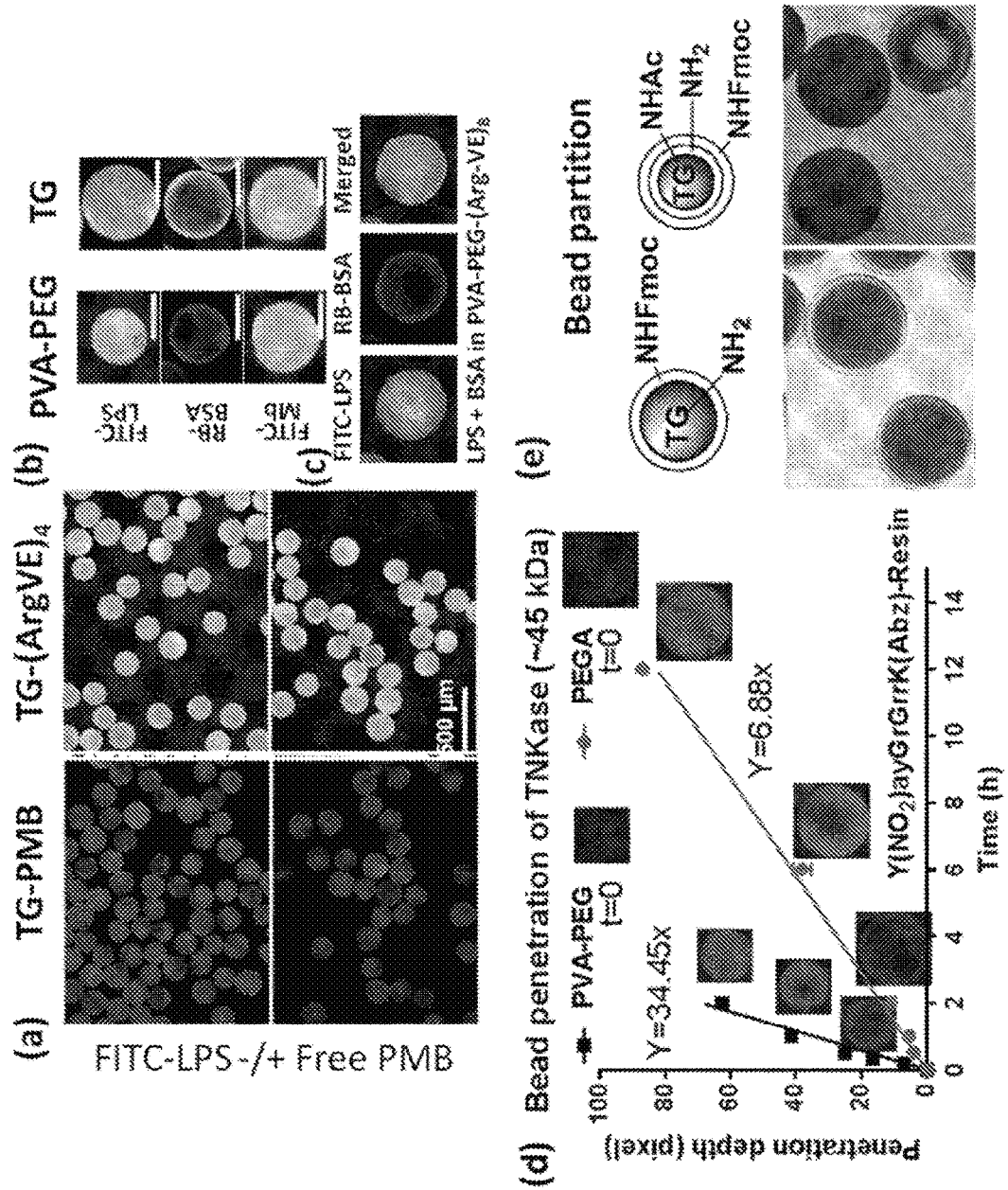
FIG. 12 shows a) fluorescent images of TG-PMB and TG-$(ArgVE)_4$ resins after incubated with FITC-LPS (10 μg/mL) for 5 min and further incubated with free PMB solution (1 mg/mL); (b) Confocal fluorescent images of PVA-PEG$(ArgVE)_4$ and TG-$(ArgVE)_4$ resins (equator section) after incubation with FITC-myoglobin(Mb), FITC/Rhodamin B-BSA and FITC-LPS; (c) PVA-PEG-$(ArgVE)_4$ resin was co-incubated with FITC-LPS and RB-BSA (1/100 n/n) for 2 h. Confocal fluorescent imaging revealed efficient LPS diffusion and BSA absorption on surface. (d) Diffusion profile of TNKase (45 kDa) into both PVA-PEG and PEGA beads, monitored by the bead light-up upon enzymatic cleavage of a FRET peptide substrate ($Y(NO_2)ayGrGrrK$ (Abz)) immobilized on the beads; (e) Precise bead partition into different layers (free —$NH_2$ was stained into blue).

These telodendrimers have been engineered based on the structure of LPS with the aid of computational design and combinatorial telodendrimer synthesis to optimize LPS binding affinity and specificity (FIG. 8). Telodendrimers of the present disclosure bind LPS and form small nanoparticles <25 nm (FIG. 9) and the binding affinity is even stronger than telodendrimers bind to the model proteins, owing to the significant well-defined negative charges and hydrophobic structure of lipid A domain in LPS, whereas protein surface chemistry are hydrophilic. (FIG. 10a). In addition, binding of telodendrimers of the present disclosure to LPS is even stronger than binding of polymyxin B to LPS (FIG. 10b). Zwitterionic Janus dendrimer with the identical LPS-binding dendrons can also efficiently encapsulate LPS, which is potential to attenuate LPS in vivo to treat sepsis. Experiments have demonstrated that telodendrimer nanocarriers can be administrated safely for systemic drug/protein delivery. Based on the ability of telodendrimers and telodendrimer nanoparticles of the present disclosure to bind LPS and their nontoxicity, the instant telodendrimers are promising for efficient systemic LPS attenuation in patients, which is still unmet need in clinical practice. In addition, these dendrons with their LPS binding moieties can be conjugated on size-selective hydrogel beads for the extracorporeal removal of both LPS and cytokines. Hydrogel resin with the right pore sizes will allow smaller sized proteins (<50 kDa), such as, for example, cytokines and LPS, to efficiently diffuse into the resin where they can be efficiently bonded by telodendrimer moieties (FIG. 12). The in vitro incubation of LPS solution with LPS-binding resin has shown great efficiency (>99%) for LPS removal, even in the presence of abundant BSA (100-fold more in mass). Both modalities, for systemic LPS attenuation and for extracorporeal LPS/cytokine removal, are highly applicable in clinical settings to treat sepsis and are promising to prevent multiple organ failure and death of severe septic patients.

Conclusion. By exploiting the distinct and unique lipid A structure in LPS, the telodendrimers of the present disclosure efficiently and specifically capture LPS. Efficient encapsulation of LPS in a nanoparticle offers a promising way to prevent LPS-induced TLR-4 plasma-membrane signaling of the proinflammatory pathway; nanoparticle-induced endocytosis of LPS in macrophages activates anti-inflammatory pathway and provides a mechanism for LPS clearance by phagocytic degradation. In addition, the implantation of efficient (LPS+/Mb+) G4 telodendrimer moieties into a size-exclusive hydrogel beads will be able to absorb both LPS and the whole set of proinflammatory cytokines from blood stream to attenuate both the triggers and effectors of systemic inflammatory reactions. Therefore, G4 telodendrimer can be detailed in two formats to tackle the challenge in sepsis management by means of (1) nanocarrier for systemic LPS attenuation or (2) immobilized on the size-exclusive cartridge for hemoperfusion use to remove both LPS and proinflammatory cytokine.

Example 2

This example provides synthesis and methods of use of sorption materials of the present disclosure.

In this example, telodendrimers (TD) nanotraps were immobilized on the size-exclusive hydrogel resins for the simultaneous adsorption of a broad range of casual insults and selective mediators from biological mediums (e.g., lipopolysaccharides (LPS) and cytokines and damage/pathogen-associated molecular patterns (DAMPs/PAMPs)). The optimized nanotrap resins exhibit a 10-fold greater LPS removal efficiency than the commercial polymyxin B (PMB)-based resins and significantly attenuated LPS from stimulating immune cells for TNF-α production. The rational selection of charges (positive or negative) and hydrophobic moieties on nanotrap fine-tunes the profiles of septic molecules adsorbed on the resin as evidenced by ELISA, electrophoresis and mass spectrometry studies. A set of inflammatory cytokines are efficiently removed by >92% from the plasma of septic mice induced by cecal ligation and punctuation. The fine-tuning of the nanotrap allows for the development of highly efficient and selective hemoperfusion cartridge to reduce the mortality of severe sepsis.

Disclosed is a well-defined telodendrimer (TD) nanoplatform, functionalized with multivalent charges and hydrophobic moieties on the periphery of a dendritic scaffold for efficient protein encapsulation. TD nanotraps adopt free conformational changes to maximize the binding with a variety of biomacromolecules via synergistic combinations of ubiquitous electrostatic and hydrophobic interactions. LPS commonly possesses distinct negative charges (phosphate) and hydrophobic lipid tails in the lipid A fragment, which provide effective anchors for TD binding. Interestingly, most proinflammatory cytokines (TNF-α, IL-1, IL-6, IL-12, and HMGB1) are characteristic of negative charges (PI: 4.1~6.4); major anti-inflammatory cytokines (IL-10, TGF-β and IL-4) are instead positively charged. Therefore, the majority of proinflammatory cytokines can be selectively captured by the positively charged TDs through ionic and hydrophobic interactions. Cytokines are signaling molecules and generally small in size with molecular weights of 10~30 kDa, similar to LPS (10~20 kDa). The dendritic nanotrap was further conjugated onto a size-exclusive hydrogel resin (pore size ~50 kDa) to provide affinity and selectivity for biomacromolecules of interest by taking advantage of the structural characteristics. Size-exclusive TD nanotrap allow for the diffusion and capture of small-sized LPS and cytokines, and the exclusion of the abundant large serum albumin (67 kDa) and antibodies (>150 kDa) from blood to eliminate the competitive binding.

Lipopolysaccharide (LPS) binding by telodendrimers (TD). Lipid A is the most structurally conservative component in LPS and elicits strong host innate immune responses in animals and human. Polymyxin B (PMB) is secreted by GN bacteria, *Bacillus polymyxa*, to lyse GN bacteria by binding to lipid A in LPS on the outer membrane. PMB has a cyclic polypeptide with multiple cationic and hydrophobic amino acids and a short fatty acid tail, which bind to some LPS with the favorable conformations. However, GN bacteria may mutate LPS structures to weaken PMB binding, which contributes to the PMB resistance. In addition, the hydrophobic moieties in PMB are smaller than the fatty acid tails in LPS as shown in the molecular modeling studies, resulting in the moderate binding affinities between PMB and LPS within a few micromolar range. In an attempt to explore efficient and nontoxic LPS binder, a novel flexible TD nanoplatform, which is decorated with multiple positive charges and hydrophobic moieties for both protein and LPS binding (FIG. 14a) was designed. Starting from poly (ethylene glycol) (PEG) (Mw~5 k), the dendritic scaffold of TD was constructed with the branched oligolysine and functionalized with positively charged arginine (Arg) or lysine and hydrophobic moieties (R) (e.g., heptadecanoic acid (C17), vitamin E (VE) and cholesterol (CHO) (denoted as PEG$^{5k}$(ArgR)$_4$, FIG. 21)). The formation of TD and LPS nanocomplex (TD-LPS) was initially characterized by the particle size analyses via both dynamic light scattering (DLS) and transmittance electronic microscope (TEM). Slightly reduced particle size was observed (24±10 nm) for TD-LPS in comparison to TD (32±12 nm) and LPS (30±9 nm) aggregates, suggesting the re-assembly of nanoparticles (FIG. 22). Steady-state fluorescent polarization (FP) spectrometry was further applied to study the complexation of FITC-LPS (10 μg/mL) with PMB and TD nanotrap, respectively (FIG. 23). FP of FITC-LPS was only slightly increased even with 20-fold excess of PMB (w/w) added, indicating that the mobility of FITC-LPS was barely decreased. The formation of a small complex of LPS and PMB was suggested by the FP study. Whereas, the conformational mobility of FITC-LPS was strongly restricted in TD-FITC-LPS nanocomplex as reflected by the dramatic increase in FP, suggesting the compact molecular packing and the formation of large nanoparticles.

LPS isolated from two most common sepsis-causing GN bacteria, *E. coli* and *P. aeruginosa*, can be efficiently loaded in PEG$^{5k}$(ArgVE)$_4$ nanoparticles, as evidenced by an electrophoresis assay (FIG. 14b). In contrast, PMB-LPS complex is unstable and dissociated in electrophoresis assay even at 40:1 mass ratio of PMB/LPS (FIG. 14c). TD-LPS nanocomplex was observed to be stable even in the presence of 40-fold excess of PMB. Additionally, TD-LPS nanocomplex remains undisturbed in the presence of increased serum protein (FIG. 14d), indicative of superior TD-LPS binding affinity, which is due to the distinct and defined charge and hydrophobic domains in LPS in comparison to proteins for TD binding. Additional computational studies also revealed the higher docking energy of TD fragments binding to LPS than to BSA (FIG. 8).

Figure 15:
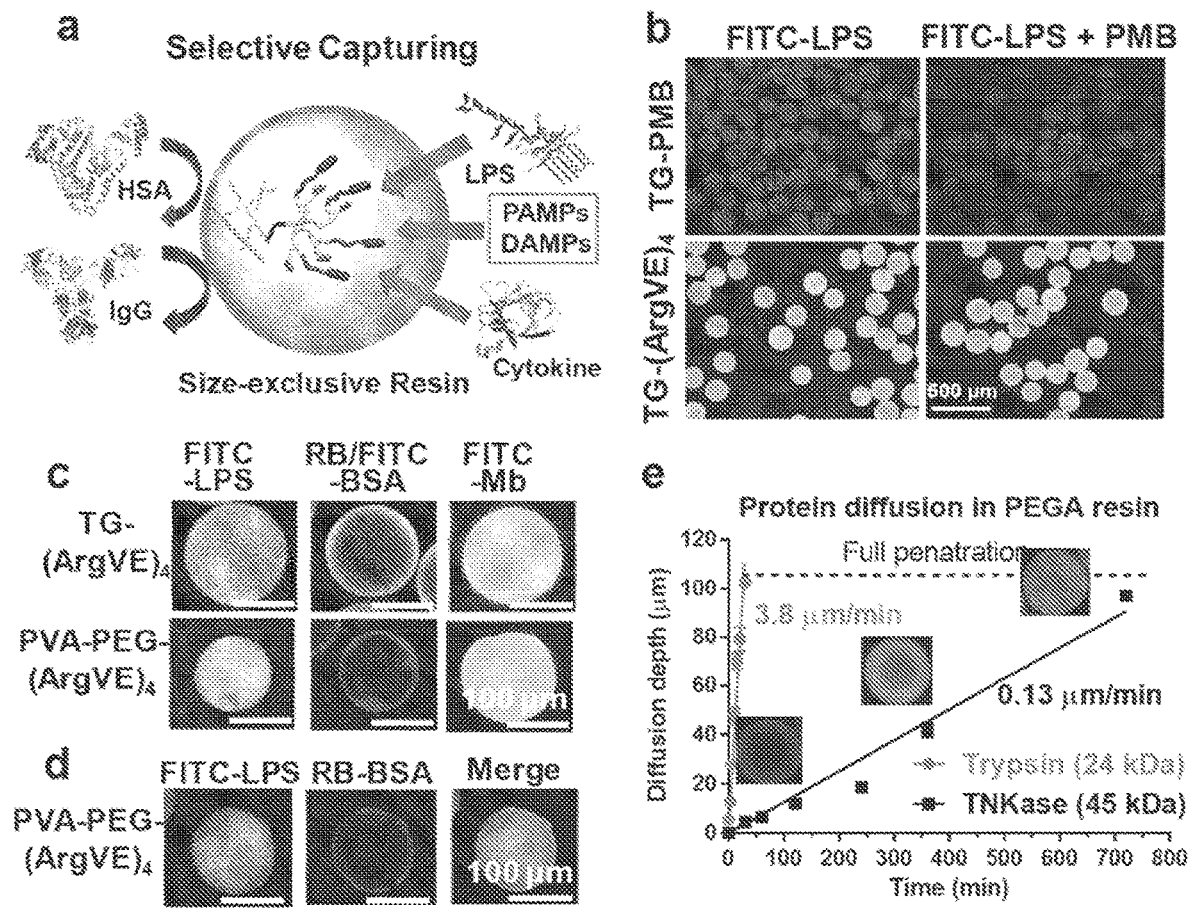
FIG. 15 shows a) schematic representation of selective LPS and cytokine removal by nanotrap-immobilized size-exclusive resin. b) Fluorescent microscopy images showing the adsorption of FITC-LPS by TG-$(ArgVE)4$ and TG-PMB resins in the absence or presence of free PMB to compete for binding. c) Z-stack confocal images showing the penetration level of fluorescently labeled biomolecules (FITC-LPS, FITC-BSA or RB-BSA, and FITC-Mb (myoglobin)) into nanotrap modified TG and PVA-PEG resins, respectively. d) Z-stack confocal images of PVA-PEG-$(ArgVE)4$ resin co-incubated with FITC-LPS and RB-BSA (1:100 mass ratio). e) Kinetic diffusion of protease with different molecular weight (Trypsin and TNKase) in PEGA resin: beads were light up while enzyme diffuses and cleaves the specific substrate immobilized in the bead, therefore releasing the quencher (nitrotyrosine) from the fluorescent dye (Abz) (see FIG. 27).

Nanotrap immobilized on the size-exclusive resins. LPS and the majority of cytokines have relatively small molecular weights (10~30 kDa). Therefore, the TD nanotrap on size-exclusive hydrogel resins were conjugated to selectively capture these septic molecules and exclude the large and abundant serum albumin protein and immunoglobulin from competing for binding (FIG. 15a). TentaGel (TG) resin is a hydrophilic resin commonly used for solid-phase peptide synthesis, which was initially applied for TD nanotrap synthesis (FIG. 24). Similarly, TD nanotrap was synthesized on a cleavable Rink resin and intermediates of TD were cleaved for the structural characterization. MALDI-TOF MS analysis confirmed the identical molecular ion peaks of the intermediates (FIG. 25a). The precise structure of the TD nanotrap bearing four arginine and C17 groups were confirmed by both MALDI-TOF MS and NMR spectra (FIGS. 25b and c), which indicated the well-defined TD nanotrap synthesized on the size-exclusive resins. The nanotrap resins with the arginine and hydrophobic moieties (R) are denoted as RESIN-(ArgR)$_4$.

Similar to previous observations for protein encapsulation by TD nanoparticle, the combination of both electrostatic and hydrophobic interactions in nanotrap is also important for LPS binding. Control hydrogel resins with only charge or hydrophobic moieties exhibit weaker FITC-LPS adsorption relative to nanotraps with both functionalities (FIG. 26a), which correlated with the 10-20% vs. ~95% decrease of LPS in the solutions (FIG. 26b). After four adsorption-regeneration cycles, the LPS removal efficiency of nanotrap resin in PBS remains ~95% (FIG. 26c). TG-(ArgVE)$_4$ resin could adsorb FITC-LPS rapidly and efficiently after a brief incubation (2-3 min) and beads were light up intensively (FIG. 15b). In contrast, PMB-immobilized TG resin was only slightly fluorescent under the identical condition, which was diminished in the presence of free PMB for competitive binding. No obvious changes of the on-bead fluorescent intensity were observed for FITC-LPS on TG-(ArgVE)$_4$ resin in the presence of PMB.

The molecular diffusion into hydrogel resins is governed by both molecular weight of the targeted protein and the pore size of the hydrogel network. An ultra-hydrophilic PVA-PEG resin was prepared according previous reports, and applied to tether TD nanotrap. Confocal images revealed that FITC-LPS diffuses efficiently into the core region of both TG-(ArgVE)$_4$ and PVA-PEG-(ArgVE)$_4$ (FIG. 15c). However, BSA with larger size can only be captured on the surface of both TG and PVA-PEG resins. Myoglobin (Mb, 16.7 kDa, PI: 6.8) was used as a small model protein to mimic cytokine, which also diffuses freely across the entire resins. PVA-PEG-(ArgVE)$_4$ resins were further incubated with the mixture of FITC-LPS and RB-BSA (1:100, w/w). Confocal images reveal that FITC-LPS signal is distributed throughout the entire resin and is unaffected by the presence of abundant BSA (FIG. 15d). Another commercial and enzyme-accessible PEGA hydrogel resin was also used for TD nanotrap synthesis. Protein diffusion kinetic studies were conducted on PEGA resin and PEG-PVA resin with different pore sizes. PEGA was confirmed to have a smaller pore size of ~50 kDa than PEG-PVA resin (FIG. 27), making it ideal for the selective adsorption of septic molecule in blood. To test the protein diffusion, two Förster resonance energy transfer (FRET) peptide substrates on PEGA resin, Y(NO$_2$)dlHKSriK(Abz) and Y(NO$_2$)ayGrGrrK(Abz), for Trypsin (24 kDa) and TNKase (Tenecteplase) (45 kDa), respectively, were synthesized. Upon enzymatic cleavage of peptides, the fluorescent quencher, Y(NO$_2$) (3-Nitrotyrosine), will be removed and Abz(ortho-aminobenzoic acid) becomes fluorescent to on bead, indicating the protein penetration. As shown in FIG. 15e, smaller trypsin diffuses ~30-fold faster than TNKase in PEGA resin, which indicates the excellent selectivity to cytokines over larger serum proteins.

Figure 16:
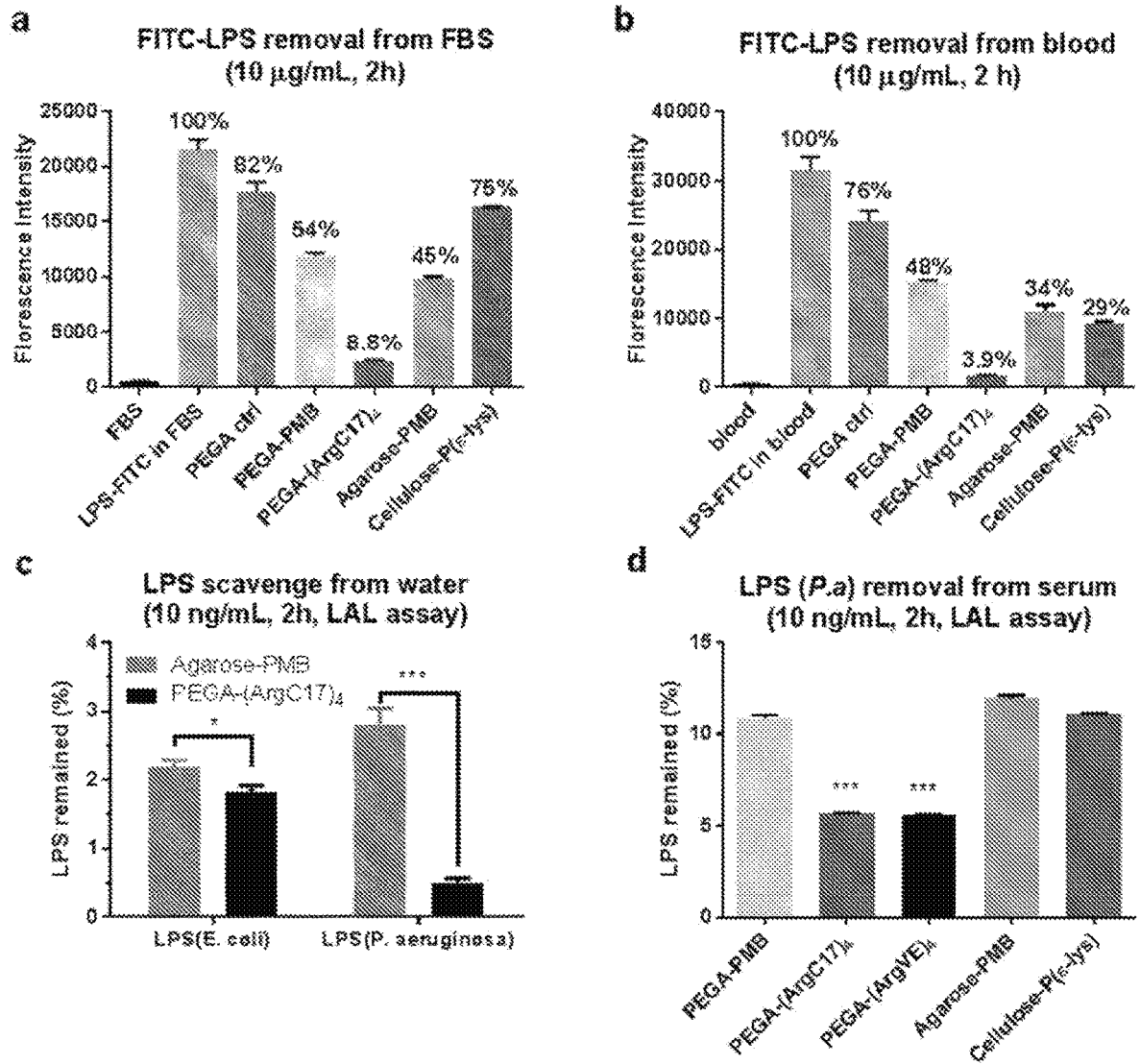
FIG. 16 shows removal efficiency of FITC-LPS at a high concentration (10 μg/mL) by nanotrap PEGA hydrogel resins in comparison to commercial LPS-removal resins in a) FBS and b) in whole blood after 2 h incubation, respectively. The removal efficiency of native LPS at pathological concentration (10 ng/mL) by hydrogel resins in c) water and d) FBS after 2 h incubation as detected by LAL assay. * $P<0.05$; *** $P<0.001$.

LPS removal from biological fluids. FITC-LPS doped fetal bovine serum (FBS) and whole blood from healthy human volunteer at a high concentration of 10 μg/mL were incubated with PEGA-(ArgC17)$_4$ resins. Acetylated PEGA resin was used as a control and PEGA-PMB and two commercial LPS-removal resins, agarose-PMB resin, and cellulose-poly(ε)lysine were tested for comparison. PEGA-(ArgC17)$_4$ can remove FITC-LPS from FBS with an efficiency of ~91% after 2 h incubation (FIG. 16a), which already reached to the equilibrium as referenced to the overnight incubation (FIG. 28a). In comparison, PMB-based resins only remove 46% to 55% of LPS and polylysine-resin was only slightly better than the PEGA control (25% vs. 18%). Remarkably, PEGA-(ArgC17)$_4$ removed even greater FITC-LPS from whole blood with an efficiency of ~96% after 2 h incubation (FIG. 16b). Accordingly, 52%, 64% and 70% of LPS were eliminated from blood after the incubation with PEGA-PMB, agarose-PMB and cellulose-polylysine resins for 2 h, which remained unchanged after prolonged incubation (4 h, FIG. 28b). TD Nanotrap resins reduce LPS concentration in blood to ~10-fold lower than that achieved by the commercial LPS-removal resins. The post-incubation PEGA-(ArgC17)$_4$ resins were significantly brighter than all other resins examined under fluorescent microscope (FIG. 29). It was found that polylysine modified cellulose beads were fully coated by blood cells, which may block mass transport and induce blood clotting. In contrast, PEGA resins were observed to be free of cell attachment on the surface, indicating the good hemocompatibility.

LPS adsorption efficiency was further tested at pathological concentration (e.g., ~10 ng/mL) by limulus amebocyte lysate (LAL) assay. As shown in FIG. 16c, PEGA-(ArgC17)$_4$ nanotrap resin show enhanced efficiency in removing two native LPS, originated from E. coli and P. aeruginosa in water by 98% and 99%, respectively, which are significantly more efficient than a commercial PMB containing agarose resin. Several types of resins were then examined in capturing LPS in FBS after 2 h incubation. Both C17 and VE-containing nanotrap can efficiently remove ~95% of LPS from serum (FIG. 15d), showing the improved performance as compared to other PBM-containing and polylysine resins.

Figure 17:
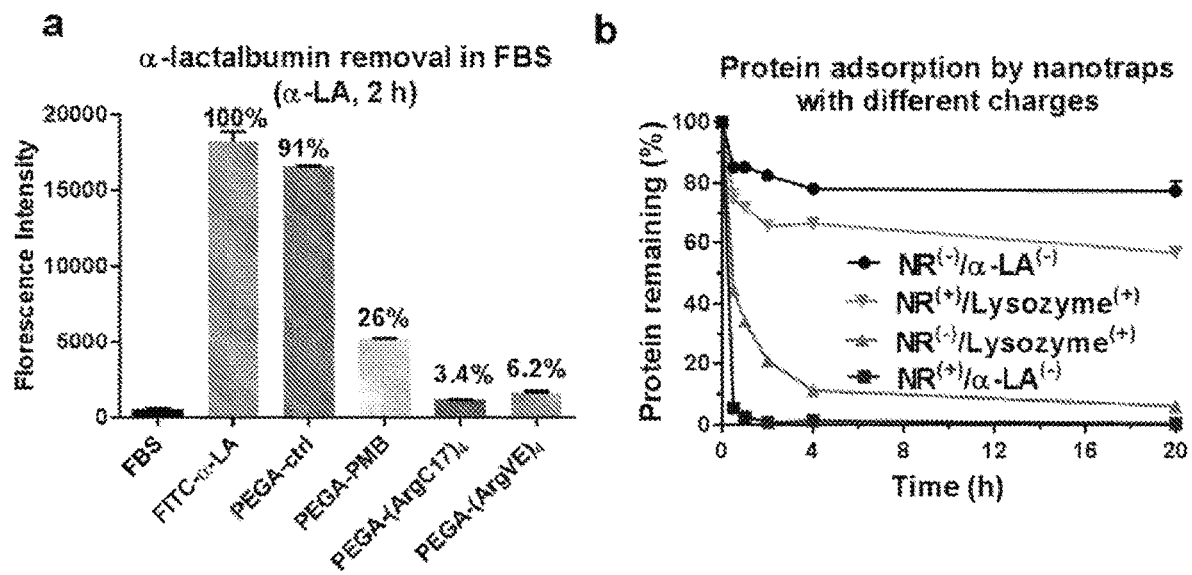
FIG. 17 shows a) adsorption efficiency of negatively charged FITC-labeled α-lactalbumin (α-LA) by various positively charged resins in FBS after 2 h incubation. b) The kinetic adsorption profiles of FITC-labeled α-LA$^{(-)}$ and lysozyme$^{(+)}$ by nanotrap resins (NR) with positive (arginine) or negative (oxalic acid (OA)) charges, respectively: NR$^{(+)}$: PEGA-$(ArgC17)_4$; NR$^{(-)}$: PEGA-$(OAC17)_4$. c) MALDI-TOF MS analysis of the protein mixture solution of α-LA (0.5 mg/mL), lysozyme (Lyz) (0.5 mg/mL) and BSA (5 mg/mL) before and after incubation with PEGA-$(ArgC17)_4$ resin at different time with bead/solution ratio of 1:10 v/v. d) The kinetic α-LA adsorption profiles by PEGA-$(ArgC17)_4$ nanotrap resin characterized by comparing the peak intensity of α-LA relative to that of Lyz. e) MALDI-TOF MS analysis of the protein mixture solution of α-LA$^{(-)}$ (0.1 mg/mL, PI: 4.5, 14.2 kDa), lysozyme$^{(+)}$ (Lyz, 0.1 mg/mL, PI: 11.6, 14.4 kDa), myoglobin (Mb, 0.1 mg/mL, PI: 6.8, 16.7 kDa) and BSA$^{(-)}$ (1 mg/mL, PI: 4.8-5.4, 66.4 kDa) before and after incubation with acetylated PEGA, PEGA-(ArgC17)$_4$, and PEGA-(OAC17)$_4$ resins, respectively, at bead/solution ratio of 1:4 (v/v). f) MALDI-TOF MS analysis of proteins eluted from nanotrap resins with 8 M urea, indicating the significant charge selectivity for protein binding.

Selective protein adsorption from biological fluids. Interestingly, cytokines feature a significant correlation between surface charges and functions: i.e. negative surface charges (PI: 4.1~6.4) for the majority proinflammatory cytokines (TNF-α, IL-1, IL-6, IL-12, and HMGB1); and positive surface charges (PI: 8.2~11.7) for most key anti-inflammatory cytokines (IL-10, TGF-β, IL-4, and IL-11). Therefore, two model proteins, α-lactalbumin (α-LA, 14.2 kDa, PI: 4.5) and lysozyme (Lyz, 14.4 kDa, PI: 10.7) were selected to mimic pro- and anti-inflammatory cytokines, respectively. As expected, both PEGA-(ArgC17)$_4$ and PEGA-(ArgVE)$_4$ resins with positive charges were able to scavenge FITC-α-LA efficiently with 94% and 96% after 2 h incubation, respectively (FIG. 17a), whereas, only basal level of α-LA at 10% was physically trapped in PEGA control resin. PEGA-PMB resin was observed to remove about 74% of negatively charged α-LA from FBS. A negatively charged oxalic acid (OA)-containing nanotrap on PEGA resin, PEGA-(OAC17)$_4$, was prepared for direct comparison of the charge interactions between nanotrap resin (NR) and model proteins in adsorption (FIG. 17b). As expected, the attractive electrostatic interactions significantly improve protein adsorption in NRs: for example, the negative protein α-LA$^{(-)}$ was adsorbed more efficiently on PEGA-(ArgC17)$_4$NR$^{(+)}$ than the positively charged lysozyme$^{(+)}$ (~90% vs. 20% after 4 h incubation); NR$^{(-)}$ adsorbs lysozyme$^{(+)}$ more efficiently than trapping α-LA$^{(-)}$. Interestingly, Arg-containing NR$^{(+)}$ exhibited faster adsorption kinetic than the OA-containing NR$^{(-)}$ with the identical C17 moiety for both α-LA and lysozyme, which may be due to the difference in ionic strength and hydrogen bonding capability.

Figure 17C:
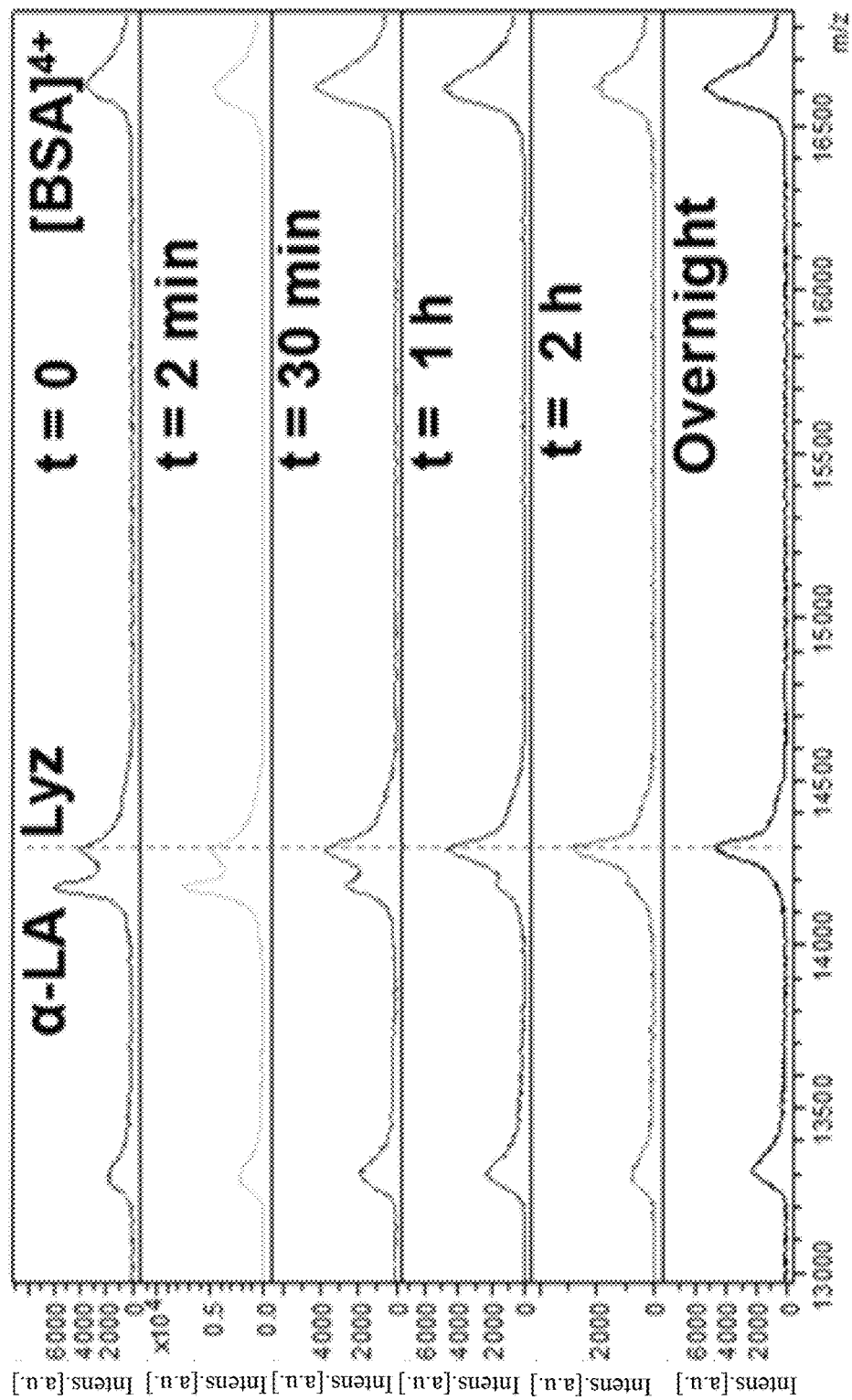
Figure 17:
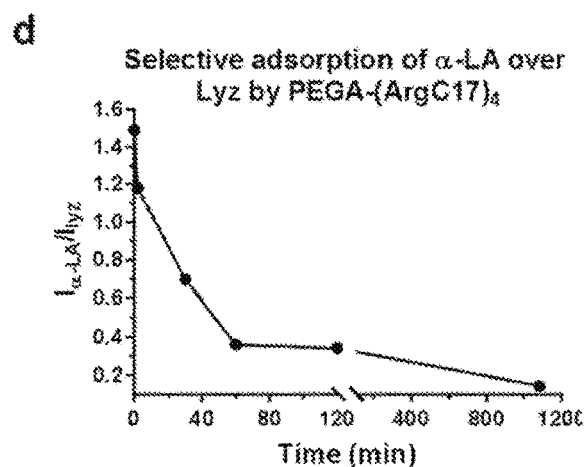
Figure 17:
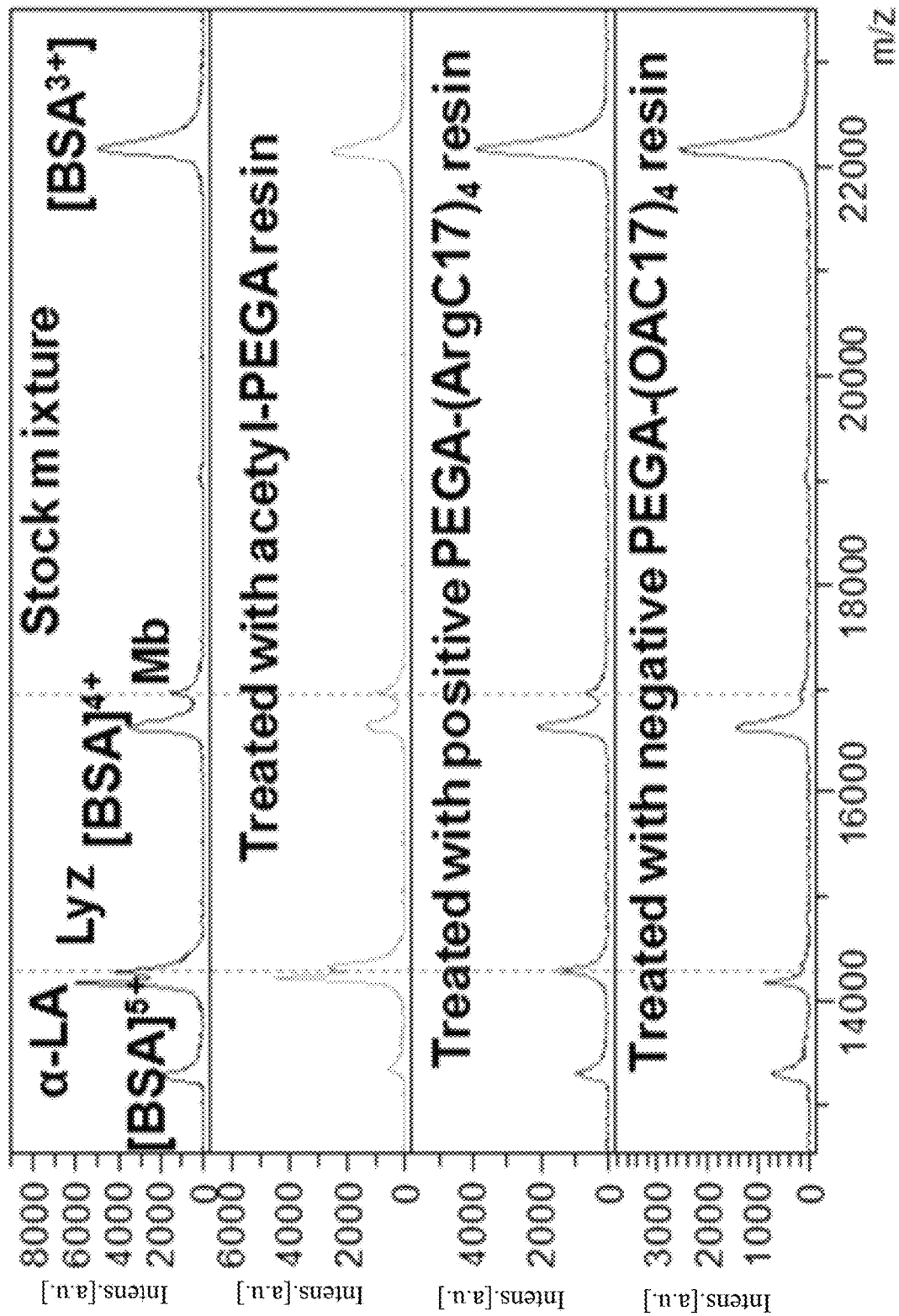
Figure 17F:
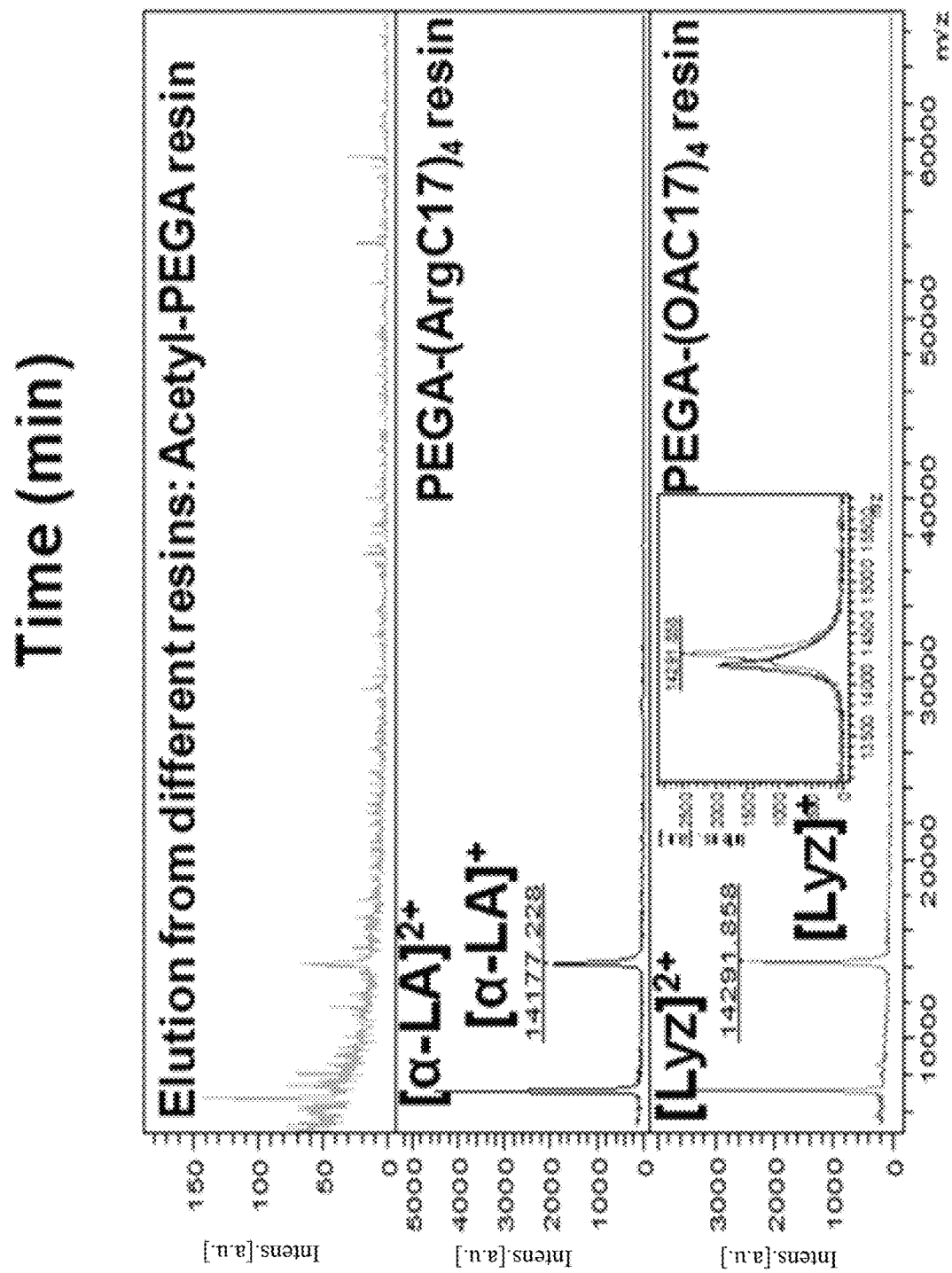
Figure 30A:
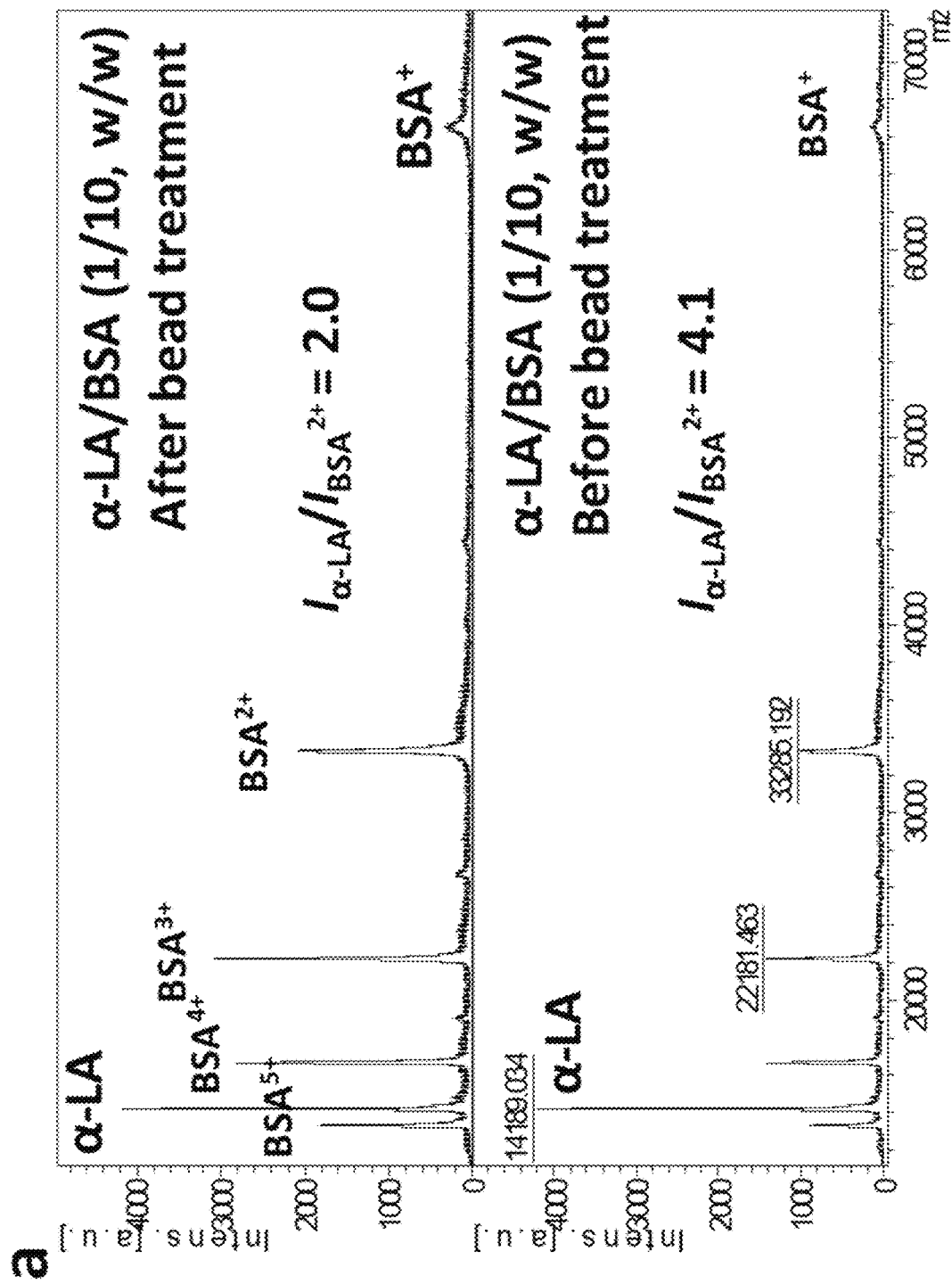
Figure 30B:
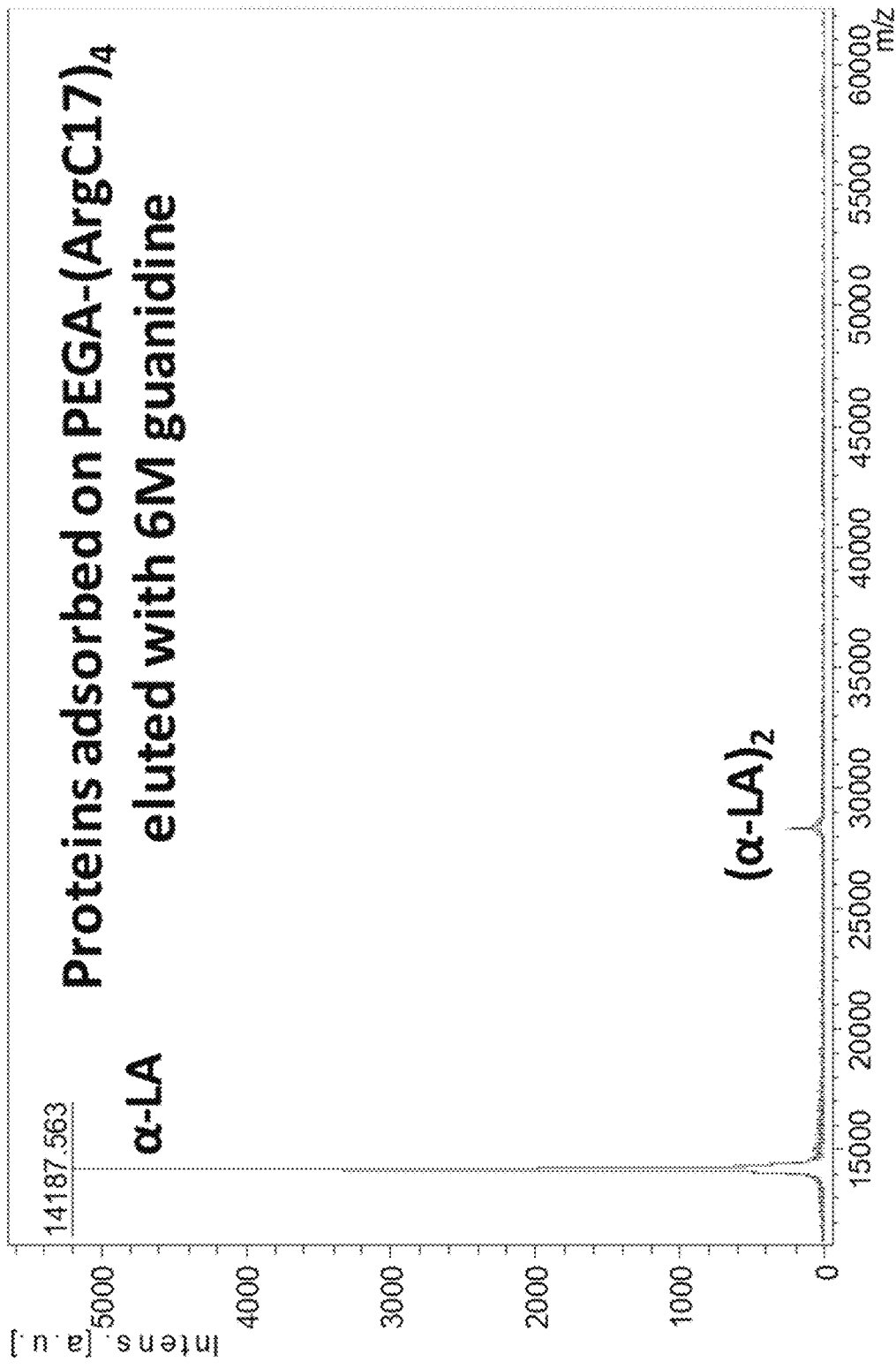

MALDI-TOF MS was used to characterize the efficiency and selectivity of nanotrap resins in adsorbing native proteins. The protein mixtures of α-LA, Lyz and BSA were incubated with PEGA-(ArgC17)$_4$ resin, and sampled at different time points for MALDI-TOF MS analysis (FIG. 17c). α-LA was gradually decreased relative to BSA signals, and Lyz remained steady. The intensity ratio of α-LA to Lyz was plotted overtime to reflect the charge selectivity (FIG. 17d) and indicate the rapid adsorption of α-LA within 1 h incubation (FIG. 17b). BSA and model proteins with different isoelectric points (pI's) were then combined for the incubation with nanotrap resins of different nature of charges. Neutral acetylated PEGA resin made no change on the relative intensities of all proteins in comparison to the stock solution (FIG. 17e). The positive PEGA-(ArgC17)$_4$ resin adsorbed α-LA (PI: 4.5) efficiently from the solution and a noticeable decrease of neutral protein myoglobin (Mb, PI: 6.8) was also observed. In contrast, the negatively charged PEGA-(OAC17)$_4$ resin completely scavenged the positively charged Lyz (PI: 11.6) with α-LA remaining in the solution. It was also noticed that Mb was removed more dramatically by PEGA-(OAC17)$_4$ than PEGA-(ArgC17)$_4$. Proteins from these resins were eluted by treating with 8 M urea for MALDI-TOF MS analysis (FIG. 17*f*). Weak signals were observed in the elution of acetylated PEGA resin. In contrast, exclusive signals of α-LA and Lyz were detected in the elution from the positive and negative nanotrap resins, respectively, indicating the efficient charge selectivity in protein binding. In addition, no BSA signals were identified in all these elution, suggesting the distinct size exclusive effects of PEGA resin. PEGA-(ArgC17)$_4$ resin was saturated with protein adsorption by the increased concentrations of α-LA (0.5 mg/mL) and BSA (5 mg/mL). MALDI-TOF MS analysis revealed a 50% reduction of α-LA signal relative to BSA in the mixture solution after bead incubation (FIG. 30*a*). Accordingly, the loading capacity of α-LA was determined to be 13 μg α-LA/mg resin. Consistently, MALDI-TOF MS analysis of the elution revealed that α-LA was solely adsorbed on the resins (FIG. 30*b*).

Attenuation of LPS in stimulating TNF-α production. Immune cells produce proinflammatory cytokines upon stimulation with pathogen/damage-associated molecular patterns (PAMPs/DAMPs) (e.g., LPS). Murine macrophage RAW 264.7 cells was stimulated with LPS directly or with the LPS treated with different sorbent resins (FIG. 18*a*). The TNF-α produced in the cell medium after overnight stimulation was analyzed via TNF-α ELISA assay. LPS efficiently induced the production of 2500 μg/mL TNF-α (FIG. 18*b*). In comparison, the treatment with PEGA-TD resins containing either VE or C17 moieties significantly inhibited TNF-α secretion by more than 90%, which were more efficient than the 50-60% inhibition by PMB-containing PEGA resin and agarose resin. Polylysine modified cellulose resin exhibited similar TNF-α attenuation to the control resin with 25% decreased TNF-α release, which is well correlated with their poor efficiencies in LPS removal in FBS (FIG. 16*a*).

Scavenging of TNF-α from serum. The capacity of TD resins in direct scavenge of TNF-α was assessed in PBS or FBS solutions spiked with 1 ng/mL of TNF-α. PEGA-(ArgC17)$_4$ resin significantly scavenged TNF-α in both PBS and FBS by 74% and 55% reduction after 2 h incubation (FIG. 19*a*), which were further improved to 91% and 85% after overnight incubation, respectively (FIG. 19*b*). PEGA control was observed to trap TNF-α non-specifically by 17% in PBS, which were eliminated by the competing adsorption of small proteins in FBS. In contrast, the total protein levels in solution were measured to be almost identical before and after incubation (FIG. 19*c*), which reflects the selectivity in removing small proteins over serum. Interestingly, VE-containing PEGA-(ArgVE)$_4$ exhibited significantly lower efficiency than PEGA-(ArgC17)$_4$ in adsorbing TNF-α in both PBS and FBS media, which may be due to the rigid structure of VE functionality. The relatively slower TNF-α removal is likely attributed to the presence of TNF-α trimer (51 kDa), which may diffuse slowly into PEGA resin similar to TNKase (45 kDa). PVA-PEG resin with large pore size may allow for faster diffusion of TNF-α trimers.

Removal of spontaneous cytokines from septic blood. Sepsis model in mouse was induced by cecal-ligation and puncture (CLP) procedure (FIG. 20*a*), which is the most widely used sepsis model to mimic human sepsis pathogenesis and progression. Sepsis was successfully induced 24 h post-CLP surgery. Unfortunately, hemoperfusion procedure in mouse is limited by the small blood volume. Alternatively, we collected septic blood from CLP mice and isolated plasma for incubation with the most efficient nanotrap resin PEGA-(ArgC17)$_4$ at 10:1 plasma/bead volume ratio for 4 h to mimic hemoperfusion conditions. The concentrations of three important early and late proinflammatory cytokines, TNF-α, IL-1β and IL-6, were analyzed via ELISA assays. As shown in FIG. 20*b*, IL-1β was detected to be 133±22 μg/mL and 8.4±3.1 μg/mL, respectively, before and after bead treatment, representing a 93.7% of removal. Similarly, IL-6 with a high expression in septic blood was efficiently removed by 98.6% after bead incubation. In comparison, TNF-α was only detected as low as 15.4±3.8 μg/mL and almost non-detectable after bead treatment (−1.5±1.6 μg/mL). It is consistent with the literature report that TNF-α peaks at 2-4 h in mice post CLP induction and IL-1β and IL-6 onset at 4-8 h and last for 24 h after CLP surgery. Overall, greater than 93-99% of proinflammatory cytokines were removed from the septic plasma by nanotrap resin incubation. Another important observation was that one of the most important anti-inflammatory cytokine IL-10 was also removed by 70% after incubation with the positively charged PEGA-(ArgC17)$_4$ resin (FIG. 20*c*). A negatively charged PEGA-(OAC17)$_4$ was additionally applied to scavenge the positively charged IL-10 from septic plasma, which was expected to be more effective due to the paired charge interactions. As a result, PEGA-(OAC17)$_4$ showed similar efficiency with PEGA-(ArgC17)$_4$ in scavenging IL-10, which may be due to the slower kinetic protein adsorption on OA-containing nanotraps as shown in FIG. 17*b*. Consistent with the previous observation (FIG. 19*c*), the total protein levels in plasma were measured to be almost identical before and after bead incubation (Data not shown).

Conclusion. This disclosure demonstrated the immobilization of functional telodendrimer onto size-exclusive hydrogel resins for the simultaneous and selective removal of endotoxin and cytokines. TD nanotrap possesses a flexible dendritic architecture, which maximizes the conformational entropy in binding biomacromolecules via the synergistic combinations of the ubiquitous electrostatic and hydrophobic interactions. Both charges and hydrophobic moieties in TD nanotrap have demonstrated to be important for protein binding. The flexible hydrophobic moiety in TD nanotrap (e.g., C17), generally exhibits higher efficiency than rigid moieties in protein binding. The attractive ionic interactions between nanotrap and proteins are essential for the efficient protein adsorption. The TD nanotrap functionalized resins exhibit superior selectivity and efficiency in scavenging LPS at both pathological concentrations (10-1000 EU) and the elevated level of concentration (~$10^5$ EU) with consistent removal efficiencies of >90% in PBS, FBS, and whole blood. The results highlight both high affinity and superior capacity of the developed nanotrap resins. Accordingly, significant improved LPS attenuation was achieved in stimulating immune cells for TNF-α production in cell culture.

CLP-induced mouse sepsis models produce abundant inflammatory cytokines in response to the intraperitoneal infections and tissue damages. Three important proinflammatory cytokines, including TNF-α, IL-1β, and IL-6, were efficiently removed by 93-99% after incubation with PEGA-(ArgC17)$_4$ resin in vitro. In the future study, the developed TD nanotrap resins would be applied to pack hemoperfusion columns. The fluidic flow may further facilitate the mass transfer and improve adsorption efficiency than the static incubation applied in this study. Besides, the application of the mixtures of both NR$^{(-)}$ and NR$^{(+)}$ is able to target even broader range of cytokines, which may be beneficial to control cytokine storm and prevent immune paralysis in sepsis. In summary, it is promising to apply this nanotrap hemoperfusion device to improve sepsis treatment through the simultaneous removal of both endotoxin and cytokines and even broader range of septic molecules. The optimized TD nanotrap hemoperfusion for sepsis treatment will also be tested in larger animals (e.g., rats and pigs). This technology holds great potential for clinical translation to transform sepsis treatment in treating the critically ill patients with the risk of cytokine storm.

Experimental section. Materials and Methods. All materials, instrumental method, and synthesis procedures are described herein.

LPS attenuation. Macrophage RAW 264.7 cells were cultured in complete medium DMEM supplemented with 10% FBS, 100 U/ml penicillin, and 100 U/ml streptomycin at 37° C. using a humidified 5% $CO_2$ incubator. Cells were plated in 96 well plates at a density of $2 \times 10^4$ cells/well. LPS derived from *Pseudomonas aeruginosa* (L9143, Sigma-Aldrich) was pretreated with nanotrap beads for overnight incubation before added into macrophage cell culture. Control was made by adding stock LPS (500 ng/mL) without bead treatment to the cell. After 24 h incubation, supernatants were analyzed for TNF-α produced in the cell culture by Mouse TNF-α ELISA Ready-SET-GO assay (eBioscience™).

Sepsis models induced by cecal ligation and punctuation (CLP). Specific-pathogen free C57BL/6J mice (8-12 weeks, both sexes) purchased from Jackson Laboratory (Bar Harbor, Me.) were kept under pathogen-free conditions according to the AAALAC (Association for Assessment and Accreditation of Laboratory Animal Care) guidelines and were allowed to acclimatize for at least 4 days before any experiments. All the animal experiments were performed in the compliance with the institutional guidelines and according to the protocol approved by the Committee for the Humane Use of Animals of State University of New York Upstate Medical University.

In CLP procedure, mice were anesthetized using intraperitoneal ketamine/xylazine (90 mg/kg ketamine, 10 mg/kg xylazine) injection. After laparotomy, at 1.3 cm position of the cecum from distal pole to the base, a 5-0 silk ligature was made. The cecum was punctured twice with a 22-gauge needle and gently squeezed to extrude a 1 $mm^3$ column of fecal materials, and then returned to the abdominal cavity. The abdominal incision was closed with 5-0 silk sutures. After operation, mice were resuscitated with 1 mL warmed saline immediately. Buprenorphine (0.05 mg/kg, s.c) was injected for postoperative analgesia every 8 h. At 24 h post-CLP, mice were sacrificed under anesthesia. Blood was collected from the inferior vena cava, plasma was isolated and stored at −80° C. prior to resin treatment.

Ex vivo cytokine clearance. Septic plasma from CLP model was incubated with PEGA-(ArgC17)$_4$ resin with a liquid/bead volume ratio of 10:1 at room temperature for 4 h. The TNF-α, IL-1β, IL-6 and IL-10 concentrations in the plasma were analyzed for by ELISA assays in comparison to the untreated plasma.

Statistical analysis. Data are presented as means±standard deviation (SD). All statistical analyses were performed using Student's t-test for comparison of two groups. The level of statistical significance was set with $P<0.05$ considered significant.

Materials and Methods. All chemicals were used as received unless otherwise specified. Rink Amide-MBHA resin (HCRAm 04-1-1) was ordered from Nankai HECHENG S&T Co., Ltd (Tianjin, China). Amino PEGA resin (Novabiochem®, Darmstadt, Germany) was obtained from EMD Millipore (Billerica, Mass.). (Fmoc)-Lys(Boc)-OH, (Fmoc)-Lys(Fmoc)-OH, trifluoroacetic acid (TFA) and were obtained from Chem-Impex International, Inc. (Wood Dale, Ill.). (Fmoc)-Arg(Pbf)-OH were purchased from AnaSpec Inc. (San Jose, Calif.). N,N'-diisopropylcarbodiimide (DIC), N-hydroxybenzotriazole (HOBt), Succinic anhydride, 4-Dimethylaminopyridine (DMAP) and N,N-dimethylformamide, anhydrous (DMF, 99.8%) were received from Acros Organics (Belglum, N.J.). Polymyxin B Sulfate, Polymyxin B-Agarose (P1411), LPS from *Escherichia coli* (L4130) and *Pseudomonas aeruginosa* (L9143) were purchased from Sigma-Aldrich (St. Louis, Mo.). Polylysine-cellulose resin (Pierce™) was purchased from Thermo Scientific (Rockford, Ill.). Limulus amebocyte lysate (LAL) endotoxin quantification kit was purchased from Pierce™ (Thermo Scientific™, IL) and performed following the manufacturer's instructions.

Instrumental methods. Matrix-assisted laser desorption/ionization time-of-flight mass spectrometry (MALDI-TOF MS) spectra were collected on a Bruker Autoflex III system equipped with a Smart beam II laser source and acquired in positive, reflector mode. $^1$H NMR spectra were recorded on a 600 MHz Bruker AVANCE NMR spectrometer. Transmission electron microscopy (TEM) characterization of nanoparticle was performed on JEOL JEM-1400 operated at 80 kV. Samples were prepared on a glow discharged carbon-coated copper grids (CF300-CU, 300 mesh, Electron Microscopy Sciences). The hydrodynamic sizes of nanoparticles were acquired by dynamic light scattering (DLS) measurement using a particle analyzer (Microtrac Zetatract). Confocal microscope (Nikon) images were acquired in z-stacks mode having sequential optical x-y sections taken with a z-interval at 5 µm.

Solution phase telodendrimer synthesis. The synthesis of the free form telodendrimers bearing both guanidine and hydrophobic groups were described previously. Telodendrimer synthesis was initiated from methoxy-terminated amino PEG, MeO-PEG-NH$_2$ (Mw: 5 kDa). N-terminal-protected lysine was used to synthesize the branched scaffold of polylysine dendrons using HOBt/DIC as coupling reagents in anhydrous DMF at room temperature. All the reagents are in 3 equiv. stoichiometric excess relative to the primary amine. The completion of reactions was monitored by the chromogenic ninhydrin tests to probe the consumption of primary amine: dark blue indicates the presence of primary amine; yellow color indicates the completion of coupling. Fmoc-protecting group was removed by the treatment of 20% 4-methylpiperidine in DMF for 30 min. Pbf-protecting group was deprotected in the presence of TFA/DCM (50/50, v/v) for 2 h.

Solid-phase synthesis of LPS binding moieties. Starting from TentaGel (TG), or PEGA, or PVA-PEG resin, (Fmoc)-Lys(Fmoc)-OH and Fmoc-Oligo (ethylene glycol)-COOH linker were coupled sequentially following the standard peptide synthesis procedures. DIC and HOBt were used as catalytic coupling reagents. All reactants were in 3-fold excess with respect to the amine functional group on resin. After second generation dendritic oligolysine synthesis, (Fmoc)-Arg(Pbf)-OH was used to introduce the third layer of oligolysine on acid labile Rink resin and acid inert resin (TG, PEGA, and PVA-PEG) to introduce the orthogonally protected amine groups for charge and hydrophobic moiety conjugation. De-Fmoc was carried out in 20% 4-methylpiperidine DMF solution for 30 min. Pbf protecting group was removed in the presence of TFA/DCM (50/50, v/v) for 2 h. After the completion of each step reaction, residual reactants were removed under vacuum and washed with copious solvents of DMF, DCM, and MeOH sequentially. The LPS-binding hydrophobic building blocks were conjugated on the α-amine on the arginine after de-Fmoc step following the insertion of a triethyleneglycol linker molecule via the standard peptide synthesis procedure. LPS-binding dendron synthesized on Rink resin will be treated with TFA/TIS/H$_2$O (95/2.5/2.5, v/v/v) cocktail to cleave the arginine protecting group to release guanidine group, and simultaneously cleave the whole dendron from Rink resin into solution. In parallel, TG (PEGA or PVA-PEG) resin modified by LPS-binding dendron was washed intensively and readily available for LPS adsorption and removal.

Electrophoresis assays. The binding capacities of the telodendrimers with LPS and/or bovine serum albumin (BSA) were studied and compared with PMB binding using electrophoresis assay. The electrophoresis was carried out in 1.5% agarose gel (Tris-borate-EDTA (TBE) buffer) at constant current of 20 mA for 2 h. The gel was imaged by a Bio-Rad Universal Hood II Imager (Bio-Rad Laboratories, Inc.) under SYBR Green modes or photographed under UV illumination.

Fluorescent polarization assays. The fluorescence polarization (FP) was measured on the Multi-Mode Microplate Reader (Synergy™ 2, Biotek, VT) equipped with dichroic mirror (510 nm) and polarizing filter. The measurements were carried out on black flat bottom 96-well plates (Nunclon™ Surface, Roskilde, Denmark). The FP of LPS-FITC was record at excitation and emission filter of 485/20 nm and 528/20 nm, respectively. The experiments were performed in triplicate.

Resin binding assay for biological molecules. The desired amount of resin was weighed, hydrated, and incubated with fluorophore-labeled biological molecules including LPS, BSA, myoglobin (Mb), lysozyme, α-lactalbumin, and TNF-α in medium (PBS or FBS or whole blood) for defined time period. Then, the incubation solutions were collected for the fluorescence measurement by microplate reader (BioTek Synergy 2) and the resins were washed with PBS for three times. BSA-RB and/or LPS-FITC bound resins were then visualized under fluorescence microscopes.

Protein elution and MALDI-TOF MS analysis. Protein adsorbed nanotrap resins was washed with PBS intensively and drained to dryness using a centrifuge tube with filter (0.22 μm, Corning™ Costar™ Spin-X™). The resin was then incubated with two times volume of 6 M guanidine or 8 M urea solution at room temperature for overnight. The elution was collected and spotted on MTP 384 target plate (Bruker Daltonics) after mixing with CHCA matrix in 50% acetonitrile with 0.1% TFA. The spectra were collected using a linear mode.

Although the present disclosure has been described with respect to one or more particular embodiments and/or examples, it will be understood that other embodiments and/or examples of the present disclosure may be made without departing from the scope of the present disclosure.

The invention claimed is:

1. A sorption material, comprising at least one compound bound to a porous solid substrate, wherein the compound has the following structure:

$R^1$-$L^1$-D-($L^2$-$R^2$)x,y wherein $R^1$ is a bond or group attaching $L^1$ or D to the substrate;

$L^1$ and $L^2$ independently at each occurrence are optional and are linker groups;

D is a dendritic polymer moiety having one or more branched monomer units (X), and a plurality of end groups;

$R^2$ independently at each occurrence is an end group of the dendritic polymer;

x is the number of $R^2$ end groups that are charged moieties and range from 1-32; and y is the number of $R^2$ end groups that are each independently a lipophilic moiety or a hydrophobic moiety and range from 1-32.

2. A sorption material comprising at least one compound bound to a porous solid substrate, said compound having the following structure:

$R^1$-$L^1$-D-($L^2$-$R^2$)x,y wherein $R^1$ is a bond or group attaching $L^1$ or D to the substrate;

$L^1$ and $L^2$ independently at each occurrence are optional and are linker groups;

D is a dendritic polymer moiety having one or more branched monomer units (X), and a plurality of end groups;

$R^2$ independently at each occurrence is an end group of the dendritic polymer;

x is the number of $R^2$ end groups that are charged moieties and range from 1-32; and y is the number of $R^2$ end groups that are each independently a lipophilic moiety or a hydrophobic moiety and range from 1-32, wherein at least a portion of the substrate has size-exclusion pores with a molecular weight cutoff of less than or equal to 50 kDa.

3. A device for removing inflammation stimulating and/or mediating molecules from a fluid comprising: a housing defining an inlet and an outlet, wherein the inlet and the outlet are in fluid communication with one another, and the housing is configured such that the fluid enters the housing through the inlet and exits the housing through the outlet; and a sorption material is disposed in the housing, wherein the sorption material comprises at least one compound bound to a substrate, wherein the compound has the following structure:

$R^1$-$L^1$-D-($L^2$-$R^2$)$_{x,y}$ wherein $R^1$ is a bond or group attaching $L^1$ or D to the substrate;

$L^1$ and $L^2$ independently at each occurrence are optional and are linker groups;

D is a dendritic polymer moiety having one or more branched monomer units (X), and a plurality of end groups;

$R^2$ independently at each occurrence is an end group of the dendritic polymer;

x is the number of $R^2$ end groups that are charged moieties and range from 1-32; and y is the number of $R^2$ end groups that are each independently a lipophilic moiety or a hydrophobic moiety and range from 1-32.

4. A method for treating a subject having or suspected of having a systemic infection and/or systemic inflammation comprising:

contacting a biological fluid containing one or more of an inflammation stimulating molecule and/or a mediating molecule from the subject with at least one sorption material, wherein the at least one sorption material comprises at least one compound bound to a substrate, wherein the compound has the following structure:

$R^1$-$L^1$-D-($L^2$-$R^2$)x,y wherein $R^1$ is a bond or group attaching $L^1$ or D to the substrate;

$L^1$ and $L^2$ independently at each occurrence are optional and are linker groups;

D is a dendritic polymer moiety having one or more branched monomer units (X), and a plurality of end groups;

$R^2$ independently at each occurrence is an end group of the dendritic polymer;

x is the number of $R^2$ end groups that are charged moieties and range from 1-32; and y is the number of $R^2$ end groups that are each independently a lipophilic moiety or a hydrophobic moiety and range from 1-32, and wherein at least a portion of or all of the one or more of or all of inflammation stimulating and/or mediating molecules bind to the sorption material.

5. The method of claim 4, wherein the contacting comprises passing said biological fluid through a housing, wherein the housing includes an inlet and an outlet, wherein the inlet and the outlet are in fluid communication, and the housing is configured such that the fluid enters the housing through the inlet and exits the housing through the outlet, wherein the at least one sorption material is disposed in the housing.

6. The method of claim 4, wherein the method further comprises returning the biological fluid to the subject.

7. The method of claim 4, wherein the biological fluid is blood, serum, culture media, or a combination thereof.

8. The method of claim 4, wherein the substrate is a hydrogel network or solid substrate.

9. The method of claim 8, wherein the solid substrate is porous.

* * * * *